United States Patent [19]

Gaylor et al.

[11] Patent Number: 5,034,548

[45] Date of Patent: Jul. 23, 1991

[54] STEROID DERIVATIVES USEFUL AS HYPOCHOLESTEROLEMICS

[75] Inventors: James L. Gaylor, Skillman, N.J.; Paul R. Johnson, Newark; Soo S. Ko, Wilmington, both of Del.; Ronald L. Magolda, Aston, Pa.; Simon H. Stam, San Jose, Calif.; James M. Trzaskos, Boothwyn, Pa.

[73] Assignee: E. I. Du Pont de Nemours and Company, Wilmington, Del.

[21] Appl. No.: 596,378

[22] Filed: Oct. 16, 1990

Related U.S. Application Data

[63] Continuation of Ser. No. 316,066, Feb. 27, 1989, abandoned, which is a continuation-in-part of Ser. No. 90,634, Aug. 28, 1987, abandoned, which is a continuation-in-part of Ser. No. 8,812, Jan. 30, 1987, abandoned.

[51] Int. Cl. ................................................. C07J 9/00
[52] U.S. Cl. ............................... 552/540; 552/515; 552/516; 552/519; 552/523; 552/537; 552/526; 552/540; 552/544; 540/94; 540/120
[58] Field of Search ............... 552/515, 516, 519, 523, 552/526, 539, 540, 544; 540/94, 120

[56] References Cited

U.S. PATENT DOCUMENTS 4,202,891  5/1980  Schroepfer, Jr. et al. .......... 424/242
4,230,626 10/1980  Chorvat ............................. 260/397

OTHER PUBLICATIONS

"The Sterols of the Echinoderm *Asterias rubens*" Smith et al. Biochem. J. 135:443-455 (1973).
Regulation of Cholesterol Biosynthesis in Cultured Cells by Probable Natural Precursor Steroids, Gibbons et al., J. Biol. Chem. 255(2) 395-400, (1980).
The Synthesis of Lanosterol, Woodward et al., J. Chem. Soc. (1957) 1132-1144 & Chem. Abst. 51:1213d comput. printout.
"Conformational Anomalies in Some Triterpenoid Bromoketones" Barton et al., Chem. Abst. 51:17975 & comput. print-out.
Kannel et al., Ann. Intern. Med., 90:85-91 (1979).
Final Report of the Pooling Project, J. Chron. Dis, 31:201-306 (1978).
Brensike et al., Circulation, 69:313-324 (1984).
Levy et al., Circulation, 69:325-337 (1984).
Rodwell et al., Adv. Lipid Res., 14:1-74 (1976).
Brown et al., J. Lipid Res., 21:505-517 (1980).
Breslow et al., Biochem. Biophys. Acta, 398:10-17 (1975).
Kandutsch et al., J. Biol. Chem., 252:409-415 (1977).
Chen et al., J. Biol. Chem., 254:715-720 (1979).
Kandutsch et al., Science, 201:498-501 (1978).
Havel et al., J. Biol. Chem., 254:9573-9582 (1979).
Chang et al., J. Biol. Chem., 255: 7787-7795 (1980).
Kandutsch et al., J. Biol. Chem., 255:10813-10821 (1980).
Gibbons et al., J. Biol. Chem., 255:395-400 (1980).

Cavenee et al., J. Biol. Chem., 256: 2675-2681 (1981).
Tanaka et al., J. Biol. Chem., 258: 1331-1339 91983).
Trzskos et al., Fed. Proc., 44:656, (1985) (Abstract #1451).
Schroepfer et al., Proc. Natl. Acad. Sci. U.S.A., 81:5851-6865 (1984).
Batten et al., "The Synthesis of Some 32-Functionalised Lanostane Derivatives", J. Chem. Soc. (cc) 739-748 (1972).
J. Fried, et al., "32-Hydroxylated Lanostane Derivatives by Photolysis of 3$\beta$-Acetoxy-7-Ketolanostane" Tetrahedron Letters No. 15 pp. 1677-1680 (1966).
T. J. Bentley et al., "The Synthesis of 32-Oxygenated Lanostane Derivatives" Tetrahedron Letters No. 29, pp. 2497-2498 (1965).
Sonoda, et al,. "A Simplified Synthesis of 32-Oxygenated Lanosterol Derivatives" Chem. Pharm. Bull 35 pp. 394-397 (1987).
M. Morisaki, et al., "Inhibitory Effect of 15-Oxygenated Sterols on Cholesterol Synthesis 24,25-Dihydrolanosterol" J. Biochem. 99, pp. 597-600 (1986).
C. Tabacik, et al., "Post-HMG CoA Reductase Regulation of Cholesterol Biosynthesis in Normal Human Lymphocytes: Lanosten-3$\beta$-ol-32-al, A Natural Inhibitor". Biochem. Biophys. Res. Commun. 101, pp. 1087-1095 (1981).
Spike et al., "Structure of a Potential Intermediate in Cholesterol Biosynthesis" J.C.S. Chem. Comm. pp. 477-478 (1974).
Parish et al., "Synthesis and Structure of 15-Oxygenated 5$\alpha$, 14$\beta$-cholest-7-en-3$\beta$-ol Derivatives" Tetrahedron Letters 49, pp. 4401-4404 (1976).
Y. Aoyama, et al., "Metabolism of 32-Hydroxy-24,-25-dihydrolanosterol by Purified Cytochrome P-45-0$_{yDM}$ from Yeast" J. Bio. Chem. 262, pp. 1239-1243 (1987).
G. F. Gibbons et al., "Synthesis and Configuration at C-15 of the Epimeric 5$\alpha$-lanost-8-en-3$\beta$, 15-diols" J.C.S. Chem. Comm. pp. 213-214 (1975).
R. B. Woodward et al., "The Synthesis of Lanosterol (Lanostadienol)" J. Chem. Soc., pp. 1131-1144 (1975).
M. Morisak "Inhibitory Effect of 15-Oxygenated Sterols on Cholesterol Synthesis from 24-,25-Dihydrolanosterol" J. Biochem. Vol. 99, pp. 597-600 (1986).
Barton et al., "Conformational Anomalies in Some Triterpenoid Bromoketones" J. Chem. Soc., pp. 2907-2915 (1957).

(List continued on next page.)

*Primary Examiner*—Helen M. S. Sneed
*Assistant Examiner*—James Saba

[57] ABSTRACT

Lanosterols substituted in the 14 and/or 15 position(s) which are active in inhibiting lanosta-8,24-dien-3$\beta$-ol 14$\alpha$-methyl-demethylase activity, suppressing 3-hydroxy-3-methylglutaryl coenzyme A reductase (HMGR) activity, decreasing cholesterol synthesis and reducing serum cholesterol levels are disclosed.

69 Claims, No Drawings

OTHER PUBLICATIONS

T. J. Bentley et al., "The Synthesis and Configuration of Some 32-Norlanosterol Derivatives" J.C.S. Perkin I, pp. 749–754 (1972).

L. L. Frye et al., "Novel Inhibitors of Lanosterol 14α-Methyl Demethylase, a Critical Enzyme in Cholesterol Biosynthesis" J. Chem. Soc. Chem. Commun., pp. 129–131 (1988).

Y. Sonoda et al., Chem. Abst. 109:225w (1988).

E. J. Parish et al., "Sterol Synthesis," J. Lipid Res. vol. 22, pp. 859–868 (1981).

J. M. Trzaskos et al., "Mechanistic Studies of Lanosterol C-32 Demethylation" J. Biol. Chem. vol. 261, pp. 16937–16942 (1986).

M. Anastasia et al., "15-Oxygenated Sterols by M-Chloroperbenzoic Acid Oxidation of 3β-Acetoxy-5α-cholesta-8, 14-drene" J. Org. Chem. vol. 46, pp. 3265–3267 (1981).

D. O. Woodward et al., "Purification and Properties of Neurospora Adenylosuccinase" J. Biol. Chem. vol. 241, pp. 580–587 (1966).

A. Shafiee et al., "Oxidative Demethylation of Lanosterol in Cholesterol Biosynthesis: Accumulation of Sterol Intermediates", J. Lipid Res. vol. 27, pp. 1–9 (1986).

M. Anastasia et al., "Synthesis of 11-and 15-Oxygenated Steroids, The Course of 8,14–Dienes Oxidation by Chromic Acid" J. Org. Chem. vol. 48, pp. 686–689 (1983).

S. Erickson et al., "7-Ketocholesterol" J. Biol. Chem. vol. 252, pp. 5186–5193 (1977).

J. C. Knight et al., "The Structure of the Cactus Sterol Macdougallin (14α-Methyl-Δ8-Cholestene-3β, 6α-diol). A Novel Link in Sterol Biogenesis" J. Am. Chem. Soc., 88:4, pp. 790–798 (1966).

J. C. Knight et al., "The Synthesis of Tritium-Labeled 14α-Methyl-5α-cholest-7-en-3β-ol and Its Enzymatic Demethylation" J. Biol. Chem. vol. 241, pp. 1502–1508 (1966).

D. A. Leonard et al., "ATP-Dependent Degradation of 3-Hydroxy-3-Methylglutaryl Coenzyme A Reductase in Permeabilized Cells" J. Biol. Chem. vol. 262, pp. 7914–7919 (1987).

STEROID DERIVATIVES USEFUL AS HYPOCHOLESTEROLEMICS

RELATED APPLICATIONS

This application is a continuation of application Ser. No. 07/316,066, filed Feb. 27, 1988 now abandoned, which is a continuation-in-part of application Ser. No. 090,634, filed Aug. 28, 1987 now abandoned, which is a continuation-in-part of application Ser. No. 008,812, filed Jan. 30, 1987 now abandoned.

BACKGROUND OF THE INVENTION

1. Field of the Invention

The present invention relates to 14,15-substituted lanosterols, to pharmaceutical compositions containing such compounds and to the use of these compounds to inhibit the activity of lanosta-8,24-dien-3$\beta$-ol 14$\alpha$-methyl-demethylase and suppress the activity 3-hydroxy-3-methylglutaryl coenzyme A reductase (HMGR), two enzymes which are important in cholesterol biosynthesis. The overall effect of these 14,15-substituted lanosterols is to decrease cholesterol formation, thereby resulting in lower serum cholesterol levels in mammals.

2. State of the Art

Elevated concentrations of serum cholesterol have been demonstrated by a number of clinical studies to be a major contributing factor in the development and progression of atherosclerosis, a disease characterized by the formation of cholesterol-containing plaques in the aorta and lesser arteries. The plaques tend to clog the arterial passage ways, making it difficult, if not impossible, for blood to flow from the heart to various tissues in the body. This pathobiological condition can ultimately lead to Coronary Heart Disease (CHD). See, e.g., Kannel et al., Ann. Intern. Med., 90:85–91 (1979); Final Report of the Pooling Project, J. Chron. Dis., 31:201–306 (1978). By maintaining low cholesterol levels in the blood, arterial plaque formation and CHD can potentially be avoided. See, e.g., Brensike et al., Circulation, 69:313–324 (2984) and Levy et al., Circulation, 69:325–337 (1984).

In mammals, serum cholesterol is derived from exogenous dietary sources as well as through endogenous de novo synthesis. Endogenous synthesis of cholesterol involves a complex set of enzyme-catalyzed reactions and regulatory mechanisms which to date are only partially understood. As Rodwell et al., Adv. Lipid Res., 14:1–74 (1976) indicate, 3-hydroxy-3-methylglytaryl coenzyme A reductase (HMGR is generally accepted as the rate-limiting enzyme which controls cholesterol biosynthesis from acetyl-CoA in all organisms. Brown et al., J. Lipid Res., 21:505–517 (1980) have shown that regulation of HMGR is a complex process which is under a feedback control mechanism involving both steroidal as well as nonsteroidal isoprenoid metabolites. The authors point out that under normal conditions, the ability of cholesterol to regulate its own biosynthesis when associated with lipoprotein particles is one aspect of this feedback control mechanism. In addition, it has been demonstrated that various oxygenated sterols, when used in a highly purified state, are even more effective than cholesterol in attenuating the amount of HMGR activity, see Breslow et al., Biochem. Biophys. Acta, 398:10–17 (1975), Kandutsch et al., J. Biol. Chem., 252:409–415 (1977), and Chen et al., J. Biol. Chem., 254:715–720 (1979), leading to the hypothesis that oxysterols may also be endogenous mediators which regulate HMGR activity and cholesterol synthesis in situ. See Kandutsch et al., Science, 201:498–501 (1978).

This proposition stimulated considerable research activity. See, e.g., Chen et al., J. Biol. Chem., 254:715–720 (1979); Havel et al., J. Biol. Chem., 254:9573;14 9582 (1979); Chang et al., J. Biol. Chem., 255:7787–7795 (1980); Chorvat, U.S. Pat. No. 4,230,626 (1980); Gibbons et al., J. Biol. Chem., 255:395–400, (1980); Kandutsch et al., J. Biol. Chem., 255:10814–10821 (1980); Cavenee et al., J. Biol. Chem., 256:2675–2681 (1981); Tanaka et al., J. Biol. Chem., 258:13331–13339 (1983); and Trzaskos et al., Fed. Proc., 44:656, (1985). As a result, a number of inhibitors of HMGR activity have been found.

Gibbons et al., J. Biol. Chem., 255:395–400 (1980), for example, have shown that certain synthetic oxygenated lanosterol derivatives are active inhibitors of HMGR activity. Trzaskos et al., Fed. Proc., 44:656 (1985) have established that in situ generation of the Gibbons compounds leads to attenuated HMGR activity and decreased cholesterol biosynthesis.

In addition, Schroepfer et al., U.S. Pat. No. 4,202,891 and Schroepfer et al., Proc. Natl. Acad. Sci. USA, 81:6861–6865 (1984) have revealed that other oxygenated lanosterol derivatives may be successfully employed to lower serum cholesterol levels in animals.

Additional compounds which affect HMGR and/or other enzymes critical to serum cholesterol biosynthesis are needed. The present invention is directed to this end.

SUMMARY OF THE INVENTION

The present invention provides novel 14,15-substituted lanosterol compounds of the formula:

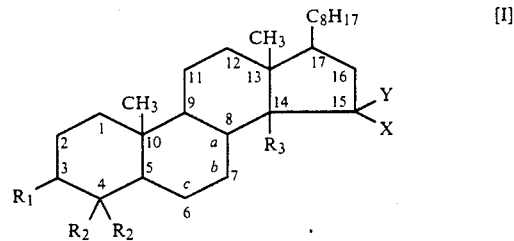

wherein
$R_1$ is $=O$, $OL_1$, or $OCOL_1$;
$R_2$ is H, $C_1$–$C_6$ alkyl, $C_2$–$C_6$ alkenyl, $C_2$–$C_6$ alkynyl or aryl-$C_1$–$C_6$-alkyl;
$R_3$ is H, $C_1$–$C_6$ alkyl, $C_2$–$C_6$ alkenyl, $C_2$–$C_6$ alkynyl, aryl-$C_1$–$C_6$-alkyl, $CH_2OR_4$, $CH_2CH_2OR_4$, $CHNOR_4$, $CH_2SR_4$, $CH_2CH_2SR_4$, $CHOR_4L_2$, $CHOR_5L_2$, $CN$, $CHZ_2$, $CHR_4N(R_4)_2$, $CH_2CH_2N(R_4)_2$, $CH_2CH_2Z$, $N(R_4)_2$, $SR_4$, $OR_4$, poly-$(OR_4, OR_5,$ epoxy$)$ $C_1$–$C_6$ alkyl, $NR_4R_5$, $OR_5$, $CH_2CH_2OR_5$, $CHNOR_5$, $CH_2CH_2SR_5$, $CH_2CH_2NR_4OR_4$, $CHR_4NR_4OR_5$, $COL_3$, $C(NR_4)L_2$, $CH_2CH_2NR_4OR_5$, $CHR_4NR_4OR_4$, $CHR_4NR_5OR_5$, $CR_4=CR_4C(R_4)_2Z$, $CR_4=CR_4C(R_4)_2OR_5$, $CR_4=CR_4C(R_4)_2OR_4$, $C(O)NR_4OR_4$, $C(O)NR_4OR_5$, $CHO$, $CR_4=CR_4R_5$, $C(R_4)_2OR_4$, $C(R_4)_2OR_5$, $C(R_4)_2CR_4NOR_4$ or $C(R_4)_2CR_4NOR_5$;
$R_4$ is H, $C_1$–$C_6$ alkyl, $C_2$–$C_6$ alkenyl, aryl, aryl-$C_1$–$C_6$-alkyl or $C_2$–$C_6$ alkynyl;
$R_5$ is $COL_3$;

X and Y, independently, are H, $C_1$–$C_6$ alkyl, Z, $OR_4$, $OR_5$, $SR_4$, $SR_5$, $N(R_4)_2$, $N(R_5)_2$, $NR_4R_5$, $NR_4OR_4$ or $NR_4OR_5$; or X and Y, taken together, are $NR_4$, $NR_5$, $NOR_4$, $NOR_5$, S, $C(R_4)_2$, $C(R_5)_2$, $CR_5R_4$ or O;

Z is halogen;

$L_1$ is H, $C_1$–$C_{20}$ alkyl, $C_2$–$C_{20}$ alkenyl, aryl, aryl-$C_1$–$C_{20}$-alkyl, or $C_2$–$C_{20}$ alkynyl;

$L_2$ is H, $C_1$–$C_6$ alkyl, $C_2$–$C_6$ alkenyl, aryl, aryl-$C_1$–$C_6$-alkyl, or $C_2$–$C_6$ alkynyl;

$L_3$ is $C_1$–$C_6$ alkyl, $C_2$–$C_6$ alkenyl, aryl, aryl-$C_1$–$C_6$-alkyl, $C_2$–$C_6$ alkynyl, $OR_4$, or $N(R_4)_2$;

and their physiologically acceptable salts; provided that (a) when $R_3$ is CHO, and X and Y are both H, and carbons 7-8 or 8-9 are unsaturated, then $R_1$ is other than OH or $OCOCH_3$, and $R_2$ is other than $CH_3$;

(b) when $R_3$ is $CH_3$ and carbons 7-8 or 8-9 are unsaturated, then $R_1$ is other than OH or $OCOCH_3$, $R_2$ is other than $CH_3$ or H, and X and Y are other than OH, $OCOCH_3$ or H;

(c) when $R_1$ is =O, or is $OL_1$ where $L_1$ is H or $C_1$–$C_6$ alkyl, or is $OCOL_1$ when $L_1$ is $C_1$–$C_{20}$ alkyl or phenyl, and X is $OR_4$ or $OR_5$ where $R_4$ is H or $OR_5$ is $OCOL_3$ where $L_3$ is $C_1$–$C_{20}$ alkyl or phenyl, and Y is H or OH, then $R_3$ is other than H or α $C_1$–$C_6$ alkyl;

(d) when $R_3$ is $CH_2OH$ or $CH_2OCOCH_3$, and $R_2$ is H or $CH_3$, and carbons 6-7, 7-8 or 8-9 are unsaturated, then $R_1$ is other than =O or OH or $OCOCH_3$, and X is other than H or OH;

(e) when X and Y are both H, then $R_3$ is other than H or $CH_3$;

(f) when X and Y are both H, then $R_3$ is other than OH, and $R_2$ is other than H;

(g) when $R_2$ is H, and $R_3$ is α OH, and X is β OH, and Y is α H, and carbons 6-7, 7-8, or 8-9 are saturated, then $R_1$ is other than OH;

(h) where X is OH, $OR_5$, $N(R_4)_2$, $N(R_5)_2$, $NR_4R_5$, $SR_5$, $NR_4OR_4$, or $NR_4OR_5$, then Y is other than Z, OH, $OR_5$, $SR_5$, $NR_4OR_4$, $NR_4OR_5$, $N(R_4)_2$, or $N(R_5)_2$;

(i) when $R_3$ is H, OH, or $C_1$–$C_6$ alkyl, then X and Y, taken together, are other than O;

(j) when $R_3$ is α OH, X is α OH and Y is H, and carbons 8-9 are unsaturated, then $R_1$ is other than $OCOCH_3$;

(k) when $R_3$ is CN, or CHNOH and carbons 7-8 are unsaturated, then $R_1$ is other than $OCOCH_3$, $R_2$ is other than H or $CH_3$, and X and Y are other than H; and (l) when $R_3$ is CONHOH or $CONHOCOCH_3$, and X and Y are both H, and $R_2$ is $CH_3$, and carbons 7-8 are unsaturated, then $R_1$ is other than OH or $OCOCH_3$.

The above compounds, as well as certain other compounds, are effective inhibitors of lanosta-8,24-dien-3β-ol 14α-methyl-demethylase activity and suppressants of 3-hydroxy-3-methylglutaryl coenzyme A reductase (HMGR) activity. By interfering with these enzymes, both of which are essential in the cholesterol biosynthetic pathway, cholesterol formation is decreased and serum cholesterol levels lowered.

Thus, the present invention also includes therapeutic pharmaceutical compositions for inhibiting lanosta-8,24-dien-3β-ol 14α-methyl-demethylase activity, suppressing HMGR activity, decreasing cholesterol formation and lowering serum cholesterol levels in mammals.

The pharmaceutical compositions comprise (i) an effective amount of a compound of the formula:

wherein $R_1$ is =O, $OL_1$, or $OCOL_1$;

$R_2$ is H, $C_1$–$C_6$ alkyl, $C_2$–$C_6$ alkenyl, $C_2$–$C_6$ alkynyl or aryl-$C_1$–$C_6$-alkyl;

$R_3$ is H, $C_1$–$C_6$ alkyl, $C_2$–$C_6$ alkenyl, $C_2$–$C_6$ alkynyl, aryl-$C_1$–$C_6$-alkyl, CHO, $CH_2OR_4$, $CH_2CH_2OR_4$, $CHNOR_4$, $CH_2SR_4$, $CH_2CH_2SR_4$, $CHOHL_2$, $CHOR_4L_2$, $CHOR_5L_2$, CN, $CHZ_2$, $CH_2Z$, CHS, $CHR_4N(R_4)_2$, $CH_2CH_2N(R_4)_2$, $CH_2CH_2Z$, $N(R_4)_2$, $SR_4$, $OR_4$, $CH=NNHR_4$, poly-($OR_4$, $OR_5$, epoxy) $C_1$–$C_6$ alkyl, $N(R_5)_2$, $NR_4R_5$, $SR_5$, $OR_5$, $CH=NNHR_5$, $CH_2OR_5$, $CH_2CH_2OR_5$, $CHNOR_5$, $CH_2SR_5$, $CH_2CH_2SR_5$, $CHR_4N(R_5)_2$, $CHR_4NR_4R_5$, $CH_2CH_2N(R_5)_2$, $CH_2CH_2NR_4R_5$, $CH_2CH_2NR_4OR_4$, $CHR_4NR_4OR_5$, $COL_4$, $CSL_4$, $C(NR_4)L_4$, $C(NR_4)SR_4$, $C(S)SR_4$, $CHR_4NR_4N(R_4)_2$, $CHR_4NR_5N(R_4)_2$, $CHR_4NR_4NR_4R_5$, $CHR_4NR_4NR_4R_5$, $CHR_4NR_4N(R_5)_2$, $CHR_4NR_5N(R_5)_2$, $CH_2CH_2NR_4OR_5$, $CHR_4NR_4OR_4$, $CHR_4NR_5OR_5$, $CHR_4NR_5OR_4$, $CH_2CH_2NR_5OR_5$, $CH_2CH_2NR_5OR_4$, $CR_4=CR_4R_5$, $C\equiv CR_5$, $CR_4=CR_4C(R_4)_2Z$, $C\equiv C-C(R_4)_2Z$, $CR_4=CR_4C(R_4)_2OR_5$, $C\equiv C-C(R_4)_2OR_5$, $CR_4=CR_4C(R_4)_2OR_4$, $C\equiv C-C(R_4)_2OR_4$, $C(O)NR_4OR_4$, $C(O)NR_4OR_5$, $C(S)NR_4OR_4$, $C(S)NR_4OR_5$, $C(R_4)_2OR_4$, $C(R_4)_2OR_5$, $CHR_4NR_4SO_2L_4$, $CH_2CHR_4NR_4SO_2L_4$, $C(R_4)_2CR_4NOR_4$, $C(R_4)_2CR_4NOR_5$, $C(R_4)_2L_5$, $CR_4L_5OR_4$, or $CR_4L_5SR_4$;

$R_4$ is H, $C_1$–$C_6$ alkyl, $C_2$–$C_6$ alkenyl, aryl, aryl-$C_1$–$C_6$-alkyl or $C_2$–$C_6$ alkynyl;

$R_5$ is $COL_3$, $CSL_3$ or $C(NR_4)L_3$;

X and Y, independently, are H, $C_1$–$C_6$ alkyl, Z, $OR_4$, $OR_5$, $SR_4$, $SR_5$, $N(R_4)_2$, $N(R_5)_2$, $NR_4R_5$, $NR_4OR_4$, $NR_4N(R_4)_2$, $NR_4NR_4R_5$, $NR_4N(R_5)_2$, $NR_5N(R_4)_2$, $NR_5NR_4R_5$, or $NR_5N(R_5)_2$; or X and Y, taken together, are $NR_4$, $NR_5$, $NOR_4$, $NOR_5$, S, $C(R_4)_2$, $C(R_5)_2$, $CR_5R_4$, $NN(R_4)_2$, $NNR_4R_5$, $NN(R_5)_2$, or O;

Z is halogen;

$L_1$ is H, $C_1$–$C_{20}$ alkyl, $C_2$–$C_{20}$ alkenyl, aryl, aryl-$C_1$–$C_{20}$-alkyl, or $C_2$–$C_{20}$ alkynyl;

$L_2$ is H, $C_1$–$C_6$ alkyl, $C_2$–$C_6$ alkenyl, aryl, aryl-$C_1$–$C_6$-alkyl, or $C_2$–$C_6$ alkynyl;

$L_3$ is H, $C_1$–$C_6$ alkyl, $C_2$–$C_6$ alkenyl, aryl, aryl-$C_1$–$C_6$-alkyl, $C_2$–$C_6$ alkynyl, $OR_4$, or $N(R_4)_2$;

$L_4$ is $C_1$–$C_6$ alkyl, $C_2$–$C_6$ alkenyl, aryl, aryl-$C_1$–$C_6$-alkyl, $C_2$–$C_6$ alkynyl, $OR_4$, or $N(R_4)_2$; and $L_5$ is a 5- or 6-membered aromatic heterocyclic ring containing 1 or 2 nitrogen atoms as part of the ring, said ring optionally substituted with substituents selected from the group consisting of $C_1-C_6$ alkyl and $C_2-C_6$ alkenyl;

and their physiologically acceptable salts; provided that (a) when $R_3$ is CHO, and X and Y are both H, and carbons 7-8 or 8-9 are unsaturated, then $R_1$ is other than OH or OCOCH$_3$, and $R_2$ is other than CH$_3$;

(b) when $R_3$ is CH$_3$ and carbons 7-8 or 8-9 are unsaturated, then $R_1$ is other than OH or OCOCH$_3$, $R_2$ is other than CH$_3$ or H, and X and Y are other than OH, OCOCH$_3$ or H;

(c) when $R_1$ is =O, or is OL$_1$ where $L_1$ is H or $C_1-C_6$ alkyl, or is OCOL$_1$ when $L_1$ is $C_1-C_{20}$ alkyl or phenyl, and X is OR$_4$ or OR$_5$ where $R_4$ is H or OR$_5$ is OCOL$_3$ where $L_3$ is $C_1-C_{20}$ alkyl or phenyl, and Y is H or OH, then $R_3$ is other than H or $\alpha C_1-C_6$ alkyl;

(d) when $R_3$ is CH$_2$OH or CH$_2$OCOCH$_3$, and $R_2$ is H or CH$_3$, and carbons 6-7, 7-8 or 8-9 are unsaturated, then $R_1$ is other than =O or OH or OCOCH$_3$, and X is other than H or OH;

(e) when X and Y are both H, then $R_3$ is other than H or CH$_3$;

(f) when X and Y are both H, then $R_3$ is other than OH, and $R_2$ is other than H;

(g) when $R_2$ is H, and $R_3$ is $\alpha$ OH, and X is $\beta$ OH, and Y is $\alpha$ H, and carbons 6-7, 7-8, or 8-9 are saturated, then $R_1$ is other than OH;

(h) when X is OH, OR$_5$, N(R$_4$)$_2$, N(R$_5$)$_2$, NR$_4$R$_5$, SR$_5$, NR$_4$OR$_4$, or NR$_4$OR$_5$, then Y is other than Z, OH, OR$_5$, SR$_5$, NR$_4$OR$_4$, NR$_4$OR$_5$, N(R$_4$)$_2$, or N(R$_5$)$_2$;

(i) when $R_3$ is H, OH, or $C_1-C_6$ alkyl, then X and Y, taken together, are other than O;

and (ii) a pharmaceutically acceptable carrier or diluent.

In addition, the present invention encompasses methods for inhibiting lanosta-8,24-dien-3$\beta$-ol 14$\alpha$-methyl-demethylase activity, suppressing HMGR activity, decreasing cholesterol formation and lowering serum cholesterol levels comprising administering to a mammal an effective amount of a compound of the formula:

wherein
$R_1$ is =O, OL$_1$, or OCOL$_1$;

$R_2$ is H, $C_1-C_6$ alkyl, $C_2-C_6$ alkenyl, alkynyl or aryl-$C_1-C_6$-alkyl;

$R_3$ is H, $C_1-C_6$ alkyl, $C_2-C_6$ alkenyl, $C_2-C_6$ alkynyl, aryl-$C_1-C_6$-alkyl, CHO, CH$_2$OR$_4$, CH$_2$CH$_2$OR$_4$, CHNOR$_4$, CH$_2$SR$_4$, CH$_2$CH$_2$SR$_4$, CHOHL$_2$, CHOR$_4$L$_2$, CHOR$_5$,L$_2$, CN, CHZ$_2$, CH$_2$Z, CHS, CHR$_4$N(R$_4$)$_2$, CH$_2$CH$_2$N(R$_4$)$_2$, CH$_2$CH$_2$Z, N(R$_4$)$_2$, SR$_4$, OR$_4$, CH=NNHR$_4$, poly-(OR$_4$, OR$_5$, epoxy) $C_1-C_6$ alkyl, N(R$_5$)$_2$, NR$_4$R$_5$, SR$_5$, OR$_5$, CH=NNHR$_5$, CH$_2$OR$_5$, CH$_2$CH$_2$OR$_5$, CHNOR$_5$, CH$_2$SR$_5$, CH$_2$CH$_2$SR$_5$, CHR$_4$N(R$_5$)$_2$, CHR$_4$NR$_4$R$_5$, CH$_2$CH$_2$N(R$_5$)$_2$, CH$_2$CH$_2$NR$_4$R$_5$, CH$_2$CH$_2$NR$_4$OR$_4$, CHR$_4$NR$_4$OR$_5$, COL$_4$, CSL$_4$, C(NR$_4$)L$_4$, C(NR$_4$)SR$_4$, C(S)SR$_4$, CHR$_4$NR$_4$N(R$_4$)$_2$, CHR$_4$NR$_4$NR$_4$R$_5$, CHR$_4$NR$_4$N(R$_5$)$_2$, CH$_2$CH$_2$NR$_4$OR$_5$, CHR$_4$NR$_5$OR$_5$, CH$_2$CH$_2$NR$_5$OR$_5$, CR$_4$=CR$_4$R$_5$, C≡CR$_5$, C≡C—C(R$_4$)Z, CR$_4$=CR$_4$C(R$_4$)$_2$OR$_5$, C≡C—C(R$_4$)$_2$OR$_5$, CR$_4$=CR$_4$C(R$_4$)$_2$OR$_4$, C≡C—C(R$_4$)$_2$OR$_4$, C(O)NR$_4$OR$_4$, C(O)NR$_4$OR$_5$, C(S)NR$_4$OR$_4$, C(S)NR$_4$OR$_5$, C(R$_4$)$_2$OR$_4$, C(R$_4$)$_2$OR$_5$, CHR$_4$NR$_4$SO$_2$L$_4$, CH$_2$CHR$_4$NR$_4$SO$_2$L$_4$, C(R$_4$)$_2$CR$_4$NOR$_4$, C(R$_4$)$_2$CR$_4$NOR$_5$, C(R$_4$)$_2$L$_5$, CR$_4$L$_5$OR$_4$, or CR$_4$L$_5$SR$_4$;

$R_4$ is H, $C_1-C_6$ alkyl, $C_2-C_6$ alkenyl, aryl, aryl-$C_1-C_6$-alkyl or $C_2-C_6$ alkynyl;

$R_5$ is COL$_3$, CSL$_3$, or C(NR$_4$)L$_3$;

X and Y, independently, are H, $C_1-C_6$ alkyl, Z, OR$_4$, OR$_5$, SR$_4$, SR$_5$, N(R$_4$)$_2$, N(R$_5$)$_2$, NR$_4$R$_5$, NR$_4$OR$_4$, NR$_4$OR$_5$, NR$_4$N(R$_4$)$_2$, NR$_4$NR$_4$R$_5$, NR$_4$N(R$_5$)$_2$, NR$_5$N(R$_4$)$_2$, NR$_5$NR$_4$R$_5$, or NR$_5$N(R$_5$)$_2$; or X and Y, taken together, are NR$_4$, NR$_5$, NOR$_4$, NOR$_5$, S, C(R$_4$)$_2$, C(R$_5$)$_2$, CR$_5$R$_4$, NN(R$_4$)$_2$, NNR$_4$R$_5$, NN(R$_5$)$_2$, or O;

Z is halogen;

$L_1$ is H, $C_1-C_{20}$ alkyl, $C_2-C_{20}$ alkenyl, aryl, aryl-$C_1-C_{20}$-alkyl, or $C_2-C_{20}$ alkynyl;

$L_2$ is H, $C_1-C_6$ alkyl, $C_2-C_6$ alkenyl, aryl, aryl-$C_1-C_6$-alkyl, or $C_2-C_6$ alkynyl;

$L_3$ is H, $C_1-C_6$ alkyl, $C_2-C_6$ alkenyl, aryl, aryl-$C_1-C_6$-alkyl, $C_2-C_6$ alkynyl, OR$_4$, or N(R$_4$)$_2$;

$L_4$ is $C_1-C_6$ alkyl, $C_2-C_6$ alkenyl, aryl, aryl-$C_1-C_6$-alkyl, $C_2-C_6$ alkynyl, OR$_4$, or N(R$_4$)$_2$; and $L_5$ is a 5- or 6-membered aromatic heterocyclic ring containing 1 or 2 nitrogen atoms as part of the ring, said ring optionally substituted with substituents selected from the group consisting of $C_1-C_6$ alkyl and $C_2-C_6$ alkenyl;

and their physiologically acceptable salts; provided that (a) when $R_3$ is CHO, and X and Y are both H, and carbons 7-8 or 8-9 are unsaturated, then $R_1$ is other than OH or OCOCH$_3$, and $R_2$ is other than CH$_3$;

(b) when $R_3$ is CH$_3$ and carbons 7-8 or 8-9 are unsaturated, then $R_1$ is other than OH or OCOCH$_3$, $R_2$ is other than CH$_3$ or H, and X and Y are other than OH, OCOCH$_3$ or H;

(c) when $R_1$ is =O, or is OL$_1$ where $L_1$ is H or $C_1-C_6$ alkyl, or is OCOL$_1$ when $L_1$ is $C_1-C_{20}$ alkyl or phenyl, and X is OR$_4$ or OR$_5$ where $R_4$ is H or OR$_5$ is OCOL$_3$ where $L_3$ is $C_1-C_{20}$ alkyl or phenyl, and Y is H or OH, then $R_3$ is other than H or $\alpha$ $C_1-C_6$ alkyl;

(d) when $R_3$ is CH$_2$OH or CH$_2$OCOH$_3$, and $R_2$ is H or CH$_3$, and carbons 6-7, 7-8 or 8-9 are unsaturated, then $R_1$ is other than =O or OH or OCOCH$_3$, and X is other than H or OH;

(e) when X and Y are both H, then $R_3$ is other than H or CH$_3$;

(f) when X and Y are both H, then $R_3$ is other than OH, and $R_2$ is other than H;

(g) when $R_2$ is H, $R_3$ is $\alpha$ OH, and X is $\beta$ OH, and Y is $\alpha$ H, and carbons 6-7, 7-8, or 8-9 are saturated, then $R_1$ is other than OH;

(h) when X is OH, OR$_5$, N(R$_4$)$_2$, N(R$_5$)$_2$, NR$_4$R$_5$, SR$_5$, NR$_4$OR$_4$, or NR$_4$OR$_5$, then Y is other than Z, OH, OR$_5$, SR$_5$, NR$_4$OR$_4$, NR$_4$OR$_5$, N(R$_4$)$_2$, or N(R$_5$)$_2$; and (i) when R$_3$ is OH, or C$_1$-C$_6$ alkyl, then X and Y, taken together, are other than O.

In the above formulas, the ring structure may be fully saturated, or may be unsaturated between one of carbon positions 6-7, 7-8 or 8-9 or between both carbon positions 6-7 and 8-9. For convenience, the compounds are designated herein as the "d" compound when fully saturated, the "a" compound when unsaturated in the 8-9 position, the "b" compound when unsaturated in the 7-8 position, the "c" compound when unsaturated in the 6-7 position, and the "a/c" compound when unsaturated in both positions 6-7 and 8-9.

As used herein, the substituent designated as "poly-(OR$_4$, OR$_5$, epoxy) C$_1$-C$_6$ alkyl" shall be taken to mean a C$_1$-C$_6$ alkyl chain substituent with one or more of any combination of OR$_4$, OR$_5$ and epoxy.

As used herein, the term "alkyl", employed either alone or in combination with other terms such as "poly-(OR$_4$, OR$_5$, epoxy) C$_1$-C$_6$ alkyl" or "arylalkyl", denotes straight chain or branched alkyl, e.g., methyl, ethyl, n-propyl, isopropyl, and the different butyl, pentyl or hexyl isomers.

As used herein, the term "alkenyl", employed either alone or in combination with other terms, denotes straight chain or branched mono- or poly-unsaturated alkyl, e.g., vinyl, propenyl (allyl), crotyl, isopentenyl, and different butenyl, pentenyl, hexadienyl and hexynyl isomers.

As used herein, the term "alkynyl", employed either alone or in combination with other terms, denotes straight chain or branched mono- or poly-unsaturated alkyl, e.g., ethynyl, propynyl (propargyl), 2-butynyl and other butynyl isomers, and the different pentynyl, hexadiynyl and hexynyl isomers.

As used herein, the term "acyl", employed either alone or in combination with other terms, denotes a carbonyl group attached to an alkyl, alkenyl, alkynyl, arylalkyl or aryl group, e.g., acetate, butyrate, benzoate, and different alkyl, alkenyl, alkynyl, or aryl isomers.

As used herein, the term "halogen" denotes fluorine, chlorine, bromine and iodine.

With respect to the above compositions and method of use formulas, preferred categories of compounds are:

1. Compounds wherein

R$_3$ is H, C$_1$-C$_6$ alkyl, C$_2$-C$_6$ alkenyl, C$_2$-C$_6$ alkynyl, aryl-C$_1$-C$_6$-alkyl, CH$_2$CH$_2$OR$_4$, CHNOR$_4$, CH$_2$SR$_4$, CH$_2$CH$_2$SR$_4$, CHOR$_4$L$_2$, CHOR$_5$L$_2$, CN, CHZ$_2$, CHR$_4$N(R$_4$)$_2$, CH$_2$CH$_2$N(R$_4$)$_2$, CH$_2$CH$_2$Z, N(R$_4$)$_2$, SR$_4$, OR$_4$, poly-(OR$_4$, OR$_5$, epoxy) C$_1$-C$_6$ alkyl, NR$_4$R$_5$, OR$_5$, CH$_2$CH$_2$OR$_5$, CHNOR$_5$, CH$_2$CH$_2$SR$_5$, CH$_2$CH$_2$NR$_4$OR$_4$, CHR$_4$NR$_4$OR$_5$, COL$_3$, C(NR$_4$)L$_2$, CH$_2$CH$_2$NR$_4$OR$_5$, CHR$_4$NR$_4$OR$_4$, CHR$_4$NR$_5$OR$_5$, CH$_4$=CR$_4$C(R$_4$)$_2$Z, CR$_4$=CR$_4$C(R$_4$)$_2$OR$_5$, CR$_4$=CR$_4$C(R$_4$)$_2$OR$_4$, C(O)NR$_4$OR$_4$, C(O)NR$_4$OR$_5$, CR$_4$=CR$_4$R$_5$, C(R$_4$)$_2$OR$_4$, C(R$_4$)$_2$OR$_5$, C(R$_4$)$_2$CR$_4$NOR$_4$ or C(R$_4$)$_2$CR$_4$NOR$_5$.

2. Compounds wherein

R$_3$ is H, C$_1$-C$_6$ alkyl, C$_2$-C$_6$ alkenyl, C$_2$-C$_6$ alkynyl, aryl-C$_1$-C$_6$-alkyl, CH$_2$OR$_4$, CH$_2$CH$_2$OR$_4$, CH$_2$SR$_4$, CH$_2$CH$_2$SR$_4$, CHOR$_4$L$_2$, CHOR$_5$L$_2$, CHZ$_2$, CHR$_4$N(R$_4$)$_2$, CH$_2$CH$_2$N(R$_4$)$_2$, CH$_2$CH$_2$Z, N(R$_4$)$_2$, SR$_4$, OR$_4$, poly-(OR$_4$, OR$_5$, epoxy) C$_1$-C$_6$ alkyl, NR$_4$R$_5$, OR$_5$, CH$_2$CH$_2$OR$_5$, CH$_2$CH$_2$SR$_5$, CH$_2$CH$_2$NR$_4$OR$_4$, CHR$_4$NR$_4$OR$_5$, COL$_3$, C(NR$_4$)L$_2$, CH$_2$CH$_2$NR$_4$OR$_5$, CHR$_4$NR$_4$OR$_4$, CHR$_4$NR$_5$OR$_5$, CR$_4$=CR$_4$C(R$_4$)$_2$Z, CR$_4$=CR$_4$C(R$_4$)$_2$OR$_5$, CR$_4$=CR$_4$C(R$_4$)$_2$OR$_4$, CHO, CR$_4$=CR$_4$R$_5$, C(R$_4$)$_2$OR$_4$, C(R$_4$)$_2$OR$_5$, C(R$_4$)$_2$CR$_4$NOR$_4$ or C(R$_4$)$_2$CR$_4$NOR$_5$.

3. Compounds wherein

R$_3$ is H, C$_1$-C$_6$ alkyl, C$_2$-C$_6$ alkenyl, C$_2$-C$_6$ alkynyl, aryl-C$_1$-C$_6$-alkyl, CH$_2$OR$_4$, CH$_2$CH$_2$OR$_4$, CHNOR$_4$, CH$_2$SR$_4$, CH$_2$CH$_2$SR$_4$, CHOR$_4$L$_2$, CHOR$_5$L$_2$, CN, CHZ$_2$, CHR$_4$N(R$_4$)$_2$, CH$_2$CH$_2$N(R$_4$)$_2$, CH$_2$CH$_2$Z, N(R$_4$)$_2$, SR$_4$, poly-(OR$_4$, OR$_5$, epoxy) C$_1$-C$_6$ alkyl, NR$_4$R$_5$, OR$_5$, CH$_2$CH$_2$OR$_5$, CH$_2$CH$_2$SR$_5$, CH$_2$CH$_2$NR$_4$OR$_4$, CHR$_4$NR$_4$OR$_5$, COL$_3$, C(NR$_4$)L$_2$, CH$_2$CH$_2$NR$_4$OR$_5$, CHR$_4$NR$_4$OR$_4$, CHR$_4$NR$_5$OR$_5$, CR$_4$=CR$_4$C(R$_4$)$_2$Z, CR$_4$=CR$_4$C(R$_4$)$_2$OR$_5$, CR$_4$=CR$_4$C(R$_4$)$_2$OR, C(O)NR$_4$R$_4$, C(O)NR$_4$OR$_5$, CHO, CR$_4$=CR$_4$R$_5$, C(R$_4$)$_2$OR$_4$, C(R$_4$)$_2$OR$_5$, C(R$_4$)$_2$CR$_4$NOR$_4$ or (R$_4$)$_2$CR$_4$NOR$_5$.

4. Compounds wherein

R$_3$ is H, C$_1$-C$_6$ alkyl, C$_2$-C$_6$ alkenyl, C$_2$-C$_6$ alkynyl, aryl-C$_1$-C$_6$-alkyl, CH$_2$CH$_2$OR$_4$, CH$_2$SR$_4$, CH$_2$CH$_2$SR$_4$, CHOR$_4$L$_2$, CHOR$_5$L$_2$, CHZ$_2$, CHR$_4$N(R$_4$)$_2$, CH$_2$CH$_2$N(R$_4$)$_2$, CH$_2$CH$_2$Z, N(R$_4$)$_2$, SR$_4$, poly-(OR$_4$, OR$_5$, epoxy) C$_1$-C$_6$ alkyl, NR$_4$R$_5$, OR$_5$, CH$_2$CH$_2$OR$_5$, CH$_2$CH$_2$SR$_5$, CH$_2$CH$_2$NR$_4$OR$_4$, CHR$_4$NR$_4$OR$_5$, COL$_3$, C(NR$_4$)L$_2$, CH$_2$CH$_2$NR$_4$OR$_5$, CHR$_4$NR$_4$OR$_4$, CHR$_4$NR$_5$OR$_5$, CR$_4$=CR$_4$C(R$_4$)$_2$Z, CR$_4$=CR$_4$C(R$_4$)$_2$OR$_{45}$, CR$_4$=CR$_4$C(R$_4$)$_2$OR$_4$, CR$_4$=CR$_4$R$_5$, C(R$_4$)$_2$OR$_4$, C(R$_4$)$_2$OR$_5$, C(R$_4$)$_2$CR$_4$NOR$_4$ or C(R$_4$)$_2$CR$_4$NOR$_5$.

5. Compounds wherein

X and Y, independently, are H, C$_1$-C$_6$ alkyl, Z, SR$_4$, SR$_5$, N(R$_4$)$_2$, N(R$_5$)$_2$, NR$_4$R$_5$, NR$_4$OR$_4$ or NR$_4$OR$_5$; or X and Y, taken together, are NR$_4$, NR$_5$, NOR$_4$, NOR$_5$, S, C(R$_4$)$_2$, C(R$_5$)$_2$, or CR$_5$R$_4$.

6. Compounds wherein

X and Y, independently, are H, C$_1$-C$_6$ alkyl, OR$_4$, OR$_5$, SR$_4$, SR$_5$, N(R$_4$)$_2$, N(R$_5$)$_2$, NR$_4$R$_5$, NR$_4$OR$_4$ or NR$_4$OR$_5$; or X and Y, taken together, are NR$_4$, NR$_5$, NOR$_4$, NOR$_5$, S, C(R$_4$)$_2$, C(R$_5$)$_2$, CR$_5$R$_4$ or O.

7. Compounds wherein

X and Y, independently, are H, C$_1$-C$_6$ alkyl, Z, OR$_4$, OR$_5$, SR$_4$, SR$_5$, N(R$_4$)$_2$, N(R$_5$)$_2$, NR$_4$R$_5$, NR$_4$OR$_4$ or NR$_4$OR$_5$; or X and Y, taken together, are NR$_4$, NR$_5$, NOR$_5$, S, C(R$_4$)$_2$, C(R$_5$)$_2$, CR$_5$R$_4$ or O.

8. Compounds wherein

X and Y, independently, are H, C$_1$-C$_6$ alkyl, Z, OR$_4$, OR$_5$, SR$_4$, SR$_5$, N(R$_4$)$_2$, N(R$_5$)$_2$, NR$_4$R$_5$, NR$_4$OR$_4$, or NR$_4$OR$_5$; or X and Y, taken together, are NR$_4$, NR$_5$, NOR$_5$, S, C(R$_4$)$_2$, C(R$_5$)$_2$, or CR$_4$R$_5$.

9. Compounds wherein

X and Y, independently, are H, C$_1$-C$_6$ alkyl, SR$_4$, SR$_5$, N(R$_4$)$_2$, N(R$_5$)$_2$, NR$_4$R$_5$, NR$_4$OR$_4$, or NR$_4$OR$_5$; or X and Y, taken together, are NR$_4$, NR$_5$, NOR$_5$, S, C(R$_4$)$_2$, C(R$_5$)$_2$, or CR$_4$R$_5$.

10. Compounds wherein

R$_3$ is H, C$_1$-C$_6$ alkyl, C$_2$-C$_6$ alkenyl, C$_2$-C$_6$ alkynyl, aryl-C$_1$-C$_6$-alkyl, CH$_2$CH$_2$OR$_4$, CH$_2$SR$_4$, $CH_2CH_2SR_4$, $CHOR_4L_2$, $CHOR_5L_2$, $CHZ_2$, $CHR_4N(R_4)_2$, $CH_2CH_2N(R_4)_2$, $CH_2CH_2Z$, $N(R_4)_2$, $SR_4$, poly-$(OR_4, OR_5, $ epoxy$)$ $C_1$-$C_6$ alkyl, $NR_4R_5$, $OR_5$, $CH_2CH_2OR_5$, $CHNOR_5$, $CH_2CH_2SR_5$, $CH_2CH_2NR_4OR_4$, $CHR_4NR_4OR_5$, $COL_3$, $C(NR_4)L_2$, $CH_2CH_2NR_4OR_5$, $CHR_4NR_4OR_4$, $CHR_4NR_5OR_5$, $CR_4=CR_4C(R_4)_2Z$, $CR_4=CR_4C(R_4)_2OR_5$, $CR_4=CR_4C(R_4)_2OR_4$, $Cr_4=CR_4R_5$, $C(R_4)_2OR_4$, $C(R_4)_2OR_5$, $C(R_4)_2CR_4NOR_4$ or $C(R_4)_2 CR_4NOR_5$;

$R_4$ is H, $C_1$-$C_6$ alkyl, $C_2$-$C_6$ alkenyl, aryl, aryl-$C_1$-$C_6$-alkyl or $C_2$-$C_6$ alkynyl;

$R_5$ is $COL_3$;

X and Y, independently, are H, $C_1$-$C_6$ alkyl, $SR_4$, $SR_5$, $N(R_4)_2$, $N(R_5)_2$, $NR_4R_5$, $NR_4OR_4$ or $NR_4OR_5$; or x and Y, taken together, are $NR_4$, $NR_5$, $NOR_5$, S, $C(R_4)_2$, $C(R_5)_2$, or $CR_5R_4$.

11. Compounds wherein $R_1$ is =O, $OL_1$, or $OCOL_1$;

$R_2$ is H, $C_1$-$C_3$ alkyl or $C_2$-$C_4$ alkenyl;

$R_3$ is H, $C_1$-$C_4$ alkyl, $C_2$-$C_4$ alkenyl, $CH_2OR_4$, $CH_2CH_2OR_4$, $CHNOR_4$, $CH_2SR_4$, $CHOR_4L_2$, CN, $CHZ_2$, $CH_2N(R_4)_2$, $CH_2CH_2Z$, $SR_4$, $OR_4$, poly-$(OR_4, OR_5,$ epoxy$)$ $C_1$-$C_4$ alkyl, $NHR_5$, $COL_3$, $C(O)NR_4OR_4$, $C(O)NR_4OR_5$, CHO or $CR_4=CR_4R_5$;

$R_4$ is H, $C_1$-$C_3$ alkyl, $C_2$-$C_3$ alkenyl, aryl, aryl-$C_1$-$C_2$-alkyl or $C_2$-$C_3$ alkynyl;

$R_5$ is $COL_3$;

X and Y, independently, are H, Z, $OR_4$, $N(R_4)_2$; or

X and Y, taken together, are $NOR_4$, or O;

Z is halogen;

$L_1$ is H, $C_1$-$C_6$ alkyl, $C_2$-$C_6$ alkenyl, aryl, aryl-$C_1$-$C_6$-alkyl, or $C_2$-$C_6$ alkynyl;

$L_2$ is $C_1$-$C_3$ alkyl, $C_2$-$C_3$ alkenyl, aryl, aryl-$C_1$-$C_2$-alkyl, or $C_2$-$C_3$ alkynyl;

$L_3$ is $C_1$-$C_2$ alkyl, $C_2$-$C_3$ alkenyl, aryl, aryl-$C_1$-$C_2$-alkyl, $C_2$-$C_3$ alkynyl, $OR_4$, or $N(R_4)_2$.

12. Compounds wherein $R_1$ is =O, $OL_1$, or $OCOL_1$;

$R_2$ is H, $C_1$-$C_3$ alkyl or $C_2$-$C_3$ alkenyl; $R_3$ is H, $C_1$-$C_4$ alkyl, $C_2$-$C_4$ alkenyl, $CH_2CH_2OR_4$, $CHNOR_4$, $CH_2SR_4$, $CHOR_4L_2$, CN, $CHZ_2$, $CH_2N(R_4)_2$, $CH_2CH_2Z$, $SR_4$, $OR_4$, poly-$(OR_4, OR_5,$ epoxy$)$ $C_1$-$C_4$ alkyl, $NHR_5$, $COL_3$, $C(O)NR_4OR_4$, $C(O)NR_4OR_5$, or $CR_4=CF_4R_5$;

$R_4$ is H, $C_1$-$C_3$ alkyl, $C_2$-$C_3$ alkenyl, aryl, aryl-$C_1$-$C_2$-alkyl or $C_2$-$C_3$ alkynyl;

$R_5$ is $COL_3$;

X and Y, independently, are H, Z, $OR_4$, $N(R_4)_2$; or

X and Y, taken together, are $NOR_4$, or O;

Z is halogen;

$L_1$ is H, $C_1$-$C_6$ alkyl, $C_2$-$C_6$ alkenyl, aryl, aryl-$C_1$-$C_6$-alkyl, or $C_2$-$C_6$ alkynyl;

$L_2$ is $C_1$-$C_3$ alkyl, $C_2$-$C_3$ alkenyl, aryl, aryl-$C_1$-$C_2$-alkyl, or $C_2$-$C_3$ alkynyl;

$L_3$ is $C_1$-$C_2$ alkyl, $C_2$-$C_3$ alkenyl, aryl, aryl-$C_1$-$C_2$-alkyl, $C_2$-$C_3$ alkynyl, $OR_4$, or $N(R_4)_2$.

13. Compounds wherein $R_1$ is =O, $OL_1$, or $OCOL_1$;

$R_2$ is H, $C_1$-$C_3$ alkyl or $C_2$-$C_3$ alkenyl;

$R_3$ is H, $C_1$-$C_4$ alkyl, $C_2$-$C_4$ alkenyl, $CH_2OR_4$, $CH_2CH_2OR_4$, $CH_2SR_4$, $CHOR_4L_2$, $CHZ_2$, $CH_2N(R_4)_2$, $CH_2CH_2Z$, $SR_4$, $OR_4$, poly-$(OR_4, OR_5,$ epoxy$)$ $C_1$-$C_4$ alkyl, $NHR_5$, $COL_3$, CHO or $CR_4=CF_4R_5$;

$R_4$ is H, $C_1$-$C_3$ alkyl, $C_2$-$C_3$ alkenyl, aryl, aryl-$C_1$-$C_2$-alkyl or $C_2$-$C_3$ alkynyl;

$R_5$ is $COL_3$;

X and Y, independently, are H, Z, $OR_4$, $N(R_4)_2$; or

X and Y, taken together, are $NOR_4$, or O;

Z is halogen;

$L_1$ is H, $C_1$-$C_6$ alkyl, $C_2$-$C_6$ alkenyl, aryl, aryl-$C_1$-$C_6$-alkyl, or $C_2$-$C_6$ alkynyl;

$L_2$ is $C_1$-$C_3$ alkyl, $C_2$-$C_3$ alkenyl, aryl, aryl-$C_1$-$C_2$-alkyl, or $C_2$-$C_3$ alkynyl;

$L_3$ is $C_1$-$C_2$ alkyl, $C_2$-$C_3$ alkenyl, aryl, aryl-$C_1$-$C_2$-alkyl, $C_2$-$C_3$ alkynyl, $OR_4$, or $N(R_4)_2$.

14. Compounds wherein $R_1$ is =O, $OL_1$, or $OCOL_1$;

$R_2$ is H, $C_1$-$C_3$ alkyl or $C_2$-$C_3$ alkenyl;

$R_3$ is H, $C_1$-$C_4$ alkyl, $C_2$-$C_4$ alkenyl, $CH_2OR_4$, $CH_2CH_2OR_4$, $CHNOR_4$, $CH_2SR_4$, $CHOR_4L_2$, CN, $CHZ_2$, $CH_2N(R_4)_2$, $CH_2CH_2Z$, $SR_4$, poly-$(OR_4, OR_5,$ epoxy$)$ $C_1$-$C_4$ alkyl, $NHR_5$, $COL_3$, $C(O)NR_4OR_4$, $C(O)NR_4OR_5$, CHO or $CR_4=CF_4R_5$;

$R_4$ is H, $C_1$-$C_3$ alkyl, $C_2$-$C_3$ alkenyl, aryl, aryl-$C_1$-$C_2$-alkyl or $C_2$-$C_3$ alkynyl;

$R_5$ is $COL_3$;

X and Y, independently, are H, Z, $OR_4$, $N(R_4)_2$; or

X and Y, taken together, are $NOR_4$, or O;

Z is halogen;

$L_1$ is H, $C_1$-$C_6$ alkyl, $C_2$-$C_6$ alkenyl, aryl, aryl-$C_1$-$C_6$-alkyl, or $C_2$-$C_6$ alkynyl;

$L_2$ is $C_1$-$C_3$ alkyl, $C_2$-$C_3$ alkenyl, aryl, aryl-$C_1$-$C_2$-alkyl, or $C_2$-$C_3$ alkynyl;

$L_3$ is $C_1$-$C_2$ alkyl, $C_2$-$C_4$ alkenyl, aryl, aryl-$C_1$-$C_2$-alkyl, $C_2$-$C_3$ alkynyl, $OR_4$, or $N(R_4)_2$.

15. Compounds wherein $R_1$ is =O, $OL_1$, or $OCOL_1$;

$R_2$ is H, $C_1$-$C_3$ alkyl or $C_2$-$C_3$ alkenyl;

$R_3$ is H, $C_1$-$C_4$ alkyl, $C_2$-$C_4$ alkenyl, $CH_2CH_2OR_4$, $CH_2SR_4$, $CHOR_4L_2$, $CHZ_2$, $CH_2N(R_4)_2$, $CH_2CH_2Z$, $SR_4$, poly-$(OR_4, OR_5,$ epoxy$)$ $C_1$-$C_4$ alkyl, $NHR_5$, $COL_3$, or $CR_4=CF_4R_5$;

$R_4$ is H, $C_1$-$C_3$ alkyl, $C_2$-$C_3$ alkenyl, aryl, aryl-$C_1$-$C_2$-alkyl or $C_2$-$C_3$ alkynyl;

$R_5$ is $COL_3$;

X and Y, independently, are H, Z, $OR_4$, $N(R_4)_2$; or

X and Y, taken together, are $NOR_4$, or O;

Z is halogen;

$L_1$ is H, $C_1$-$C_6$ alkyl, $C_2$-$C_6$ alkenyl, aryl, aryl-$C_1$-$C_6$-alkyl, or $C_2$-$C_6$ alkynyl;

$L_2$ is $C_1$-$C_3$ alkyl, $C_2$-$C_3$ alkenyl, aryl, aryl-$C_1$-$C_2$-alkyl, or $C_2$-$C_3$ alkynyl;

$L_3$ is $C_1$-$C_2$ alkyl, $C_2$-$C_3$ alkenyl, aryl, aryl-$C_1$-$C_2$-alkyl, $C_2$-$C_3$ alkynyl, $OR_4$, or $N(R_4)_2$.

16. Compounds wherein $R_1$ is =O, $OL_1$, or $OCOL_1$;

$R_2$ is H, $C_1$-$C_3$ alkyl or $C_2$-$C_3$ alkenyl;

$R_3$ is H, $C_1$-$C_4$ alkyl, $C_2$-$C_4$ alkenyl, $CH_2OR_4$, $CH_2CH_2OR_4$, $CHNOR_4$, $CH_2SR_4$, $CHOR_4L_2$, CN, $CHZ_2$, $CH_2N(R_4)_2$, $CH_2CH_2Z$, $SR_4$, $OR_4$, poly-$(OR_4, OR_5,$ epoxy$)$ $C_1$-$C_4$ alkyl, $NHR_5$, $COL_3$, $C(O)NR_4OR_4$, $C(O)NR_4OR_5$, CHO or $CR_4=CF_4R_5$;

$R_4$ is H, $C_1$-$C_3$ alkyl, $C_2$-$C_3$ alkenyl, aryl, aryl-$C_1$-$C_2$-alkyl or $C_2$-$C_3$ alkynyl;

$R_5$ is $COL_3$;

X and Y, independently, are H, Z, $N(R_4)_2$; or

X and Y, taken together, are $NOR_4$;

Z is halogen;

$L_1$ is H, $C_1$-$C_6$ alkyl, $C_2$-$C_6$ alkenyl, aryl, aryl-$C_1$-$C_6$-alkyl, or $C_2$-$C_6$ alkynyl;

$L_2$ is $C_1$-$C_3$ alkyl, $C_2$-$C_3$ alkenyl, aryl, aryl-$C_1$-$C_2$-alkyl, or $C_2$-$C_3$ alkynyl;

$L_3$ is $C_1$-$C_2$ alkyl, $C_2$-$C_3$ alkenyl, aryl, aryl-$C_1$-$C_2$-alkyl, $C_2$-$C_3$ alkynyl, $OR_4$, or $N(R_4)_2$.

17. Compounds wherein $R_1$ is =O, $OL_1$, or $OCOL_1$;

$R_2$ is H, $C_1$-$C_3$ alkyl or $C_2$-$C_3$ alkenyl;

$R_3$ is H, $C_1$-$C_4$ alkyl, $C_2$-$C_4$ alkenyl, $CH_2OR_4$, $CH_2CH_2OR_4$, $CHNOR_4$, $CH_2SR_4$, $CHOR_4L_2$, CN, $CHZ_2$, $CH_2N(R_4)_2$, $CH_2CH_2Z$, $SR_4$, $OR_4$, poly-($OR_4$, $OR_5$, epoxy) $C_1$-$C_4$ alkyl, $NHR_5$, $COL_3$, $C(O)NR_4OR_4$, $C(O)NR_4OR_5$, CHO or $CR_4$=$CF_4R_5$;

$R_4$ is H, $C_1$-$C_3$ alkyl, $C_2$-$C_3$ alkenyl, aryl, aryl-$C_1$-$C_2$-alkyl or $C_2$-$C_3$ alkynyl;

$R_5$ is $COL_3$;

X and Y, independently, are H, $OR_4$, $N(R_4)_2$; or

X and Y, taken together, are $NOR_4$, or O;

Z is halogen;

$L_1$ is H, $C_1$-$C_6$ alkyl, $C_2$-$C_6$ alkenyl, aryl, aryl-$C_1$-$C_6$-alkyl, or $C_2$-$C_6$ alkynyl;

$L_2$ is $C_1$-$C_3$ alkyl, $C_2$-$C_3$ alkenyl, aryl, aryl-$C_1$-$C_2$-alkyl, or $C_2$-$C_3$ alkynyl;

$L_3$ is $C_1$-$C_2$ alkyl, $C_2$-$C_3$ alkenyl, aryl, aryl-$C_1$-$C_2$-alkyl, $C_2$-$C_3$ alkynyl, $OR_4$, or $N(R_4)_2$.

18. Compounds wherein $R_1$ is =O, $OL_1$, or $OCOL_1$;

$R_2$ is H, $C_1$-$C_3$ alkyl or $C_2$-$C_3$ alkenyl;

$R_3$ is H, $C_1$-$C_4$ alkyl, $C_2$-$C_4$ alkenyl, $CH_2OR_4$, $CH_2CH_2OR_4$, $CHNOR_4$, $CH_2SR_4$, $CHOR_4L_2$, CN, $CHZ_2$, $CH_2N(R_4)_2$, $CH_2CH_2Z$, $SR_4$, $OR_4$, poly-($OR_4$, $OR_5$, epoxy) $C_1$-$C_4$ alkyl, $NHR_5$, $COL_3$, $C(O)NR_4OR_4$, $C(O)NR_4OR_5$, CHO or $CR_4$=$CF_4R_5$;

$R_4$ is H, $C_1$-$C_3$ alkyl, $C_2$-$C_3$ alkenyl, aryl, aryl-$C_1$-$C_2$-alkyl or $C_2$-$C_3$ alkynyl;

$R_5$ is $COL_3$;

X and Y, independently, are H, Z, $OR_4$, $N(R_4)_2$; or

X and Y, taken together, is $NOR_4$;

Z is halogen;

$L_1$ is H, $C_1$-$C_6$ alkyl, $C_2$-$C_6$ alkenyl, aryl, aryl-$C_1$-$C_6$-alkyl, or $C_2$-$C_6$ alkynyl;

$L_2$ is $C_1$-$C_3$ alkyl, $C_2$-$C_3$ alkenyl, aryl, aryl-$C_1$-$C_2$-alkyl, or $C_2$-$C_3$ alkynyl;

$L_3$ is $C_1$-$C_2$ alkyl, $C_2$-$C_3$ alkenyl, aryl, aryl-$C_1$-$C_2$-alkyl, $C_2$-$C_3$ alkynyl, $OR_4$, or $N(R_4)_2$.

19. Compounds wherein $R_1$ is =O, $OL_1$, or $OCOL_1$;

$R_2$ is H, $C_1$-$C_3$ alkyl or $C_2$-$C_3$ alkenyl;

$R_3$ is H, $C_1$-$C_4$ alkyl, $C_2$-$C_4$ alkenyl, $CH_2OR_4$, $CH_2CH_2OR_4$, $CHNOR_4$, $CH_2SR_4$, $CHOR_4L_2$, CN, $CHZ_2$, $CH_2N(R_4)_2$, $CH_2CH_2Z$, $SR_4$, $OR_4$, poly-($OR_4$, $OR_5$, epoxy) $C_1$-$C_4$ alkyl, $NHR_5$, $COL_3$, $C(O)NR_4OR_4$, $C(O)NR_4OR_5$, CHO or $CR_4$=$CF_4R_5$;

$R_4$ is H, $C_1$-$C_3$ alkyl, $C_2$-$C_3$ alkenyl, aryl, aryl-$C_1$-$C_2$-alkyl or $C_2$-$C_3$ alkynyl;

$R_5$ is $COL_3$;

X and Y, independently, are H, $N(R_4)_2$; or

X and Y, taken together, are $NOR_4$;

Z is halogen;

$L_1$ is H, $C_1$-$C_6$ alkyl, $C_2$-$C_6$ alkenyl, aryl, aryl-$C_1$-$C_6$-alkyl, or $C_2$-$C_6$ alkynyl;

$L_2$ is $C_1$-$C_3$ alkyl, $C_2$-$C_3$ alkenyl, aryl, aryl-$C_1$-$C_2$-alkyl, or $C_2$-$C_3$ alkynyl;

$L_3$ is $C_1$-$C_2$ alkyl, $C_2$-$C_3$ alkenyl, aryl, aryl-$C_1$-$C_2$-alkyl, $C_2$-$C_3$ alkynyl, $OR_4$, or $N(R_4)_2$.

20. Compounds wherein $R_1$ is =O, $OL_1$, or $OCOL_1$;

$R_2$ is H, $C_1$-$C_3$ alkyl or $C_2$-$C_3$ alkenyl;

$R_3$ is H, $C_1$-$C_4$ alkyl, $C_2$-$C_4$ alkenyl, $CH_2CH_2OR_4$, $CH_2SR_4$, $CHOR_4L_2$, $CHZ_2$, $CH_2N(R_4)_2$, $CH_2CH_2Z$, $SR_4$, poly-($OR_4$, $OR_5$, epoxy) $C_1$-$C_4$ alkyl, $NHR_5$, $COL_3$, CHO or $CR_4$=$CF_4R_5$;

$R_4$ is H, $C_1$-$C_3$ alkyl, $C_2$-$C_3$ alkenyl, aryl, aryl-$C_1$-$C_2$-alkyl or $C_2$-$C_3$ alkynyl;

$R_5$ is $COL_3$;

X and Y, independently, are H, $N(R_4)_2$; or

X and Y, taken together, are $NOR_4$;

Z is halogen;

$L_1$ is H, $C_1$-$C_6$ alkyl, $C_2$-$C_6$ alkenyl, aryl, aryl-$C_1$-$C_6$-alkyl, or $C_2$-$C_6$ alkynyl;

$L_2$ is $C_1$-$C_3$ alkyl, $C_2$-$C_3$ alkenyl, aryl, aryl-$C_1$-$C_2$-alkyl, or $C_2$-$C_3$ alkynyl;

$L_3$ is $C_1$-$C_2$ alkyl, $C_2$-$C_3$ alkenyl, aryl, aryl-$C_1$-$C_2$-alkyl, $C_2$-$C_3$ alkynyl, $OR_4$, or $N(R_4)_2$.

Compounds wherein $R_1$ is OH, $OCOCH_3$ or OCOPh;

$R_2$ is H or $CH_3$;

$R_3$ is H, $CH_3$, CH=$CH_2$, $CH_2CH$=$CH_2$, $CH_2OH$, $CH_2CH_2CH$, CHNOH, $CH_2SCH_3$, SCHOHCH=$CH_2$, CHOHC≡CH, CN, $CHF_2$, $CH_2CH_2Br$, $SCH_3$, OH, $CHOHCH_2OH$, CHOH-$CHOHCH_2OH$, $$\text{CHOHCH}\underset{O}{\overset{}{\diagdown\diagup}}\text{CH}_2, \quad \text{CH}\underset{O}{\overset{}{\diagdown\diagup}}\text{CH}_2,$$

NHCHO, COCH=$CH_2$, $CO_2H$, $CONH_2$, CONHOH, CHO, $CO_2CH_3$ or CH=$CHCO_2CH_3$; and X and Y, independently, are H, F, OH or $NH_2$; or X and Y, together, are NOH or O.

22. Compounds wherein $R_1$ is Oh or $OCOCH_3$;

$R_2$ is H or $CH_3$;

$R_3$ is H, $CH_3$, CH=$CH_2$, $CH_2CH$=$CH_2$, $CH_2CH_2CH$, CHNOH, $CH_2SCH_3$, CHOHCH=$CH_2$, CHOHC≡CH, CN, $CHF_2$, $CH_2CH_2Br$, $SCH_3$, OH, $CHOHCH_2OH$, CHOH-$CHOHCH_2OH$, $$\text{CHOHCH}\underset{O}{\overset{}{\diagdown\diagup}}\text{CH}_2,$$

NHCHO, COCH=$CH_2$, $CO_2H$, $CONH_2$, CONHOH, $CO_2CH_3$ or CH=$CHCO_2CH_3$; and X and Y, independently, are H, F, OH or $NH_2$; or X and Y, together, are NOH or O.

23. Compounds wherein $R_1$ is OH;

$R_2$ is H or $CH_3$;

$R_3$ is $CH_3$, CH=$CH_2$, $CH_2CH$=$CH_2$, $CH_2CH_2CH$, $CH_2SCH_3$, CHOHCH=$CH_2$, CHOHC≡CH, $CHF_2$, $CH_2CH_2Br$, $SCH_3$, OH, $CHOHCH_2OH$, $CHOHCHOHCH_2OH$, $$\text{CHOHCH}\underset{O}{\overset{}{\diagdown\diagup}}\text{CH}_2,$$

NHCHO, COCH=CH$_2$, CO$_2$H, CONH$_2$, CO$_2$CH$_3$ or CH=CHCO$_2$CH$_3$; and

X and Y, independently, are H, F, OH or NH$_2$; or

X and Y, together, are NOH or O.

24. Compounds wherein

R$_1$ is OH;

R$_2$ is H or CH$_3$;

R$_3$ is CH$_3$, CH=CH$_2$, CH$_2$CH=CH$_2$, CH$_2$CH$_2$CH, CHNOH, CH$_2$SCH$_3$, CHOHCH=CH$_2$, CHOHC≡CH, CN, CHF$_2$, CH$_2$CH$_2$Br, SCH$_3$, CHOHCH$_2$OH, CHOHCHOHCH$_2$OH,

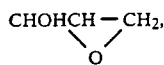

CH-CH$_2$, NHCHO, COCH=CH$_2$, CO$_2$H, CONH$_2$, CONHOH, CO$_2$CH$_3$ or CH=CHCO$_2$CH$_3$; and X and Y, independently, are H, F, OH or NH$_2$; or X and Y, together, are NOH or O.

25. Compounds wherein

R$_1$ is OH;

R$_2$ is H or CH$_3$;

R$_3$ is H, CH$_3$, CH=CH$_2$, CH$_2$CH=CH$_2$, CH$_2$OH, CH$_2$CH$_2$CH, CHNOH, CH$_2$SCH$_3$, CHOHCH=CH$_2$, CHOHC≡CH, CN, CHF$_2$, CH$_2$CH$_2$Br, SCH$_3$, OH, CHOHCH$_2$OH, CHOHCH$_2$OH,

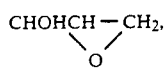

NHCHO, COCH=CH$_2$, CO$_2$H, CONH$_2$, CONHOH, CHO, CO$_2$CH$_3$ or CH=CHCO$_2$CH$_3$; and X and Y, independently, are H or F; or X and Y, together, are NOH.

26. Compounds wherein

R$_1$ is OH;

R$_2$ is H or CH$_3$;

R$_3$ is H, CH$_3$, CH=CH$_2$, CH$_2$CH=CH$_2$, CH$_2$OH, CH$_2$CH$_2$CH, CHNOH, CH$_2$SCH$_3$, CHOHCH=CH$_2$, CHOHC≡CH, CN, CHF$_2$, CH$_2$CH$_2$Br, SCH$_3$, OH, CHOHCH$_2$OH, CHOHCH$_2$OH,

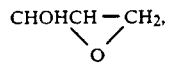

NHCHO, COCH=CHY$_2$, CO$_2$H, CONH$_2$, CONHOH, CHO, CO$_2$CH$_3$ or CH=CHCO$_2$CH$_3$; and X and Y, independently, are H, or OH; or X and Y, together, are NOH or O.

27. Compounds wherein

R$_1$ is OH;

R$_2$ is H or CH$_3$;

R$_3$ is H, CH$_3$, CH=CH$_2$, CH$_2$CH=CH$_2$, CH$_2$OH, CH$_2$CH$_2$CH, CHNOH, CH$_2$SCH$_3$, CHOHCH=CH$_2$, CHOHC≡CH, CN, CHF$_2$, CH$_2$CH$_2$Br, SCH$_3$, OH, CHOHCH$_2$OH, CHOHCH$_2$OH,

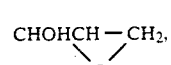

NHCHO, COCH=CH$_2$, CO$_2$H, CONH$_2$, CONHOH, CHO, CO$_2$CH$_3$ or CH=CHCO$_2$CH$_3$; and X and Y, independently, are H; or X and Y, together, are NOH.

28. Compounds wherein

R$_1$ is OH;

R$_2$ is H or CH$_3$;

R$_3$ is CH$_3$, CH=CH$_2$, CH$_2$CH=CH$_2$, CH$_2$CH$_2$CH, CH$_2$SCH$_3$, CHOHCH=CH$_2$, CHOHC≡CH, CHF$_2$, CH$_2$CH$_2$Br, SCH$_3$, CHOHCH$_2$OH, CHOHCHOHCH$_2$OH,

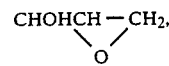

NHCHO, COCH=CH$_2$, CO$_2$H, CONH$_2$, CONHOH, CHO, CO$_2$CH$_3$ or CH=CHCO$_2$CH$_3$; and X and Y, independently, are H; or X and Y, together, are NOH.

29. Compounds wherein

R$_1$ is OH;

R$_2$ is H or CH$_3$;

R$_3$ is CH$_3$, CH$_2$CH=CH$_2$, CHNOH, CN, or CHF$_2$, ; and

X and Y, independently, are H, F, OH or NH$_2$; or

X and Y, together, are NOH.

30. Compounds wherein

R$_1$ is OH;

R$_2$ is H or CH$_3$;

R$_3$ is CH$_3$, CH=CH$_2$, CH$_2$OH, CH$_2$SCH$_3$, CHOHCH=CH$_2$, CHOHC≡CH, SCH$_3$, OH, CHOHCH$_2$OH, COCH=CH$_2$, CO$_2$H, CONH$_2$, or CONHOH; and X and Y, independently, are H, OH; or X and Y, together, are NOH or O.

31. Compounds wherein

R$_1$ is OH;

R$_2$ is H or CH$_3$;

R$_3$ is CH$_3$, CH=CH$_2$, CH$_2$OH, CH$_2$SCH$_3$, CHOHCH=CH$_2$, CHOHC≡CH, SCH$_3$, COCH=CH$_2$, CO$_2$H or CONH$_2$; and X and Y, independently, are H, or OH; or X and Y, together, are NOH or O.

Many of the above compounds are preferable for reasons of increased ease of synthesis and/or greater efficacy.

Specifically preferred for reasons of greatest ease of synthesis and/or greatest efficacy are:

32,32-difluoro-lanost-8-en-3β-ol;
32,32-difluoro-lanost-7-en-3β-ol;
4,4-dimethyl-14α-(1'-hydroxy-2'-propenyl)-5α-cholest-8-en-3β-ol;
14α-allyl-4,4-dimethyl-5α-cholest-8-en-3β-ol-15-oxime;
lanost-8-en-32-aldoxime-3β-ol;
lanost-7-en-32-aldoxime-3β-ol;
14α-cyano-4,4-dimethyl-5α-cholest-8-en-3β-ol;
15α-fluoro-lanost-7-en-3β-ol;
15α-fluoro-14α-methyl-5α-cholest-7-en-3β-ol;
3β-hydroxy-lanost-8-en-15-oxime;
3β-hydroxy-lanost-7-en-15-oxime;
4,4-dimethyl-5α-cholest-8-en-3β,14α,15α-triol;
5α-cholest-8-en-3β,14α,15α-triol;
3β-hydroxy-lanost-8-en-32-ohydroxamic acid;
3β, 15α-dihydroxy-lanost-8-en-32-al;
3β-hydroxy-lanost-8-en-32-aldoxime-15-oxime;
3β-acetoxy-lanost-8-en-32-alkoxime;
3β-acetoxy-lanost-7-en-15-oxime;

lanost-6-en-32-aldoxime-3β-ol;
15α-amino-lanost-8-en-3β-ol;
14α-amino-4,4-dimethyl-5α-cholest-8-en-3β-ol;
4,4-dimethyl-14α-(N-formyl-amino)-5α-cholest-8-en-3β-ol;
4,4-dimethyl-14α-(N-ethoxycarbonylamino)-5α-cholest-8-en-3β-ol; and
32-ethynyl-lanost-8-ene-3β,32-diol.
lanost-8-ene-3β,15αm32-triol
4,4-dimethyl-14α-vinyl-5α-cholest-8-en-3β-ol
3β-hydroxy-lanost-8-ene-32-carboxylic acid
3β-hydroxy-lanost-8-ene-32-carobxamide
3β-hydroxy-32-vinyl-lanost-8-en-32-on
32-hydroxymethyl-lanost-8-en-3β-ol
32-hydroxymethyl-lanost-8-ene-3β,32-diol
15α-fluoro-32-vinyl-lanost-7-en-3β-ol
4,4-dimethyl-3β-hydroxy-14α-methylthio-5α-cholest-8-en-15-on
3β-hydroxy-32-methylthio-lanost-8-en-15-on
32-ethyl-3β-hydroxy-lanost-8-en-15-oxime
14α(1'-hydroxy-2'-propenyl)-5α-cholest-8-en-3β-ol
3β-hydroxy-14α-methyl-5α-cholest-8-en-15-oxime.

DETAILED DESCRIPTION OF THE INVENTION

The compounds of the above formulas can be employed to inhibit lanosta-8,24-dien-3β-ol 14α-methyldemethylase activity, suppress HMGR activity, decrease cholesterol formation and lower serum cholesterol levels in mammals. These compounds can be administered alone, or in combination with pharmaceutically acceptable carriers or diluents appropriate to the indicated route of administration. Administration can be oral, sublingual, buccal, topical and parenteral such as intravenous, subcutaneous or intramuscular. Acceptable carriers and diluents are well-known in the pharmaceutical art, and are described, for example, in Remington's Pharmaceutical Sciences, Gennaro, A. R., ed., Mack Publishing Co., Easton, Pa. (1985). The useful dosage to be administered and the mode of administration will vary depending upon the age, weight and species of mammal treated.

Briefly, the mechanisms by which the active 14,15-substituted lanosterol compounds of the present invention are believed to function is as follows. First, the observed decrease in HMGR activity is thought to occur as a result of a decreased synthesis of HMGR protein and/or an enhanced rate of HMGR degradation (collectively termed herein as "suppression"). The observed decrease in lanosta-8,24-dien-3β-ol 14α-methyl demethylase activity is thought to occur as a result of a direct action of the compounds on the demethylase enzyme (termed herein as "inhibition"). The inhibition of lanosta-8,24-dien-3β-ol 14α-methyl demethylase activity is also thought to result in the production of molecules which in turn act as suppression of HMGR activity as described above. These actions in turn are thought to collectively result in a decrease in cholesterol synthesis and a reduction in serum cholesterol levels.

General Procedure for the Preparation of Unsaturated 14,15-Substituted Lanosterols The compounds of the present invention accomodate the necessary requirements for lanosta-8,24-dien-3β-ol 14α-methyl demethylase inhibition and suppression of HMGR activity. To prepare these compounds a three-prong synthetic approach was employed, i.e., monosubstitution at the 14- or 15-position and disubstitution at the 14- and 15-positions.

The following functional group transformations can be performed by one skilled in the art: (1) enolate formation of a ketone with a suitable base followed by alkylation of the enolate anion with an alkylating agent (2) acylation of alcohols with a suitable acylating reagent giving rise to the esters under standard conditions, (3) the reduction of oximes to amines and hydroxylamines with a suitable reducing agent, (4) the reduction of amides to amines with a suitable reducing agent and the subsequent acylation of the resultant amine with a standard acylating reagent, (5) displacement of a halide or equivalent by using the appropriate amine, alcohol or thiol reagent, (6) the synthesis of amines via reactions of the appropriate aldehyde or ketone with an amine under dehydration conditions, (7) the synthesis of olefins by reacting the appropriate ketone or aldehyde with the appropriate Wittig reagent or equivalent, (8) the synthesis of thiones by reacting the corresponding ketone with an appropriate thiolating reagent.

14-Monosubstitution (SCHEMES I-V)

Introduction of the appropriate substituent at the 14α-position required the elaboration of lanosta-8,24-dien-3β-ol (SCHEME I, Compound 1) into the protected 3β-hydroxy-14α-hydroxymethyl-dihydro-lanosterol (Compound 6).

SCHEME I

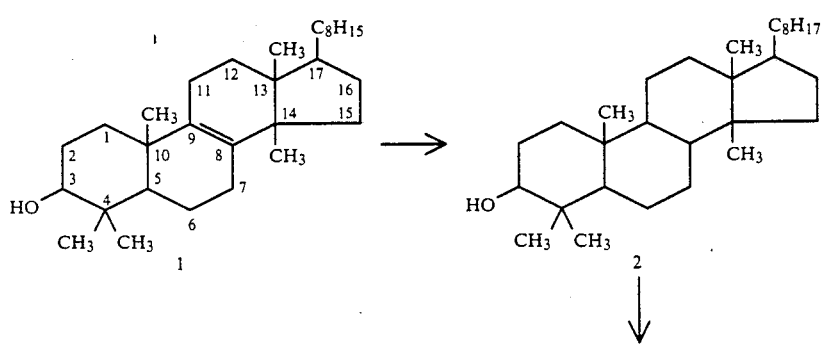

SCHEME I

-continued

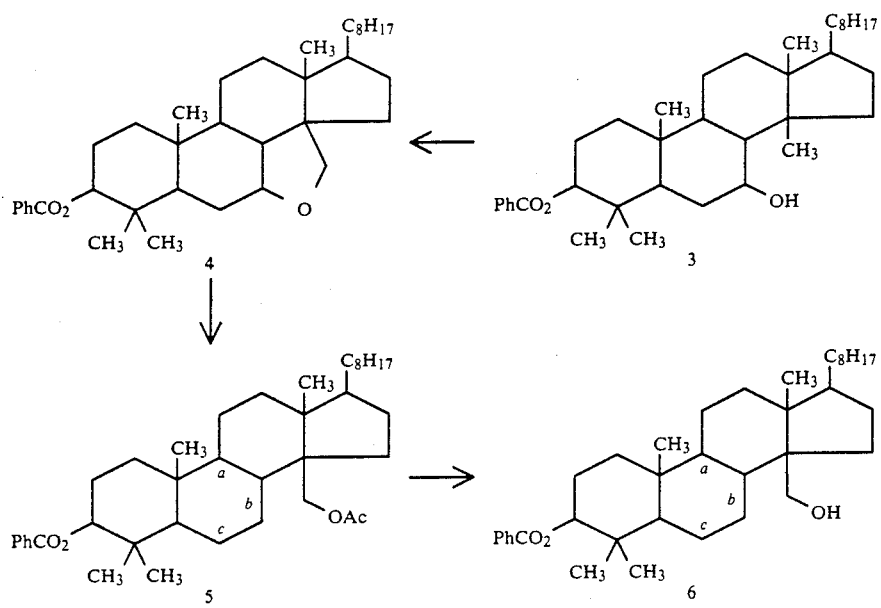

Transformation of the commercially available lanosta-8,24-dien-3β-ol (obtained from Sigma Chemical Co., P.O. Box 14508, St. Louis, Mo. 63178) to the diol (Compound 2) was achieved using the procedure described in Parish et al., J. Lipid Res., 22:859-868 (1981). To utilize this intermediate in our studies, a novel synthetic route that allows selective protection of the 3β-hydroxy group while the 14α-hydroxymethyl group is free for elaboration was employed. Taking advantage of the sterically encumbered secondary alcohol at the 7α-position, the diol (Compound 2) was treated with freshly distilled benzoyl chloride in dry pyridine (obtained from aldrich Chemical Co., Inc., 940 West St. Paul Ave., Milwaukee, Wis. 53233) at 40° C. for 25 min. the reaction resulted, after silica gel chromatography, in the recovery of 3β-benzoate (compound 3) in a 48% yield. Using the directing effects of the 7α-hydroxyl group, the resulting Compound 3 was oxidized in refluxing benzene under a nitrogen atmosphere by means of recrystallized (from acetic acid) lead tetraacetate (obtained from Aldrich) treatment. After 17 hrs of refluxing followed by silica gel chromatography, the desired furan, Compound 4, was obtained in a yield of 70%. furan ring cleavage of Compound 4 was achieved by exposing 4 to excess pyridine hydrochloride (obtained from Fluka A.G., Buchs, Switzerland) in refluxing acetic anhydride for 18 hrs under an atmosphere of nitrogen. Three olefin isomers of the newly generated acetate Compound 5 (compounds 5a, 5b and 5c) were obtained in an overall 60% yield.

Separation of the isomers by silica gel chromatography (MPLC) provided 5c (16%) yield, and separation by high pressure liquid chromatography (HPLC) afforded 5a (19% yield) and 5b (27% yield). With all three olefinic isomers separated, the final selective hydrolysis was achieved by treatment of 5a with ethanolic potassium hydroxide for 2 hrs at 10° C. to generate Compound 6a in 68% yield. In the same manner, both Compounds 6b (73% yield) and 6c (62% yield) were also obtained, providing entry into the double bond isomers of the 14α-substituted series.

Following preparation of the critical monoprotected diol, Compound 6, the next goal is the elaboration of that compound into the desired 14α-substituted dihydrolanosterols. This is shown in SCHEME II.

SCHEME II

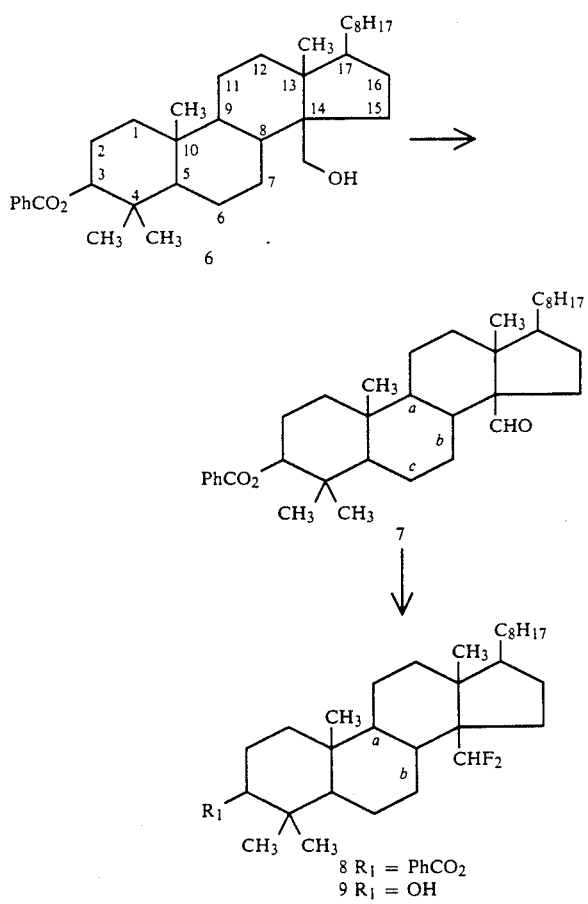

Oxidation of the 14α-hydroxymethyl group to the 14α-carboxaldehyde Compound 7a was achieved in a 93% yield by treating Compound 6a with Jones reagent (prepared as described in Meinwald et al., Org. Syn., 45:77-79 (1965)) at −10° C. for 15 min. Compound 7a was then recovered using medium pressure silica gel chromatography (MPLC). In the same manner Compound 7b was prepared in 85% yield. The 14α-carboxyaldehyde Compound 7c was prepared in a 60% yield by treatment at room temperature of a dichromate (Aldrich) and powdered 4A molecular sieves (Aldrich) followed by silica gel purification on MPLC.

Exposing the azeotropically (benzene) dried aldehyde Compound 7a to neat DAST (diethylamino sulfur trifluoride, Aldrich) under an argon atmosphere for 4.5 hr at 80° C. afforded the 14α-difluoromethyl dihydrolanosterol, Compound 8a, in a 76% yield. In the same manner, Compound 8b was prepared from Compound 7b in a 48% yield. An anhydrous (distilled over benzophenone and sodium) diethyl ether solution of Compound 8a was exposed to lithium aluminum hydride (obtained from Alfa Prod., Danver, Mass.) at room temperature for 20 min. resulting in the desired 3β-hydroxy-14α-difluoromethyl dihydrolanosterol, Compound 9a, in an 86% yield. The difluoride, Compound 9a, along with another olefin isomer Compound 9b prepared in a similar fashion in an 86% yield constitute two examples of 14α-substituted lanosterols within the scope of the present invention.

Further elaboration of the 14α-position (SCHEME III) was achieved by treating the hydroxy aldehyde Compound 10 (prepared as described by Shafiee et al., J. Lipid Res., 27:1–10 (1986)) with a variety of alkyl and alkenyl anions (Grignards, lithium reagents).

SCHEME III

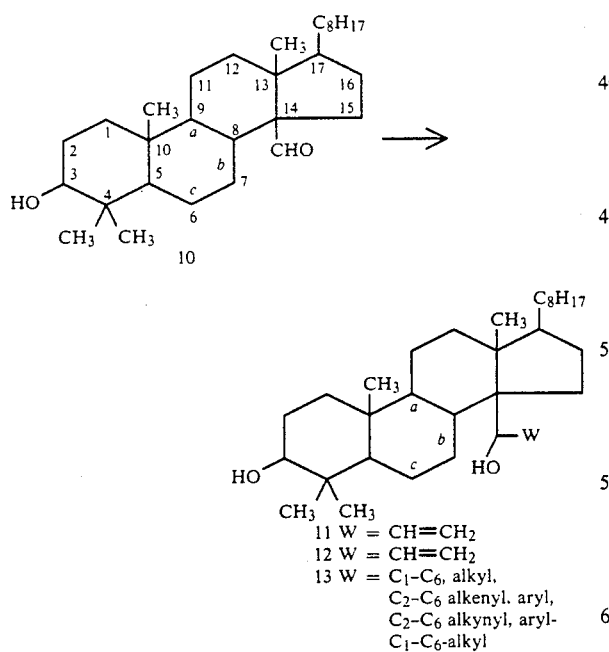

11 W = CH=CH₂
12 W = CH=CH₂
13 W = C₁-C₆ alkyl,
  C₂-C₆ alkenyl, aryl,
  C₂-C₆ alkynyl, aryl-
  C₁-C₆-alkyl Exposure of an anhydrous tetrahydrofuran solution of Compound 10a to an excess of a vinyl magnesium bromide tetrahydrofuran solution (Aldrich) at room temperature resulted in formation of the diastereomeric diols, Compound 11a and Compound 12a, in 87% combined yield. The diastereomers were separated by MPLC to provide Compound 11a in a 66% yield and Compound 12a in a 21% yield. Compounds 11a and 12a are two additional examples of 14α-substituted lanosterols of the present invention. In the same manner, Compounds 11b, 11c, 12b, and 12c may be prepared.

Compounds 13, compounds also within the scope of the invention, may be prepared in a similar fashion by adding CH₃ or any alkyl, alkenyl, aryl, arylalkyl, or alkynyl anion to compound 10.

Nitrogen was introduced into the steroid compound (SCHEME IV) by treating aldehyde Compound 7b with hydroxylamine hydrochloride (Aldrich) in pyridine for 16 hr.

SCHEME IV

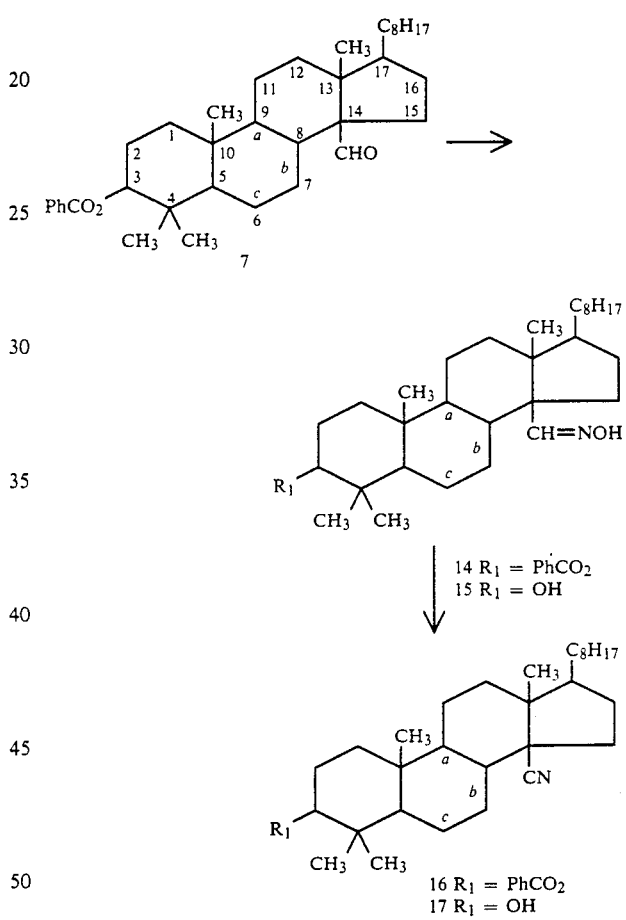

The resulting oxime, Compound 14b, was obtained in a yield of >95%. In a similar fashion, Compounds 14a (96% yield) and 14c (70% yield at 80° C.) were prepared from Compounds 7a and 7c, respectively.

Benzoate was removed from Compound 14b with ethanolic potassium hydroxide resulting in the hydroxy oxime 15b in a 94% yield. In the same manner oximes 15a and 15c were prepared from compounds 14a and 14c, respectively. Compounds 15a, 15b and 15c are all within the scope of the present invention. Preparation of the 14α-carbonitrile was achieved (SCHEME IV) by dehydrating the oxime Compound 14a directly with phenylisocyanate (Aldrich) and freshly distilled triethylamine to afford, after silica gel chromatography, the carbonitrile, Compound 16a, in 85% yield.

Similarly, Compounds 16b and 16c were prepared from Compounds 14b and 14c, respectively. Exposure of Compound 16a to ethanolic potassium hydroxide resulted in the removal of the benzoate and generated, after silica gel chromatography, the desired nitrile, Compound 17a (a compound of the present invention), in a 90% yield. In the same manner, nitrile compounds 17b and 17c, also within the scope of the present invention, may be prepared.

To prepare a variety of 14α-substituted lanosterols, the enones, Compounds 18 and 19 (SCHEME V), were prepared using the procedures previously reported in Woodward et al., J. Biol. Chem., 241:1502-1510 (1966).

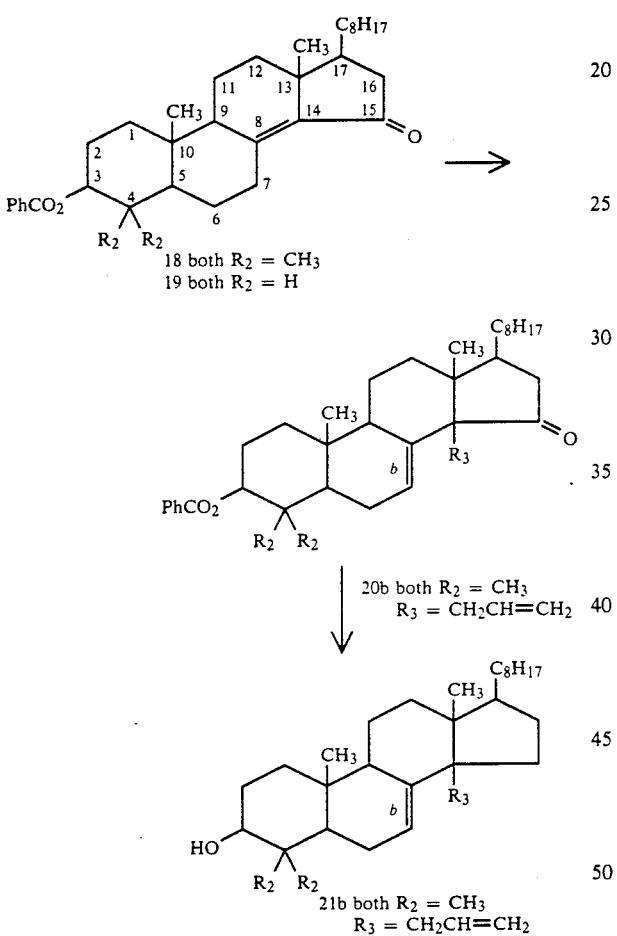

Compound 18 was alkylated with freshly distilled allyl bromide (Aldrich) in the presence of potassium tertiary butoxide in tertiary butanol to afford, after silica gel chromatography, the 14α-allyl-3β-benzoyloxy-4,4-dimethyl-5α-cholest-7-ene (Compound 20b), in a 20% yield (SCHEME V). The 15-ketone was reduced by treating Compound 20b with excess hydrazine in hot (180°-220° C.) diethylene glycol with excess sodium to generate the deprotected 14α-substituted dihydrolanosterol Compound 21b, a Formula I compound, as a mixture of 14α- and 7α-substituted lanosterols. The 14α and 7α compounds can then be separated by chemical chromatographic methods such as argenic chromatography readily known to those skilled in the art. In the same fashion, Compound 21a can also be prepared.

Using the above method, and modifications thereof which would be obvious to those skilled in the art, other examples of the lanosterols series within the scope of the present invention can be prepared.

15-Substitution (SCHEMES VI-VIIA)

Introduction of substituents at the 15-position required preparation of Compound 22b, 3β-bensoyloxy-15α-hydroxy-lanost-7-ene, and Compound 23b, 3β-benzoyloxy-15α-hydroxy-14α-methyl-5α-cholest-7-ene, using the methods reported in Woodward et al., J. chem. Soc., 1131-1143 (1957) and knight et al., J. Biol. Chem., 241:1502-1510 (12966)). Conversion (SCHEME VI) of the 15α-hydroxy substituent of Compound 22b to the 15α-fluoro steroid, Compound 24b, was achieved with the addition of DAST (diethylamino sulfur trifluoride, obtained from Aldrich) at −78° C. This retention of stereochemistry was confirmed by a series of NMR studies (Nuclear Overhauser Effect).

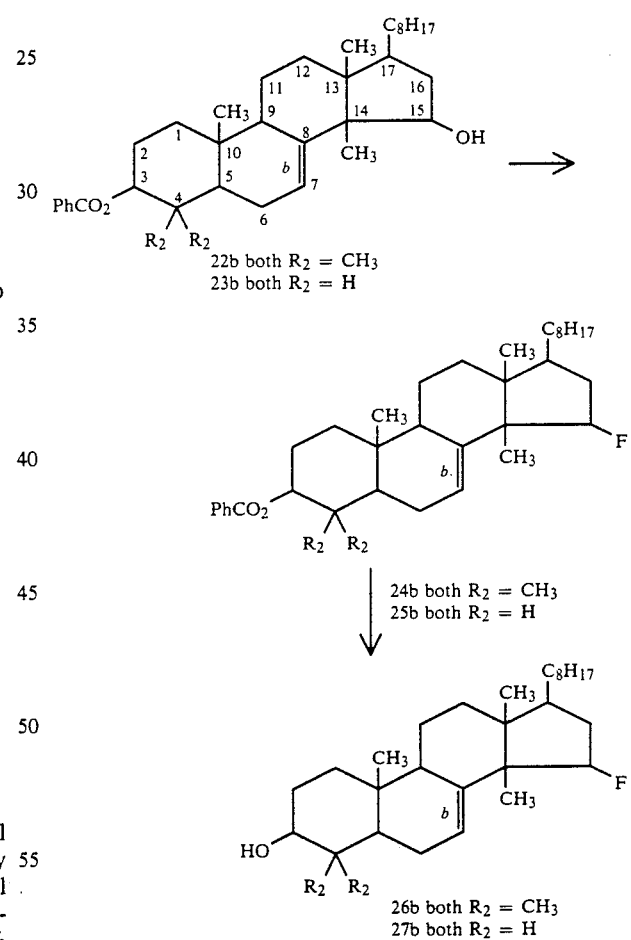

Reductive removal of the 15α-fluoro benzoate, Compound 24b, to the alcohol, Compound 26b, was performed by the addition of lithium aluminum hydride (Aldrich) to a cold (0° C.) ethereal solution (diethylether:tetrahydrofuran at a ratio of 4:1) of Compound 24b. Following the above procedure in the 4,4-desmethyl series, the fluoride, Compound 27b, was prepared from Compound 23b. both Compounds 26b and 27b are compounds of the present invention.

Starting from Compounds 22a and 23a, which were prepared in the same manner as Compounds 22b and 23b, respectively, the corresponding 15α fluorides, Compounds 26a and 27a, can be similarly prepared.

The ketones, Compounds 28b, 29b and 30b, previously reported by Woodward et al., J. Chem. Soc., 1131–1143, (1957); Knight et al., J. Biol. Chem., 241:1502–1510, (1966), can be elaborated to oximes and other heteroatom compounds substituted at the 15-position (Formula Ib) within the scope of the present invention (SCHEME VII).

SCHEME VII

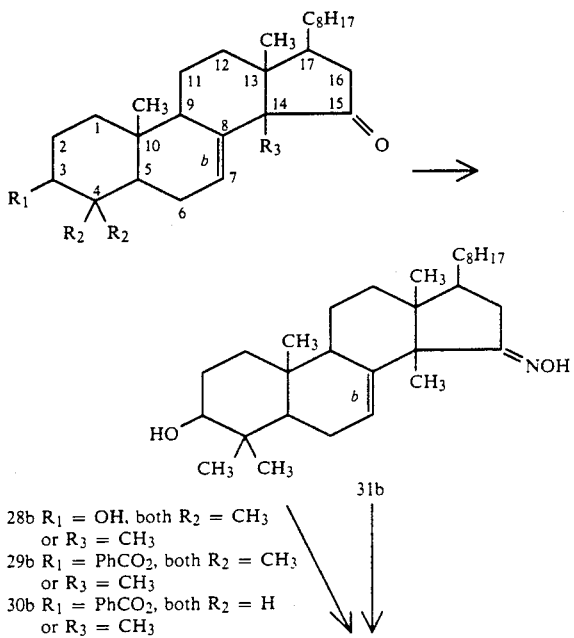

28b R$_1$ = OH, both R$_2$ = CH$_3$
  or R$_3$ = CH$_3$
29b R$_1$ = PhCO$_2$, both R$_2$ = CH$_3$
  or R$_3$ = CH$_3$
30b R$_1$ = PhCO$_2$, both R$_2$ = H
  or R$_3$ = CH$_3$ -continued
SCHEME VII

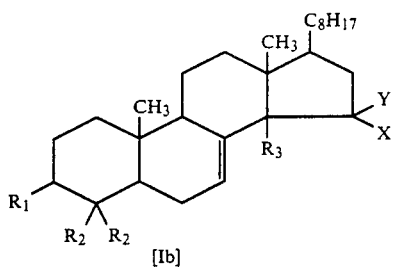

[Ib]

For example, exposure of 3β-hydroxy-lanost-7-en-15-one (Compound 28b) to hydroxylamine hydrochloride (Aldrich) in hot pyridine (80° C.) for 18 hr provided, after silica gel chromatography, the 15-oxime, Compound 31b in a yield of 85%. In the same manner, compound 31b was prepared in an 85% yield. Oxime Compound 31b provides another example of a compound of the present invention and in addition, along with Compounds 19b and 30b, provides a synthetic entry using conventional techniques to other compounds within the scope of the present claims.

The ketones (Scheme VIIA), compounds 19a, 30a and 42a, are prepared by the elaboration of Compounds 38a or 39a.

SCHEME VIIA

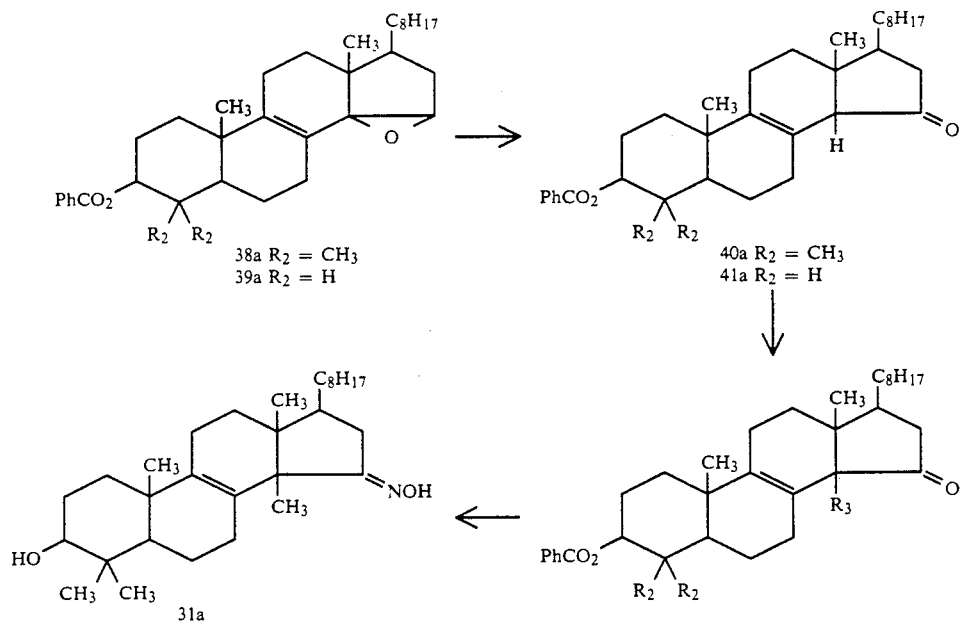

38a R$_2$ = CH$_3$
39a R$_2$ = H

40a R$_2$ = CH$_3$
41a R$_2$ = H

31a

SCHEME VIIA

-continued

29a $R_2 = CH_3$;
   $R_3 = CH_3$;
30a $R_2 = H$;
   $R_3 = CH_3$;
42a $R_2 = H$, or $CH_3$
   $R_3 = C_1-C_6$ alkyl, $C_2-C_6$
   alkenyl, $C_2-C_6$ alkynyl,
   $CH_2OCH_2Ph$, . . .
   (see legend I)

Preparation of epoxide 38a was performed using a process analogous to that described for the preparation of 39a in Anastasia et al., J. Org. Chem., 46:3265–3267 (1981). Exposure of the epoxide 38a to excess boron trifluoride etherate (Aldrich Chemical Co.) at 0° C. for 1 hour provided in 75% yield the new ketone 40a with the 14β hydrogen substitution. Alkylation of ketone 40a with methyl iodide in potassium tertiary butoxide in tertiary butanol supplied Compound 29a in 75% yield after recrystallization. Hydrolysis of the benzoate in Compound 29a using 5% potassium hydroxide in ethanol at 80° C. for 18 hours provided the hydroxy ketone, Compound 28a. Exposure of Compound 28 a to hydroxylamine hydrochloride (Aldrich) in hot pyridine (85° C.) for 18 hours afforded 15 oxime Compound 31a in 85% yield after recrystallization. In this manner Compounds 38a and 39a can be converted into Compounds 30a and 42a which are included in the scope of the invention. Elaboration of Compounds 29a, 30a and 42a in the similar fashion as Compounds 24b and 21 b provides entry into other compounds of the present invention. In addition, this process allows 14–15 difunctional modification of Compound 42a to generate additional compounds within the present scope.

14,15-Disubstitution (Schemes VIII and VIIB)

Introduction of 14,15-heteroatoms was achieved by exposing the diene, Compound 32a, prepared as reported in Woodward et al., J. Chem. Soc., 1131–1143 (1957) and Knight et al., J. Biol. Chem., 241:1502–1510 (1966), with osmium tetroxide in pyridine and benzene.

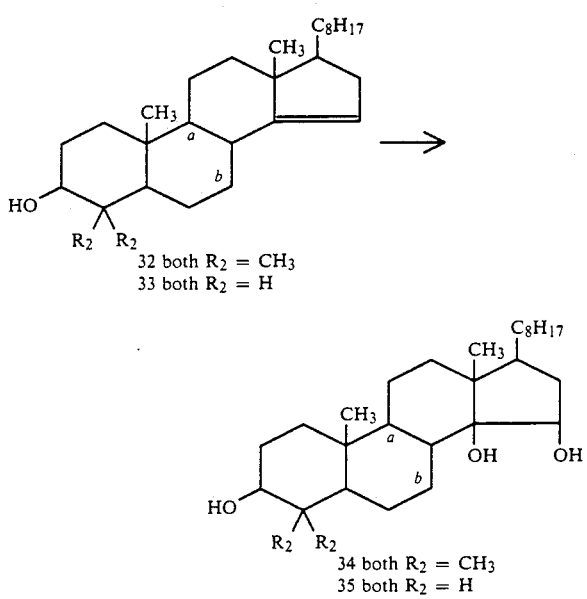

SCHEME VIII 32 both $R_2 = CH_3$
33 both $R_2 = H$ 34 both $R_2 = CH_3$
35 both $R_2 = H$ This reaction resulted, after silica gel chromatography, in the formation of the vicinal diol, Compound 34a, in an 81% yield. This 14,15-heteroatom substitution has been incorporated into the desmethyl series, Compound 33a, to make the triol, Compound 35a. Compounds 33a and 35a are two additional examples of compounds of the present invention. In this manner, starting with the 7,14-dienes (Compounds 32b and 33b), the corresponding compounds, Compounds 34b and 35b, may be prepared.

An example of 14,15-difunctional elaboration is illustrated in Scheme VIIB.

SCHEME VIIB

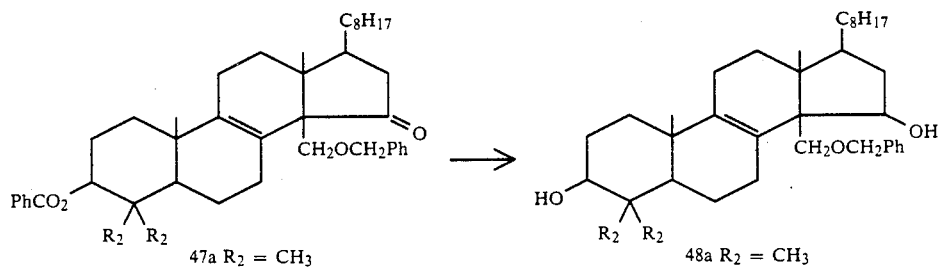

47a $R_2 = CH_3$

48a $R_2 = CH_3$

SCHEME VIIB
-continued

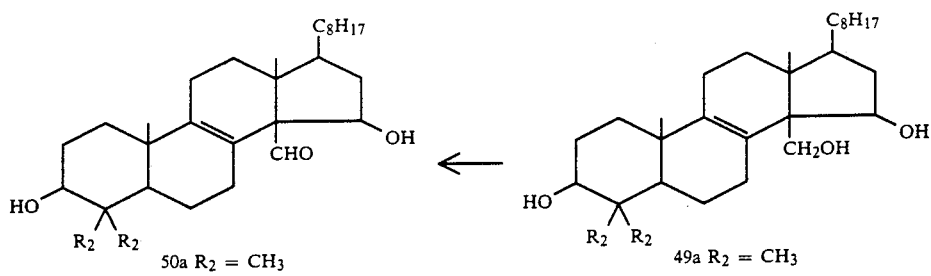

Compound 47a, prepared as described in SCHEME VIIA, was treated with lithium aluminum hydride (Aldrich) to generate the diol, Compound 48a in 64% yield. This diol was further treated with 10% palladium on activated carbon (Aldrich) in tetrahydrofuran, ethanol and acetic acid (25:25:1) to provide the triol Compound 49a in 61% yield. At this point, oxidizable functionality has been introduced at both the 15- and 32-position of lanostenol. Selective oxidation of the 32 alcohol was achieved by the treatment with pyridium dichromate (Aldrich) in dichloromethane to give after chromatography only Compound 50a in 63% yield. In this fashion this route offers a selective method for the preparations of oxidized funtionality at the 32-position of lanòstenol while keeping the 15-position in a functionalized form, thus affording a method for the preparation of a variety of 14,15-disubstituted lanosterols. Ketone removal in Compound 47a as indicated previously offers an alternative approach to prepare 14-substituted lanosterols.

General Procedure for the Preparation of Saturated 14,15-Substituted Lanosterols To prepare the saturated steroid ring system (SCHEME IX), the 3β-benzoyloxy-lanostan-7-one (compound 36) in Parish et al., J. Lipid Res., 22:859–868 (1981) was exposed to Wolf-Kishner conditions (see Knight et al., J. Am. Chem. Soc., 88(4):790–798).

SCHEME IX

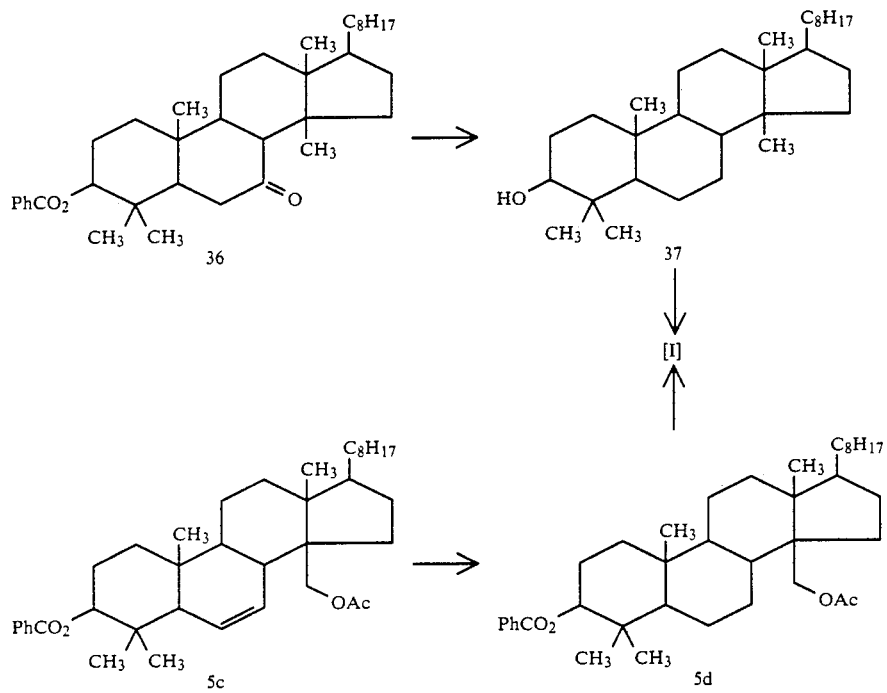

To a solution of sodium dissolved in diethylene glycol was added Compound 36 followed by excess anhydrous hydrazine. After heating (180° C.) for 48 hours, the excess hydrazine was distilled off over 48 hours at 220° C. resulting in lanostan-3β-ol (Compound 37) in approximately 50% yield.

Compound 5c is also a convenient starting material for the saturated lanostane ring system. Treatment of Compound 5c with 10% palladium on carbon in ethanol at 80° C. for 24 hours under 200 atmospheres of hydrogen afforded, after HPLC purification, 32-acetoxy-3β-benzoyloxy-lanostane (Compound 5d) in 76% yield. Compound 5d may be elaborated in the same fashion as Compound 5a–5c to generate the corresponding alcohol, Compound 6d. Compounds 6 and 37 afford synthetic entry to the saturated compounds of the present invention using the General Procedures described for the preparation of the corresponding unsaturated compounds.

Preparation of Salts

Physiologically acceptable salts of the compounds are also within the scope of the present invention and can be prepared in a number of ways apparent to those skilled in the art.

For example, metal salts can be made by contacting compounds of the invention with a solution of an alkali or alkaline earth metal salt having a sufficiently basic anion (e.g., hydroxide, alkoxide or carbonate). Quaternary amine salts can be made by similar techniques.

Salts can also be prepared by exchange of one cation for another. Cationic exchange can be effected by direct contact of an aqueous solution of a salt of a compound of the invention (e.g., alkali or quaternary amine salt) with a solution containing the cation to be exchanged. This method is most effective when the desired salt containing the exchange cation is unsoluble in water and can be separated by filtration.

Exchange may also be effected by passing an aqueous solution of a salt of a compound (e.g., an alkali metal or quaternary amine salt) through a column packed with a cation exchange resin containing the cation to be exchanged for that of the original salt and the desired product is eluted from the column. This method is particularly useful when the desired salt is water-soluble, e.g., a potassium, sodium or calcium salt.

Acid addition salts, useful in this invention, can be obtained by reacting a compound of the present invention with a suitable acid, e.g., p-toluene-sulfonic acid, acetic acid or the like.

The preparation of compounds within the scope of the invention is further illustrated by the following specific Examples.

Synthetic Examples

The following Examples describe synthetic procedures employed in production of specific compounds within the scope of the present invention. Unless otherwise indicated, all parts and percentages in the following Examples and in the General Procedures set forth above are by weight and all temperatures are reported in degrees Celsius (° C.). All chromatography solvent percentages were determined by volume. All proton NMR spectra are referenced to tetramethylsilane (TMS) at 0.00 ppm while all fluorine NMR spectra are referenced to freon-11 (F-11) at 0.00 ppm.

The following abbreviations are employed in the Examples:

NMR: nuclear magnetic resonance spectroscopy
IR: infrared spectroscopy
MS: mass spectrometry
HRMS: high resolution mass spectrometry
EI: electron impact
CI: chemical ionization
EA: elemental analysis
$[\alpha]^{25}$: optical rotation at 25° C. at the sodium D line
m.p.: melting point
MPLC: medium pressure liquid chromatography
HPLC: high pressure liquid chromatography
Rf: retention factor on silica gel thin layer chromatography
GC: gas chromatography Particular intermediates or products are identified by reference to the numbered compounds in the general synthetic procedures summarized above. Physical data for various compounds produced by procedures substantially corresponding to the description contained in each Example are provided following the individual Examples.

Example 1 (A-V)

Preparation of 14,15-Substituted Lanosterols

A. Preparation of 3$\beta$-benzoyloxy-lanost-7$\alpha$-ol (Compound 3)

Lanostane-3$\beta$-7$\alpha$-diol (compound 2) (4.6 g, 10.3 mmol) was dissolved in anhydrous pyridine (100 mL) at 40°. Benzoyl chloride (6.0 mL, 51.7 mmol) was added and the mixture was stirred at 40° for 25 min. The cooled reaction mixture (0°) was diluted with ice cold ether (200 mL) and acidified with 1N HCl to pH 6.5. The organic fraction was washed with 10% aqueous cupric sulfate (2×100 mL), water (1×50 mL), dried over anhydrous magnesium sulfate and evaporated under reduced pressure to afford the crude residue. The residue was subjected to medium pressure liquid chromatography (100 psi, 100 cm×2.7 cm) using 0.5% ethyl acetate in toluene (4L) and then 2% ethyl acetate in toluene (fractions: 27 mL). The contents of fractions 113 through 202 were pooled and evaporated under reduced pressure, providing 2.72 g (48%, corrected 64%) of pure Compound 3. Physical Data (Compound 3):

$[\alpha]^{25} = +25.8° +/-3.1°$ (C=0.64, CHCl$_3$);
m.p. = 190°–190.5° C. (white flakes, acetone);
RF = 0.55 (10% ethyl acetate in toluene);
NMR (300 MHz, CDCl$_3$): 8.06 (d, J=7.5 Hz, 2H, phenyl), 7.60–7.40 (m, 3H, phenyl), 4.79 (dd, J=11.4 Hz, 4.5 Hz, 1H, 3—CHOR), 4.11 (s, 1H, 7-CHOH), 2.0–0.85 (m, 27H), 1.11 (s, 3H, CH$_3$), 1.06 l(s, 3H, CH$_3$), 1.01 (s, 3H, CH$_3$), 0.93 (s, 3H, CH$_3$), 0.88 (d, J=6.6 Hz, 6H, 26-CH$_3$ and 27-CH$_3$), 0.88 (d, J=6.5 Hz, 3H, 21-CH$_3$), 0.76 (s, 3H, 18-CH$_3$);
IR (CHCl$_3$ solution, cm$^{-1}$): 3520 (bw, OH), 2950 (s, CH, sat), 2870 (s, CH sat), 1710 (s, C=O), 1600 (w), 1580 (w), 1465 (m), 1450 (m), 1275 (vs), 1115 (s);
MS (EI): 550 (3%, M+), 517 (21%, M —H$_2$O, —CVH$_3$), 395 (96%, M —H$_2$O, —CH$_3$, —C$_6$H$_5$COOH);
HRMS for C$_{37}$H$_{58}$O$_3$ (M+): calculated 550.4386, found 550.4354.

B. Preparation of 3$\beta$-benzoyloxy-7$\alpha$,32-epoxylanostane (Compound 4)

3$\beta$-benzoyloxy-lanost-7$\alpha$-ol (Compound 3) (2.72 g, 4.95 mmol) was dissolved in benzene (1.1L). About 150 mL of the solvent was distilled off to remove any traces of water. Lead tetraacetate (12.8 g, 28.9 mmol) (recrystallized from acetic acid) was added and the resulting mixture was refluxed under a nitrogen atmosphere for 17 hours. After cooling to room temperature, the reaction mixture was treated with a 20% aqueous potassium iodide solution (200 mL) then a saturated solution of sodium thiosulfate was added (until the yellow precipitate had dissolved), and the resultant mixture was extracted with diethyl ether (4×150 mL). The combined organic extracts were dried over anhydrous magnesium sulfate and evaporated under reduced pressure. The resulting residue was subjected to MPLC (35 psi; 50 cm×2.5 cm) using 5% diethyl ether in toluene as the eluting solvent (fraction size: 28 mL). The content of fractions 17 through 29 were pooled and the solvent was evaporated under reduced pressure, giving 1.90 g of Compound 4 (70% yield). Physical Data (Compound 4):

$[\alpha]^{25} = +41.0° +/- 0.8°$ (C=1.01, CHCl$_3$);
m.p.=225°-227° C. (fine needles, acetone);
Rf=0.60 (10% ethyl acetate in toluene);
NMR (300 MHz, CHCl$_3$): 8.05 (d, J=7.2 Hz, 2H, phenyl), 7.64-7.39 (m, 3H, phenyl), 4.75 (dd, J=11.5 Hz, 4.6 Hz, 1H, 3-CHOR), 4.22 (m, 1H, 7-CHOR), 4.02 (d, J=7.5 Hz, 1H, 32-CH$_2$OR), 3.38 (d, J=7.5 Hz, 1H, 32-CH$_2$OR), 2.1-0.8 (m, 26H), 1.03 (s, 3H, 31-CH$_3$), 0.92-0.87 (m, 18H, CH$_3$s);
IR (CHCl$_3$ solution, cm$^{-1}$): 295 (s, CH, sat), 2870 (s, CH sat), 1710 (s, C=O), 1278 (vs), 1116 (s), 1025 (m), 962 (m);
MS (EI): 517 (38%, M —CH$_2$OH), 403 (64%, M —CH$_2$OH—C$_8$H$_{18}$), 395 (10%, M CH$_2$OH—C$_6$H$_5$COOH);
HRMS for C$_{36}$H$_{53}$O$_2$ (M—CH$_2$OH): calculated 517.4045, found 517.3994.

C. Preparation of 32-acetoxy-3β-benzoyloxy-lanost-8-ene (Compound 5a), 32-acetoxy-3/b-benzoyloxy-lanost-7ene (Compound 5b) and 32-acetoxy-3β-benzoyloxy-lanost-6ene (Compound 5c)

3β-benzoyloxy-7α-32-epoxy-lanostane (Compound 4) (1.90 g, 3.47 mmol) was refluxed for 18 hr in acetic anhydride (380 mL) with pyridine hydrochloride (3.8 g, 32.9 mmol) under nitrogen. After cooling (25°), the mixture was poured into ice-water (400 mL) and stirred for 2 hr. This aqueous mixture was then extracted with diethyl ether (4×150 mL) and the combined ether extracts were washed successively with cold (0°) aqueous 5% hydrochloric acid (300 mL), saturated aqueous sodium bicarbonate (8×200 mL), water (2×100 mL) and brine (100 mL). the extract was dried over anhydrous magnesium sulfate and evaporation was carried out under reduced pressure. The crude product was subjected to MPLC (100 psi, 100 cm×2.5 cm) using toluene (4L) and then 0.5% ethyl acetate in toluene as the eluting solvent (fraction size: 27 mL). The contents of the following fractions were pooled and evaporated to dryness: (1) fractions 274-311 (Compound 5c), 329 mg (16%); (2) fractions 312-327 (compound 5a), 249 mg; (3) fractions 366-402 (Compound 5b), 245 mg and (4) fractions 328-365 (Compounds 5a and 5b in a 32:68 mixture, 461 mg. The mixture of Compounds 5a and 5b was resolved by repeating HPLC (400 psi, 50 cm×2.5 cm) using 0.25% ethyl acetate in toluene as the eluting solvent. Total yields for Compound 5a=19%, Compound 5b=27% and Compound 5c=16%.

Physical Data (Compound 5a):
$[\alpha]^{25} = +61° +/-2°$ (c=1.00, CHCl$_3$);
m.p.=109.5°-110° C. (ethanol - 5% water, needles);
Rf=0.64 (10% ethyl acetate in toluene);
NMR (300 NHz, CDCl$_3$): 8.06 (d, J=7.2 Hz, 2H, phenyl), 7.60-7.40 (m, 3H, phenyl), 4.75 (dd, J=11.4 Hz, 4.2 Hz, 1H, 3-CHOR), 4.08 (d, J=10.5 Hz, 1H, 32-CH$_2$OH), 3.97 (d, J=10.5 Hz, 1H, 32-CH$_2$OR), 2.2-0.85 (m, 26H), 2.06 (s, 3H, acetate), 1.08 (s, 3H, CH$_3$), 1.06 (s, 3H, CH$_3$), 0.97 (s, 3H, 30-CH$_3$), 0.90 (d, J=6.3 Hz, 3H, 21-CH$_3$), 0.88 (d, J=6.6 Hz, 6H, 26-CH$_3$ and 27-CH$_3$), 0.73 (s, 3H, 18-CH$_3$);
IR (CHCl$_3$ solution, cm$^{-1}$): 2950 (s, CH, sat), 2860 (s, CH sat), 1710 (s, C=O), 1600 (m), 1465 (s), 1450 (s), 1275 (vs), 1115 (s), 1025 (s), 980 (s), 970 (s); MS (EI): 530 (2% M —CH$_3$CO$_2$H), 517 (22%, M —CH$_2$OC$OCH_3$), 395 (100%, M —CH$_2$OCOCH$_3$, —C$_6$H$_5$CO$_2$H);
HRMS for C$_{37}$H$_{54}$O$_2$ (M —CH$_3$CO$_2$H): calculated 530.4142, found 530.4116.

Physical Data (Compound 5b):
$[\alpha]^{25} = +50° +/-2°$ (c=1.03, CHCl$_3$);
m.p.=154°-155° C. (ethanol - 5% water, needles);
Rf=0.63 (10% ethyl acetate in toluene);
NMR (300 MHz, CDCl$_3$): 8.06 (d, J=7.2 Hz, 2H, phenyl), 7.60-7.40 (m, 3H, phenyl), 5.25 (d, J=4.8 Hz, 1H, 7-CH), 4.79 (dd, J=10.8 Hz, 4.2 Hz, 1H, 3-CHOR), 4.59 (d, J=10.8 Hz, 1H, 32-CH$_2$OR), 3.73 (d, J=10.8 Hz, 1H, 32-CH$_2$OR), 2.15-0.85 (m, 25H), 1.99 (s, 3H, acetate), 1.13 (s, 3H, 31-CH$_3$), 0.95 (s, 3H, CH$_3$), 0.94 (s, 3H, CH$_3$), 0.90 (d, J=6.0 Hz, 3H, 21-CH$_3$), 0.88 (d, J=7.2 Hz, 6H, 26-CH$_3$ and 27-CH$_3$), 0.73 (s, 3H, 18-CH$_3$);
IR (CHCl$_3$ solution, cm$^{-1}$): 2950 (s, CH, sat), 2860 (s, CH sat), 1710 (s, C=O), 1600 (m), 1465 (s), 1450 (s), 1380 (s), 1365 (s), 1275 (vs), 1115 (s), 1025 (s), 965 (s);
MS (EI): 517 (25%, M —CH$_2$CO$_2$CH$_3$), 395 (100%, M —CH$_2$CO$_2$CH$_3$);
HRMS for C$_{36}$H$_{50}$O$_2$ (M —CH$_3$CO$_2$CH$_3$): calculated 517.4045, found 517.3999.

Physical Data (compound 5c):
$[\alpha]^{25} = -36.6° +/-2°$ (c=1.01, CHCl$_3$);
m.p.=141°-141.5° C. (ethanol - 5% water, very fine needles);
Rf=0.66 (10% ethyl acetate in toluene);
NMR (300 MHz, CDCl$_3$): 8.06 (d, J=7.2 Hz, 2H, phenyl), 7.60-7.40 (m, 3H, phenyl), 5.61 (d, J=10.2 Hz, 1H, olefinic H), 5.52 (d, J=10.2 Hz, 1H, olefinic H), 4.77 (dd, J=11.4 Hz, 4.8 Hz, 1H, 3-CHOR), 4.56 (d, J=11.5 Hz, 1H, 32-CH$_2$OR), 3.96 (d, J=11.5 Hz, 1H, 32-CH$_2$OR), 2.42-0.85 (m, 24H), 1.99 (s, 3H, acetate), 1.03 (s, 3H, 31-CH$_3$), 0.97 (s, 3H, CH$_3$), 0.91-0.87 (m, 15H, CH$_3$s);
IR (CHCl$_3$ solution, cm$^{-1}$): 2950 (s, CH, sat), 2860 (s, CH sat), 1720 (s, C=O), 1600 (m), 1470 (s), 1450 (s), 1385 (s), 1370 (s), 1315 (s), 1275 (vs), 1115 (s), 1025 (s), 970 (s);
MS (EI): 517 (9%, M —CH$_2$OCOCH$_3$), 453 (32% M —CH$_3$CO$_2$H, —C$_6$H$_5$), 408 (30%, M —CH$_3$CO$_2$H, —C$_6$H$_5$CO$_2$H), 395 (100%, M —CH$_2$OCOCH$_3$, —C$_6$H$_5$CO$_2$H);
HRMS for C$_{36}$H$_{53}$O$_2$ (M —CH$_2$OCOCH$_3$): calculated 517.4045, found 517.4042.

D. Preparation of 3β-benzoyloxy-lanost-8en-32-ol (Compound 6a)

32-acetoxy-3β-benzoyloxy-lanost-8ene (Compound 5a) (330 mg, 559 μmol) was dissolved in ethanol (100 mL) and treated with potassium hydroxide (87%, 8.3 g) in ethanol (23 mL) and water (7 mL) at 5°. The mixture was stirred at 10° for 2 hr and quenched with ice water (40 mL). The mixture was then extracted with dichloromethane (3×100 mL) with the combined organic fractions dried over anhydrous magnesium sulfate and evaporated under reduced pressure. The residue was subjected to MPLC (55 psi, 50 cm×1.8 cm) using 2% ethyl acetate in toluene as the eluting solvent (fractions 18 mL). The contents of fractions 13 through 35 were pooled, and after evaporation under reduced pressure provided 209 mg (68%) of (Compound 6a).

Physical Data (Compound 6a):
$[\alpha]^{25} = +79° +/-2°$ (c=1.02, CHCl$_3$);
m.p.=167°-168.5° C. (ethanol - 5% water);
Rf=0.50 (10% ethyl acetate in toluene);
NMR (300 MHz, CDCl$_3$): 8.06 (d, J=7.2 Hz, 2H, phenyl), 7.60-7.40 (m, 3H, phenyl), 4.75 (dd, J=11.7 Hz, 4.2 Hz, 1H, 3-CHOR), 3.66 (dd, J=10.8 Hz, 9.3 Hz, 1H, 32-CH$_2$OR), 3.25 (dd, J=10.8 Hz, 3.8 Hz, 1H, C-32-

H), 2.15–0.85 (m, 26H), 1.13 (s, 3H, CH$_3$), 1.08 (s, 3H, CH$_3$), 0.88 (d, J=6.6 Hz, 6H, 26-CH$_3$ and 27-CH$_3$), 0.72 (s, 3H, 18-CH$_3$);

IR (CHCl$_3$ solution, cm$^{-1}$): 3480 (bw, OH), 2950 (s, CH, sat), 2860 (s, CH sat), 1710 (s, C=O), 1460 (s), 1445 (s), 1305 (s), 1275 (vs), 1115 (s);

MS (EI): 530 (8%, M —H$_2$O), 518 (42% M —CH$_2$O), 395 (68%, M —CH$_2$OH, —C$_6$H$_5$CO$_2$H), 105 (100%, C$_6$H$_5$CO+);

HRMS for C$_{37}$H$_{54}$O$_2$ (M —H$_2$O): calculated 530.4124, found 530.4162.

Physical Data (Compound 6b; 73% yield from Compound 5b):
[α]$^{25}$ = +51.5° +/−2° (c=1.01, CHCl$_3$);
m.p.=209.5°-211° (acetone, needles);
Rf=0.50 (10% ethyl acetate in toluene);
NMR (300 MHz, CDCl$_3$): 8.06 (d, J=7.5 Hz, 2H, phenyl), 7.60-7.40 (m, 3H, phenyl), 5.39 (m, 1H, 7-CH), 4.75 (dd, J=4.7 Hz, 11.3 Hz, 1H, 3-CHOR), 3.66 (d, J=10.2 Hz, 1H, 32-CH$_2$OR), 3.26 (t, J=10.2 Hz, 1H, 32-CH$_2$OH), 2.15-0.85 (m, 26H), 0.96 (s, 3H, CH$_3$), 0.89 (d, J=6.5 Hz, 3H, 21-CH$_3$), 0.87 (d, J=6.8 Hz, 6H, 26-CH$_3$ pl and 27-CH$_3$), 0.74 (s, 3H, 18-CH$_3$);

IR (CHCl$_3$ solution, cm$^{-1}$): 3500 (bw, OH), 2940 (s, CH, sat), 2860 (s, CH sat), 1705 (s, C=O), 1600 (m), 1465 (s), 1315 (s), 1275 (vs), 1115 (s), 1020 (s), 970 (s);

MS (EI): 518 (22%, M —CH$_2$OL), 395 (37%, M —CH$_2$OH, —C$_6$H$_5$CO$_2$H), 381 (19%, M—CH$_2$O, —C$_6$H$_5$CO$_2$H, —CH$_3$), 105 (100%, C$_6$H$_5$CO+);

HRMS for C$_{36}$H$_{54}$O$_2$ (M —CH$_2$O): calculated 518.4124, found 518.4161.

Physical Data (Compound 6c; 62% yield from Compound 5c):
[α]$^{25}$ = +−0.9° +/−2.0° (c=1.02, CHCl$_3$);
m.p.=222°-223° (ethanol, needles);
Rf=0.55 (10% ethyl acetate in toluene);
NMR (300 MHz, CDCl$_3$): 8.05 (d, J=7.5 Hz 2H phenyl), 7.60-7.40 (m, 3H, phenyl), 5.85 (d, J=10.2 Hz, 1H, olefinic H), 5.69 (d, J=10.2 Hz, 1H, olefinic H), 4.78 (dd, J=11.6 Hz, 4.7 Hz, 1H, 3-CHOR), 4.20 (d, J=11.5 Hz, 1H, 32-CH$_2$OH), 3.46 (t, J=11.5 Hz, 1H, 32-CH$_2$OH), 2.40 (m, 1H), 2.12-0.85 (m, 24H), 1.04 (s, 3H, CH$_3$), 0.98 (s, 3H, CH$_3$), 0.93 (s, 3H, CH$_3$), 0.90-0.84 (m, 12H, CH$_3$s); IR (CHCl$_3$ solution, cm$^{-1}$): 3690 (w, OH), 3540 (bw, OH), 2960 (s, CH, sat), 2870 (s, CH sat), 1710 (s, C=O), 1600 (w), 1580 (w), 1470 (m), 1450 (m), 1315 (m), 1280 (vs), 1120 (s);

MS (EI): 530 (5%, M —H$_2$OL), 517 (17%, M —CH$_2$OH), 408 (15%, M —H$_2$O, —C$_6$H$_5$COOH), 403 (8%, M —CH$_2$OH, —C$_8$H$_{18}$), 395 (100%, M —CH$_2$OH, —C$_6$H$_5$COOH);

HRMS for C$_{37}$H$_{54}$O$_2$ (M —H$_2$O): calculated 530.4124, found 530.4093.

E1. Preparation of 3β-benzoyloxy-lanost-8-en-32-al (Compound 7a)

3β-benzoyloxy-lanost-8-en-32-ol (Compound 6a) (200 mg, 365 μmol) was dissolved in acetone (100 mL) and treated with Jones reagent (2.3 mL) at −10°. The mixture was stirred for 15 min at −10°. The reaction mixture was diluted with water (100 mL) and quickly extracted with toluene (3×50 mL). The combined toluene fractions were washed with water (2×50 mL), dried over anhydrous magnesium sulfate, and removed by evaporation under reduced pressure. The resulting residue was subjected to MPLC (50 psi, 50 cm×1.8 cm) being eluted with toluene. The procedure resulted in 185 mg (93%) of Compound 7a.

Physical Data (Compound 7a):
[α]$^{25}$ = −243° +/−4° (c=1.00, CHCl$_3$);
m.p.=206°-207° (acetone, fine needles);
Rf=0.60 (toluene);
NMR (300 MHz, CDCl$_3$): 9.47 (s, 1H, 32-CHO), 8.05 (d, J=7.5 Hz, 2H, phenyl), 7.60-7.40 (m, 3H, phenyl), 4.73 (dd, J=11.6 Hz, 5.1 Hz, 1H, 3-CHOR), 2.4-0.85 (m, 26H), 1.14 (s, 3H, CH$_3$), 1.07 (s, 3H, CH$_3$), 0.94 (s, 3H, CH$_3$), 0.90 (d, J=6.3 Hz, 3H, 21-CH$_3$), 0.87 (d, J=6.6 Hz, 6H, 26-CH$_3$ and 27-CH$_3$), 0.77 (s, 3H, 18-CH$_3$);

IR (CHCl$_3$ solution, cm$^{-1}$): 2940 (s, CH, sat), 2860 (s, CH sat), 1710 (s, C=O), 1690 (s, C=O), 1465 (s), 1450 (s), 1275 (vs), 1115 (s);

MS (EI): 517 (37%, M —CHO), 395 (100%, M —CHO, —C$_6$H$_5$CO$_2$H);

HRMS for C$_{36}$H$_{53}$O$_2$ (M —CHO): calculated 517.4046, found 517.4076.

Physical Data (Compound 7b, 85% yield from Compound 6b; reaction time=1.5 hours at 0°):
[α]$^{25}$ = +46.5° +/−2° (c=0.99, CHCl$_3$);
m.p.=193.5°-195.5° (acetone, fine needles);
Rf=0.6 (toluene);
NMR (300 MHz, CDCl$_3$): 9.66 (s, 1H, 32-CHO), 8.05 (d, J=7.5 Hz, 2H, phenyl), 7.60-7.40 (m, 3H, phenyl), 5.45 (m, 1H, 7-CH), 4.76 (dd, J=11.1 Hz, 4.2 Hz, 1H, 3-CHOR), 2.2-9.85 (m, 25H), 1.14 (s, 3H, CH$_3$), 0.98 (s, 3H, CH$_3$), 0.95 (s, 3H, CH$_3$), 0.93 (d, J=6.5 Hz, 3H, 21-CH$_3$), 0.87 (d, J=6.6 Hz, 6H, 26-CH$_3$ and 27-CH$_3$), 0.75 (s, 3H, 18-CH$_3$);

IR (CHCl$_3$ solution, cm$^{-1}$): 2950 (s, CH, sat), 2860 (s, CH sat), 1705 (s, C=O), 1600 (m), 1275 (vs), 1115 (s), 970 (s);

MS (EI): 518 (5%, M —CO), 517 (13%, M —CHO), 395 (68%, M —CHO, —C$_6$H$_5$CO$_2$H), 105 (100%, C$_6$H$_5$CO+);

HRMS for C$_{36}$H$_{54}$O$_2$ (M —CO)P calculated 518.4124, found 518.4115.

E2. Preparation of 3β-benzoyloxy-lanost-6-en-32-al (Compound 7c)

3β-benzoyloxy-lanost-6-en-32-ol (compound 6c) (73 mg, 133 μmole) was dissolved in dichloromethane (distilled from phosphorus pentoxide) (5 mL) and treated with pyridinium dichromate (98%, Aldrich) (74 mg, 193 μmole) and 4 powdered molecular sieves (aldrich) (72 mg) at room temperature under dry nitrogen atmosphere. After stirring 2 hr, diethyl ether was added (40 mL) and the mixture was filtered through florisil and Celite (obtained from Manville Products Corp., Denver, Colo.). Evaporation of solvents under reduced pressure gave a residue that was subjected to MPLC (70 psi, 50 cm×1.2 cm) using toluene as the elutant, to afford 42.9 mg (60%) of Compound 7c.

Physical Data (Compound 7c:
[α]$^{25}$ = −26.8° +/−2.0° (c=1.01, CHCl$_3$);
m.p.=175°-177° (acetone, very fine needles);
Rf=0.8 (5% ethyl acetate in toluene);
NMR (300 MHz, CDCl$_3$): 9.97 (s, 1H, 32-CHO), 8.05 (d, J=7.5 Hz, 2H, phenyl), 7.60-7.40 (m, 3H, phenyl), 5.69 (d, J=10.7 Hz, 1H, olefinic H), 5.64 (d, J=10.7 Hz, 1H, olefinic H), 4.74 (dd, J=11.7 Hz, 4.8 Hz, 1H, 3-CHOR), 2.46 (m, 1H), 2.23-0.85 (m, 23H), 1.03 (s, 3H, CH$_3$), 0.97 (s, 3H, CH$_3$), 0.95-0.90 (m, 12H, CH$_3$s), 0.87 (d, J=6.6 Hz, 6H, 26-CH$_3$ and 27-CH$_3$);

IR (KBr wafer, cm$^{-1}$): 2950 (s, CH, sat), 2870 (s, CH sat), 1718 (s, C=O), 1710 (s, C=O), 1600 (w), 1580 (w), 1465 (m), 1450 (m), 1275 (vs), 1115 (s);

Ms (EI): 546 (1%, M+), 518 (29%, M —CO), 396 (44%, M —CO, —C$_6$H$_5$COOH), 381 (100%, M —CO, —C$_6$H$_5$COOH, CH$_3$);

HRMS for C$_{37}$H$_{54}$O$_3$ (M+): calculated 546.4073, found 546.4099.

F. Preparation of 3β-benzoyloxy-32,32-difluorolanost-8ene (Compound 8a)

Azeotropically (benzene) dried 3β-benzoyloxy-lanost-8en-32al (180 mg, 330 μmol) (Compound 7a) was stirred at 80° in neat DAST (diethylamino sulfur trifluoride) (5 mL) under an argon atmosphere for 4.5 hr. After cooling (0°), the reaction mixture was cautiously added, dropwise, to cold (0°) saturated aqueous sodium bicarbonate (100 mL) and dichloromethane (100 mL). After separation, the aqueous phase was reextracted with dichloromethane (2×100 mL) and the combined dichloromethane layers were washed with water (1×100 mL), dried over anhydrous magnesium sulfate, and filtered. Then the dichloromethane was removed by evaporation under reduced pressure. The residue was dissolved in dichloromethane, filtered through silica gel and the solvent once again removed by evaporation, this time in vacuum. This residue was subjected to MPLC (35 psi, 50 cm×1.8 cm) using 25% toluene in hexane as the eluting solvent (fractions: 9 mL) giving 141 mg (75%) of Compound 8a of 911% purity determined by capillary GC (DB-1, 320°, H$_2$).

Physical Data (Compound 8a; repurified by HPLC to 98.8% purity):

$[α]^{25} = +74.3° +/- 2.0°$ (c=0.99, CHCl$_3$);

m.p.=188°–190° (needles, acetone);

Rf=0.80 (toluene);

NMR (300 MHz, CDCl$_3$): 8.05 (D, J=7.2 Hz, 2H, phenyl), 7.60–7.40 (m, 3H, phenyl), 5.72 (d, J=57.5 Hz, 56.0 Hz, 1H, 32-CHF$_2$), 4.76 (dd, J=11.1 Hz, 7.5 Hz, 1H, 3-CHOR), 2.2–0.85 (m, 26H), 1.09 (s, 3H, CH$_3$), 1.06 (s, 3H, CH$_3$), 0.97 (s, 3H, 30-CH$_3$), 0.90 (d, J=6.3 Hz, 3H, 21-CH$_3$), 0.87 (d, J=6.8 Hz, 6H, 26-CH$_3$ and 27-CH$_3$), 0.74 (s, 3H, 18-CH$_3$);

19F-NMR (188.2 MHz, CDCl$_3$): −115.97 (dd, J=277.1 Hz, 57.5 Hz, 1 F, 32-CHF$_2$), −122.35 (dd, J=277.1 Hz, 55.0 Hz, 1 F, 32-CHF$_2$);

IR (KBr wafer, cm$^{-1}$): 2950 (s, CH, sat), 2860 (s, CH sat), 1710 (s, C=O), 1600 (w), 1280 (vs), 1125 (s), 1020 (s);

MS (EI):568 (1%, M+), 528 (4%, M −2HF), 517 (20%, M —CHF$_2$), 395 (47%, M —CHF$_2$, —C$_6$H$_5$CO$_2$H), 105 (100%, —C$_6$H$_5$CO+);

HRMS for C$_{37}$H$_{54}$O$_2$F$_2$ (M+): calculated 568.4092, found 568.4079.

Physical Data (Compound 8b; 48% yield from Compound 7b; repurified by HPLC to 97 pure):

$[α]^{25} = +47.5° +/- 2.0°$ (c=1.02, CHCl$_3$);

m.p.=207.5°–208.5° (acetone);

Rf=0.80 (toluene);

NMR (300 MHz, CDCl$_3$):8.05 (d, J=7.8 Hz,2H, phenyl), 7.60–7.40 (m, 3H, phenyl), 5.98 (t, J=56.3 Hz, 1H, 32-CHF$_2$), 5.39 (m 1H, 7-CH), 4.77 (dd, J=11.0 Hz, 3.8 Hz, 1H, 3-CHOR), 2.15–0.85 (m, 25H), 1.14 (s, 3H, 31-CH$_3$), 0.97 (s, 3H, CH$_3$), 0.96 (s, 3H, CH$_3$), 0.93 (d, J=6.3 Hz, 3H, 21-CH$_3$), 0.88 (d, J=6.6 Hz, 6H, 26-CH$_3$ and 27-CH$_3$), 0.75 (s, 3H, 18-CH$_3$);

19 F-NMR (188.2 MHz, CDCl$_3$): −118.15 (dd, J=277 Hz, 56 Hz, 1 F, 32-CHF$_2$), −123.26 (dd, J=277 Hz, 56 Hz, 1 F, 32-CHF$_2$);

IR (KBr wafer, cm$^{-1}$): 2940 (s, CH, sat), 2880 (s), 2860 (s, CH sat), 1708 (vs, C=O), 1600 (w), 1280 (vs), 1115 (s), 1045 (s);

MS (EI):517 (5%, M —CHF$_2$), 395 (20%, M —CHF$_2$, —C$_6$H$_5$CO$_2$H);

HRMS for C$_{36}$H$_{53}$O$_2$ (M —CHF$_2$): calculated 517.4045, found 517.4024.

G. Preparation of 32,32-difluoro-lanost-8-en-3β-ol (Compound 9a)

Lithium aluminum hydride (28 mg, 738 μmol), obtained from Alfa Products) was added, at room temperature, to 3β-benzoyloxy-32,32-difluorolanost-8-ene (Compound 8a) (141 mg, 248 μmol) which had been dissolved in anhydrous (distilled from sodium and benzophenone) diethyl ether (20 mL). The resulting mixture was stirred for 20 min. The cooled (0°) reaction was quenched with the careful addition of ice water then a saturated solution of ammonium chloride. After separation, the aqueous layer was extracted with dichloromethane (2×100 mL) and the combined organic extracts were pooled, dried over anhydrous magnesium sulfate and the solvent removed by evaporation under reduced pressure. The resulting mixture of residues was subjected to MPLC (45 psi, 50 cm×1.8 cm), being eluted with 4 % ethyl acetate in toluene, and collected to provide a sample for final purification by HPLC (60 psi, 60 cm×2.5 cm). For HPLC, the eluting solvent was hexane:toluene:ethyl acetate (74:21:5). HPLC afforded 99 mg of Compound 9a in 86% yield.

Physical Data (Compound 9a):

$[α]^{25} = +68° +/- 2.0°$ (c=1.00, CHCl$_3$);

m.p.=119.5°–120.5° (powder);

Rf=0.3 (10% ethyl acetate in toluene);

NMR (300 MHz, CDCl$_3$): 5.70 (dd, J=55.8 Hz, 57.5 Hz, 1H, 32-CHF$_2$), 3.26 (m, 1H, 3-CHOH), 2.15–0.85 (m, 26H), 1.02 (s, 3H, CH$_3$), 1.01 (s, 3H, CH$_3$), 0.90 (d, J=6.6 Hz, 3H, 21-CH$_3$), 0.87 (d, J=7.2 Hz, 6H, 26-CH$_3$ and 27-CH$_3$), 0.83 (s, 3H, 30-CH$_3$), 0.73 (s, 3H, 18-CH$_3$);

19F-NMR (188.2 MHz, CDCl$_3$): −116.06 (dd, J=276.7 Hz, 57.5 Hz, 1 F, 32-CHF$_2$), −122.25 (dd, J=276.7 Hz, 55.8 Hz, 1 F, 32-CHF$_2$);

IR (CHCl$_3$ solution, cm$^{-1}$):3600 (m, OH), 3460 (wb, OH), 2950 (s, CH sat), 2860 (s CH sat), 1470 (s), 1375 (s), 1105 (s), 1090 (s), 1015 (s), 910 (s);

MS (EI): 464 (10%, M+), 447 (4%, M —OH), 431 (12%, M —CH$_3$, —H$_2$O), 413 (100%, M —CHF$_2$), 395 (46%, M —H$_2$O, —CHF$_2$);

HRMS for C$_{30}$H$_{50}$OF$_2$ (M+): calculated 464.3830, found 464.3794;

EA for C$_{30}$H$_{50}$OF$_2$: calculated, C 77.54%, H 10.85%, F 8.18%,; found, C 77.38%, H 10.86%, F 7.87%.

Physical Data (Compound 9b; 86% yield from Compound 8b):

$[α]^{25} = +17.7° +/- 3.2°$ (c=0.62, (CHCl$_3$);

m.p.=138°–139° (powder);

Rf=0.30 (10% ethyl acetate in toluene);

NMR (300 MHz, CDCl$_3$):5.96 (t, J=56.4 Hz, 1H, 32-CHF$_2$), 5.38 (m, 1H, 7-CH), 3.26 (dd, J=10.2 Hz, 5.1 Hz, 1H, 3-CHOH), 2.2–0.85 (m, 26H), 1.00 (s, 3H, 31-CH$_3$), 0.92 (d, J=6.5 Hz, 3H, 21-CH$_3$), 0.90 (s, 3H, CH$_3$), 0.89 (d, J=6.5 Hz, 6H, 26-CH$_3$ and 27-CH$_3$), 0.86 (s, 3H, CH$_3$), 0.73 (s, 3H, 18-CH$_3$);

19F-NMR (188.2 MHz, CDCL$_3$): −118.02 (dd, J=277 Hz, 56 Hz, 1 F, 32-CHF$_2$), −123.23 (dd, J=277 Hz, 56 Hz, 1 F, 32-CHF$_2$);

IR (CHCl$_3$ solution, cm$^{-1}$):3620 (m, OH), 3450 (bw, OH), 2960 (s, CH sat), 2940 (s CH sat), 2870 (s CH sat), 1470 (m), 1380 (m), 1365 (m), 1095 (m), 1050 (s), 655 (m);

MS (EI):464 (5%, M+), 431 (10%, M, —H$_2$O, —CH$_3$), 413 (100%, M —CHF$_2$), 395 (60%, M —H$_2$O, —CHF$_2$);

HRMS for C$_{30}$H$_{50}$OF$_2$ (M+): calculated 464.4830, found 464.3792;

EA for C$_{30}$H$_{50}$OF$_2$: calculated, C 77.54%, H 10.85%, F 8.18%; found, C 77.19%, H 10.70%, F 8.13%.

H. Preparation of both diastereomers of 4,4-dimethyl14α-(1'-hydroxy-2'-phenyl)-5α-cholest-8-en-3β-ol (Compounds 11a and 12a)

A 1.6M solution of vinyl magnesium bromide in tetrahydrofuran (1.0 mL, 1.60 mmol) as added to a solution of lanost-8-en-32-al-3β-ol (prepared as described by Shafiee et al., *J. Lipid Res.*, 17:1–10 (1986)) (Compound 10a) (74.5 mg, 168 µmol) in dry (distilled from sodium and benzophenone) tetrahydrofuran (5 mL) at room temperature. After stirring for 120 min at room temperature, saturated ammonium chloride solution (10 mL) was added and the resulting reaction mixture was extracted with diethyl ether (2×50 mL). The combined organic fractions were washed with water (1×50 mL) dried over anhydrous magnesium sulfate and the solvent was evaporated under reduced pressure. The residue was subjected to MPLC (80 psi, 50 cm×1.2 cm) being eluted with 5% ethyl acetate in toluene to afford 52.1 mg of Compound 11a (66% yield) and 16.4 mg of Compound 12a (21% yield).

Physical Data (Compound 11a):
$[\alpha] \cong = +54.7° +/- 2.0°$ (c=1.05, CHCl$_3$);
m.p.=155°–157° (acetone, prisms);
Rf=0.6 (50% ethyl acetate in toluene);
NMR (300 MHz, CDCl$_3$):6.04–5.92 (m, 1H, olefinic CH), 5.22–5.05 (m, 1H, olefinic CH$_2$), 4.11 (m, 1H, 32-CHOH), 3.22 (m, 1H, 3-CHOH), 2.2–0.85 (m, 28H), 1.01 (s, 3H, CH$_3$), 1.00 (s, 3H, CH$_3$), 0.90 (d, J=6.5 Hz, 3H, 21-CH$_3$), 0.87 (d, J=6.8 Hz, 6H, 26—CH$_3$ and 27—CH$_3$), 0.82 ) (s, 30—CH$_3$), 0.71 (s, 3H, 18-CH$_3$);
IR (CHCl$_3$ solution, cm$^{-1}$): 3600 (m, OH), 3470 (bw, OH), 2950 (s, CH sat), 2870 (s CH sat), 1465 (m), 1375 (m), 1115 (m), 990 (m), 920 (m);
MS (EI):452 (1%, M —H$_2$O), 437 (1%, M —H$_2$O, —CH$_3$), 413 (100%, M —C$_3$H$_4$OH), 395 (45%, M —C$_3$H$_4$OH, —C$_6$H$_5$COOH);
HRMS for C$_{32}$H$_{52}$O (M —H$_2$O): calculated 452.4018, found 452.3999;
EA for C$_{32}$H$_{54}$O$_2$: calculated, C 81.64%, H 11.56%; found, C 81.63%, H 11.46%.

Physical Data (Compound 12a):
$[\alpha]^{25} = +49.2° +/- 4.8°$ (c=0.42, CHCl$_3$);
m.p.=133°–135° (powder);
Rf=0.6 (50% ethyl acetate in toluene);
NMR (300 MHz, CDCl$_3$): 5.93–5.78 (m, 1H, olefinic CH), 5.16–5.01 (m,2H, olefinic CH$_2$), 4.10 (m, 1H, 32-CHOH), 3.25 (dd, J=11.3 Hz, 4.7 Hz, 1H, 3CHOH), 2.32 (m, 1H), 2.18–0.85 (m, 27H), 1.07 (s, 3H, CH$_3$), 1.02 (s, 3H, CH$_3$), 0.92 (d, J=6.3 Hz, 3H, 21-CH$_3$), 0.88 (d, J=6.6 Hz, 6H, 26-CH$_3$ and 27-CH$_3$), 0.84 (s, 3H, 31-CH$_3$), 0.74 (s, 3H, 18-CH$_3$);
IR (KBr wafer, cm$^{-1}$): 3470 (broad, OH), 2950 (s, CH sat), 2930 (s CH sat), 2865 (s, CH sat), 2855 (s, CH sat), 1470 (m), 1375 (m), 920 (m);
MS (EI): 408 (30%, M, —2H$_2$O, —CH$_3$), 395 (100%, M —C$_3$H$_4$OH, —H$_2$O);
HRMS for C$_{30}$H$_{47}$ (M —2H$_2$O, —CH$_3$): calculated 408.3756, found 408.3715;
EA for C$_{32}$H$_{54}$O$_2$: calculated, C 81.64%, H 11.56%; found, C 81.73%, H 11.60%.

I. Preparation of 3β-benzoyloxy-lanost-7-en-32-aldoxime (Compound 14b)

Hydroxylamine hydrochloride (250 mg, 3.60 mmol) was added to 3β-benzoyloxy-lanost-7-en-32-al (Compound 7b) (98 mg, 179 µmol) in anhydrous pyridine (10 mL). The mixture was stirred for 16 hr, diluted with diethyl ether (30 mL), and washed with aqueous hydrochloric acid 1N (2×50 mL). The aqueous layer was reextracted with diethyl ether (30 mL) and the combined organic layers were washed with 10% cupric sulfate (3×30 mL), water (30 mL) and brine (30 mL), dried over anhydrous magnesium sulfate and evaporated under reduced pressure, giving 105 mg of Compound 14b.

Physical Data (Compound 14b):
$[\alpha]^{25} = +30.4° +/- 2°$ (c=1.02, CHCl$_3$);
m.p.=200°–202° (acetone, needles);
Rf=0.5 (toluene);
NMR (300 MHz, CDCl$_3$):8.05 (d, J=7.8 Hz,2H, phenyl), 7.78 (s, 1H, 32-CH=NOH), 7.60–7.40 (m, 3H, phenyl), 7.18 (bs, 1H, 32-CH=$_{NOH}$), 5.42 (m, 1H, 7-CH), 4.77 (dd, J=11.0 Hz, 4.1 Hz, 1H, 3-CHOR), 2.2–0.85 (m, 25H), 1.14 (s, 3H, 31-CH$_3$), 0.97 (s, 3H, CH$_3$), 0.95 (s, 3H, CH$_3$), 0.90 (d, J=6.6 Hz, 3H, 21-CH$_3$) 0.88 (d, J=6.6 Hz, 6H, 26-CH$_3$ and 27-CH$_3$), 0.74 (s, 3H, 18-CH$_3$);
IR (CHCl$_3$ solution, cm$^{-1}$):3570 (m, OH), 3280 (bm, OH), 2950 (s, CH sat), 2860 (s CH sat), 1710 (s, C=O), 1600 (m), 1580 (m), 1470 (s), 1450 (s), 1315 (s), 1280 (vs), 1115 (s), 970 (s);
MS (EI): 516 (10%, M, —H$_2$O, —HCN), 403 (14%, M —H$_2$O, —HCN, —C$_8$H$_{17}$), 379 (20%, M —H$_2$O, 13 HCN, —C$_6$H$_5$COOH, —CH$_3$), 105 (100%, C$_6$H$_5$CO+);
HRMS for C$_{36}$H$_{52}$O$_2$ (M —H$_2$O, —HCN): calculated 516.3967, found 516.3932.

Physical Data (Compound 14a; 96% yield from Compound 7a):
$[\alpha]^{25} = -56.6° +/- 2.0°$ (c=1.06, CHCl$_3$);
m.p.=193°–196° (ethanol, flakes); Rf=0.5 (toluene);
NMR (300 MHz, CDCl$_3$):8.05 (d, J=7.8 Hz,2H, phenyl), 7.60–7.40 (m, 3H, phenyl), 7.33 (s, 1H, 32-CHNOH), 7.05 (bs, 1H, 32-CHNOH), 4.75 (dd, J=11.6 Hz, 4.2 Hz, 1H, 3-CHOR), 2.22–0.85 (m, 26H), 1.10 (s, 3H, CH$_3$), 1.06 (s, 3H, CH$_3$), 0.95 (s, 3H, CH$_3$), 0.89 (d, J=6.6 Hz, 3H, 21-CH$_3$), 0.87 (d, J=6.6 Hz, 6H, 26-CH$_3$ and 27-CH$_3$), 0.77 (s, 3H, 18-CH$_3$);
IR (KBr wafer, cm$^{-1}$): 3280 (gm, OH), 2950 (s, CH sat), 2870 (s CH sat), 1718 (s, C=O), 1600 (w), 1580 (w), 1465 (m), 1450 (m), 1310 (m), 1270 (vs), 1110 (s);
MS (EI):544 (100%, M—OH), 406 (70%, M —H$_2$O, —HCN, —C$_6$H$_5$COOH), 380 (25%, M —H$_2$O, —CN, —CH$_3$, —C$_6$H$_6$COOH), 379 (75%, M —H$_2$O, —HCN, —CH$_3$, —C$_6$H$_5$COOH), 105 (71%, C$_6$H$_5$CO+);
HRMS for C$_{37}$H$_{54}$NO$_2$ (M —OH): calculated 544.4155, found 544.4252.

Physical Data (Compound 14c; 70% yield from Compound 7c):
$[\alpha]^{25} = -77.9° +/- 2.0°$ (c=1.00, CHCl$_3$);
m.p.=204°–205° (acetone, needles);
Rf=0.5 (toluene);
NMR (300 MHz, CDCl$_3$): 8.05 (d, J=7.5 Hz,2H, phenyl), 7.78 (s, 1H, 32-CHNOH), 7.60–7.40 (m, 3H, phenyl), 5.68 (d, J=10.2 Hz, 1H, olefinic H), 5.57 (d, J=10.2 Hz, 1H, olefinic H), 4.75 (dd, J=11.5 Hz, 4.8

Hz, 1H, 3-CHOR), 2.43 (m, 1H), 2.18 (m, 1H), 1.95–0.85 (m, 22 ), 1.03 (s, 3H, CH$_3$), 0.97 (s, 3H, CH$_3$), 0.92–0.88 (m 12H, CH$_3$s), 0.86 (s, 3H, 18-CH$_3$); IR (KBr wafer, cm$^{-1}$): 3280 (bm, OH), 2950 (s, CH sat), 2930 (s CH sat), 2860 (s, CH sat), 1718 (s, C=O), 1600 (w), 1580 (w), 1465 (m), 1460 (m), 1310 (m), 1275 (vs), 1110 (s);

MS (EI):561 (6%, M+), 544 (15%, M –OH), 421 (20%, M –H$_2$O, –C$_6$H$_5$COOH), 406 (33%, M –H$_2$O, –C$_6$H$_5$COOH, –CH$_3$);

HRMS for C$_{37}$H$_{55}$NO$_3$ (M+): calculated 561.4182, found 561.4135.

J. Preparation of lanost-7-en-32-alkoxime-3β-ol (Compound 15b)

Potassium hydroxide (6.5 g) in ethanol (48 mL) and water (3 mL) was added to a solution of 3β-benzoyloxy-lanost-7-en-32-aldoxime (Compound 14b) (218 mg, 389 μmol) in ethanol (50 mL) which had been warmed to 50°. The mixture was stirred at 50° for 2 hr, then cooled and quenched with water (200 mL). The reaction mixture was extracted with dichloromethane (3×100 mL) and the combined organic extracts were dried over anhydrous magnesium sulfate, filtered and subjected to evaporation under reduced pressure. The resulting residue was subjected to MPLC (50 psi, 50 cm×1.8 cm), being eluted with 10% ethyl acetate in toluene, giving 168 mg (94%) of Compound 15b.

Physical Data (Compound 15d):
[α]$^{25}$ = –2.0°+/–2.0° (c=1.00, CHCl$_3$);
m.p.=212.5°–214.5° (ethanol-water);
Rf=0.55 (50% ethyl acetate in toluene);
NMR (300 MHz, CDCl$_3$); 7.77 (s, 1H, 32-CH=NOH), 7.40 (bs, 1H, 32-CH=NOH), 5.41 (m, 1H, 7-CH), 3.26 (dd, J=10.7 Hz, 5.0 Hz, 1H, 3-CHOH), 2.10–0.85 (m, 26H), 0.99 (s, 3H, CH$_3$), 0.90–0.86 (m, 15H, rest of CH$_3$), 0.72 (s, 3H, 18-CH$_3$);
IR (CHCl$_3$ solution, cm$^{-1}$):3560 (m, OH), 3300 (bm, OH), 2950 (s, CH sat), 2860 (s CH sat), 1470 (s), 1380 (s);
MS (EI):440 (100%, M –OH), 412 (52%, M –H$_2$O, –HCN), 406 (33%, M –2H$_2$O, –CH$_3$), 397 (49%, M –H$_2$O, –HCNCH$_3$), 379 (34%, M –2H$_2$O, –HCN, 13 CH$_3$);
HRMS for C$_{30}$H$_{50}$NO (M –OH): calculated 440.3892, found 440.3885;
EA for C$_{30}$H$_{51}$NO$_2$: calculated, C 78.72%, H 11.23%, N 3.06%; found, C 78.50%, H$_{11.29}$%, N 2.95%.

Physical Data (Compound 15a; yield >95% from Compound 14a):
[α]$^{25}$ = –87.2°+/–2.0° (C=1.09, CHCl$_3$);
m.p.=226°–229° (acetone, needles);
Rf=0.55 (50% ethyl acetate in toluene);
NMR (300 MHz, CDCl$_3$): 7.30 (s, 1H, 32-CH=NOH), 7.18 (bs, 1H, 32-CH=NOH), 3.25 (dd, J=11.1 Hz, 4.3 Hz, 1H, 3-CHOH), 2.20–0.85 (m, 27H), 1.02 (s, 3H, CH$_3$), 0.99 (s, 3H, CH$_3$), 0.88 (d, J=6.6 Hz, 3H, 21-CH$_3$), 0.87 (d, J=6.6 Hz, 6H, 26-CH$_3$ and 27-CH$_3$), 0.82 (s, 3H, CH$_3$), 0.76 (s, 3H, 18-CH$_3$);
IR (CHCl$_3$ solution, cm$^{-1}$):3850 (m, OH), 3340 (bw, OH), 2950 (s, CH sat), 2930 (s CH sat), 2870 (s, CH sat), 1465 (m), 1455 (m), 1375 (m);
MS (EI): 440 (65%, M –OH), 412 (28%, M –H$_2$O, –HCN), 397 (22%, M –H$_2$O, –HCN, –CH$_3$), 394 (31%, M –2H$_2$O, –HCN), 380 (29%, M –H$_2$O, –CN, –CH$_3$), 379 (94%, M –2H$_2$O, –HCN, –CH$_3$);
HRMS for C$_{30}$H$_{50}$NO (M –OH): calculated 440.3892, found 440.3885;
EA for C$_{30}$H$_{51}$NO$_2$: calculated, C 78.72%, H 11.23%, N 3.06%; found, C 78.90%, H 11.32%, N 2.87%.

Physical Data (Compound 15c; yield 89% from Compound 14c):
[α]$^{25}$ = –109.1°+/–2.0° (c=0.92, CHCl$_3$);
m.p.=198°–200° (powder);
Rf =0.55 (50% ethyl acetate in toluene);
NMR (300 MHz CDCl$_3$): 7.76 (s, 1H, 32-CH=NOH), 5.67 (d, J=10.1 Hz, 1H, olefinic H), 5.54 (d, J=10.1 Hz, 1H, olefinic H), 3.25 (dd, J=11.3 Hz, 4.8 Hz, 1H, 3-CHOH), 2.39 (m, 1H), 2.17 (m, 1H), 1.96–0.85 (m, 23H), 1.02 (s, 3H, CH$_3$), 0.91 (s, 3H, CH$_3$), 0.89–0.85 (m, 12H, CH$_3$s), 0.79 (s, 3H, 18-CH$_3$);
IR (CHCl$_3$ solution, cm$^{-1}$): 3580 (m, OH), 3360 (bw, OH), 2950 (s, CH sat), 2930 (s CH sat), 2865 (s, CH sat), 1465 (m), 1380 (m), 1365 (m);
MS (EI):440 (6%, M –OH), 406 (7%, M –H$_2$O, –CH$_3$), 379 (6%, M –2H$_2$O, –HCN, –CH$_3$);
HRMS for C$_{30}$H$_{50}$NO (M –OH): calculated 440.3892, found 440.3895;
EA for C$_{30}$H$_{51}$NO$_2$: calculated, C 78.72%, H 11.23%, N 3.06%; found, C 78.69%, H 10.88%, N 2.82%.

K. Preparation of 3β-benzoyloxy-4,4-dimethyl-5α,14β-cholest-8-en-15-one (Compound 40a)

To a solution of 3β-benzoyloxy-4,4-dimethyl-5α-cholest-8,14-diene (5.0 g, 10.2 mmol) in diethyl ether solution (300 mL) and 0.5M aqueous sodium bicarbonate (300 mL) was added meta-chloro-perbenzoic acid (2.44 g, 11.3 mmol) (Aldrich). After 30 min, the ether fraction was separated from the sodium bicarbonate layer and the aqueous fraction was repeatedly extracted with diethyl ether (5×500 mL). The organic fractions were combined, washed with brine (1×100 mL), dried over magnesium sulfate, filtered, and concentrated in vacuo to about 150 ml. This ether solution of 38a was promptly cooled (0°) and treated dropwise with boron trifluoride etherate (26 mL, 22.5 mmol (Aldrich). After 30 min, the reaction was quenched with ice water (200 mL) and the aqueous phase was reextracted with ether (3×100 mL). The combined ether fractions were extracted with saturated sodium bicarbonate solution (1×200 mL), dried over anhydrous magnesium sulfate, filtered, and concentrated in vacuo. The residue was crystallized from isopropanol (75 mL) to afford 4.10 g of 3β-benzoyloxy-4,4-dimethyl-5β-cholest-8-en-15-one (Compound 40a) in 75% yield.

Physical Data (Compound 40a):
[α]$^{25}$ = –21.9°+/–5.0° (c=0.40, CHCl$_3$);
m.p.=154°–155° (isopropanol);
Rf=0.75 (5% ethyl acetate in hexanes);
NMR (300 MHz, CDCl$_3$):8.05 (d, J=7.2 Hz,2H, phenyl), 7.60–7.40 (m, 3H, phenyl), 4.80 (dd, J=11.1 Hz, 4.5 Hz, 1H, 3-CHOR), 2.60–0.85 (m 25H), 1.08 (s, 3H, 31-CH$_3$), 1.07 (s, 3H, 19-CH$_3$), 1.02 (d, J=6.3 Hz, 3H, 21-CH$_3$), 1.00 (s, 3H, 30-CH$_3$), 0.97 (s, 3H, 18-CH$_3$), 0.89 (d, J=6.6 Hz, 6H, 26-CH$_3$ and 27-CH$_3$);
HRMS for C$_{36}$H$_{52}$O$_3$ (M+): calculated 532.3917, found 532.3923.

L. Preparation of 3β-benzoyloxy-lanost-8-en-15-one (Compound 29a)

To a 0.5M solution of potassium tertiary butoxide in tertiary butanol (72 mL, 37.6 mmol) as added 3β-benzoyloxy-4,4-dimethyl-5α,14β-cholest-8-en-15-one (Compound 40a) (2.0 g, 3.76 mmol) in anhydrous tetrahydrofuran (5.0 mL) rapidly followed by the addition of methyl iodide (2.24 mL, 35.8 mmol). After 15 min the reaction mixture was poured into ice cold water (50 mL), extracted with toluene:ethyl acetate (1:1) (4×200 mL), and the combined organics were washed with saturated sodium chloride (100 mL), dried over anhydrous magnesium sulfate, filtered, and concentrated in vacuo. The resultant residue was crystallized from isopropanol (75 mL) to provide 1.40 g of pure 3β-benzoyloxylanost-8-en-15-one (Compound 29a) in 68% yield.

Physical Data (Compound 29a):
m.p.=199°–200° (ethyl acetate-methanol);
Rf=0.77 (5% ethyl acetate in hexanes);
NMR (300 MHz, CDCl$_3$); 8.05 (m,2H, phenyl), 7.60–7.40 (m, 3H, phenyl), 4.75 (dd, J=11.1 Hz, 4.5 Hz, 1H, 3-CHOR), 2.80–0.85 (m, 24H), 1.12 (s, 3H, 32-CH$_3$), 1.06 (s, 6H, 19-CH$_3$ and 31-CH$_3$), 0.98 (d, J=6.3 Hz, 3H, 21-CH$_3$), 0.97 (s, 3H, 30-CH$_3$), 0.87 (d, J=6.6 Hz, 6H, 26-CH$_3$ and 27-CH$_3$), 0.78 (s, 3H, 18-CH$_3$);
HRMS for C$_{37}$H$_{54}$O$_3$ (M+): calculated 546.4074, found 546.4137.

L1. Preparation of
3β-benzoyloxy-32-benzyloxylanoxy-8-en-15-one (Compound 47a)

The same procedure as used for the preparation of Compound 29a was employed with the following exceptions: Compound 40a was added in benzene rather than tetrahydrofuran; benzyl chloromethyl ether prepared by the method of Conner (D. S. Conner, G. W. Klein, G. N. Taylor, Org. Syn., 52:16-19 (1972)) was utilized instead of methyl iodide; and resultant reaction mixture was chromotographed (hexane:ethylacetale, 98:2) instead of crystallized directly. Compound 47a, in a 64% yield, resulted.

Physical Data (Compound 29a):
[α]$^{25}$=+84.9°±2.0° (c=1.02, CHCl$_3$);
m.p.=49°–50° (methanol);
Rf=0.37 (5% ethyl acetate in hexanes);
NMR (300 MHz, CDCl$_3$): 8.05 (d, J=7.2 Hz,2H, phenyl), 7.60–7.40 (m, 3H, phenyl), 7.40–7.20 (m, 5H, phenyl), 4.76 (dd, J=11.3 Hz, 4.4 Hz, 1H, 3-CHOR), 4.48 (d, J=12.3 Hz, 1H, OCH$_2$Ph), 4.40 (d, J=12.3 Hz, 1H, OCH$_2$Ph), 3.69 (d, J=9.3 Hz, 1H, 32-CH$_2$OR), 3.40 (d, J=9.3 Hz, 1H, 32-CH$_2$OR), 2.70–2.45 (m,2H, 16-CH$_2$), 2.15–0.85 (m, 22H), 1.05 (s, 6H, 19-CH$_3$ and 31-CH$_3$), 0.98 (s, 3H, 30-CH$_3$) 0.96 (d, J=6.3 Hz, 3H, 21-CH$_3$), 0.84 (d, J=6.6 Hz, 6H, 26-CH$_3$ and 27-CH$_3$), 0.77 (s, 3H, 18-CH$_3$);
IR (CHCl$_3$ solution, cm$^{-1}$): 2850 (s, CH sat), 2883 (s, CH sat), 1739 (s, C=O), 1716 (s, C=O), 1452 (s), 1274 (s), 1113 (s);
MS (EI): 652 (9%, M+), 409 (79%, M—PhCOOH, —CH$_2$OCH$_2$Ph), 105 (100%, C$_6$H$_5$CO+);
HRMS for C$_{44}$H$_{60}$O$_4$ (M+): calculated 652.4493, found 652.4549.

M. Preparation of
3β-benzoyloxy-14α-cyano-4,4-dimethyl-5α-cholest-8-ene (Compound 16a)

Phenyl isocyanate (35 μL, 322 μmol) was added to 3β-benzoyloxy-lanost-8-en-32-aldoxime (Compound 14a) (72.5 mg, 129 μmol) and triethylamine (5 drops) in azeotropically dried benzene (8 mL) at room temperature. The mixture was stirred at reflux for 1.5 hr. The cooled reaction mixture (room temperature) was quenched with water (40 mL) and extracted with dichloromethane (3×100 mL). The combined organic extracts were dried over anhydrous magnesium sulfate, filtered, and the solvent evaporated under reduced pressure. The residue was subjected to MPLC (70 psi, 50 cm×1.8 cm), using toluene as the eluting solvent, to afford 59.7 mg 85%) of Compound 16a.

Physical Data (Compound 16a):
[α]$^{25}$=+15.0°+/−2.0° (c=1.04, CHCl$_3$);
m.p.=211.5°–213.5° (acetone, very fine needles);
Rf=0.6 (toluene);
NMR (300 MHz, CDCl$_3$):8.06 (d, J=7.2 Hz,2H, phenyl), 7.60–7.40 (m, 3H, phenyl), 4.76 (dd, J=11.1 Hz, 4.5Hz, 1H, 3-CHOR), 2.35–0.85 (m, 26H), 1.08 (s, 3H, CH$_3$), 1.07 (s, 3H, CH$_3$), 0.99 (s, 3H, CH$_3$), 0.96 (d, J=6.3 Hz, 3H, 21-CH$_3$), 0.88 (d, J=6.6 Hz, 6H, 26-CH$_3$ and 27-CH$_3$), 0.74 (s, 3H, 18-CH$_3$);
IR (KBr wafer, cm$^{-1}$): 2950 (s, CH sat), 2865 (s, CH sat), 2220 (w, CN), 1715 (s, C=O), 1465 (m), 1450 (m), 1275 (vs), 1115 (m);
MS (CI): 543 (3%, M+), 517 (20%, M —CN), 395 (33%, M —CN, C$_6$H$_6$COOH);
HRMS (isobutane CI) for C$_{37}$H$_{53}$NO$_2$ (M+): calculated 543.4076, found 543.4055.

N. Preparation of
14α-cyano-4,4-dimethyl-5α-cholest-8-en-3β-ol (Compound 17a)

3β-benzoyloxy-14α-cyano-4,4-dimethyl-5α-cholest-8-ene (Compound 16a) (45.3 mg, 83.4 μmol) was dissolved in 1N ethanolic potassium hydroxide (30 mL) containing 5% water at room temperature. The mixture was stirred for 30 min at 50°, poured into ice water (200 mL) and extracted with dichloromethane (3×200 mL). The combined extracts were dried over anhydrous magnesium sulfate and solvent removed by evaporation under reduced pressure. The residue was subjected to MPLC (80 psi, 50 cm×1.2 cm), using 8% ethyl acetate in toluene as the eluting solvent, to afford 33.0 mg (90%) of Compound 17a.

Physical Data (Compound 17a):
[α]$^{25}$=−9.5°+/−2.0° (C=1.08, CHCl$_3$);
m.p.=167.5°–169° (powder);
Rf=0.6 (50% ethyl acetate in toluene);
NMR (300 MHz, CDCl$_3$): 3.27 (dd, J=11.3 Hz, 4.4 Nz, 1H, 3-CHOH), 2.3–0.85 (m, 26H), 1.02 (s, 3H, CH$_3$), 1.01 (s, 3H, CH$_3$), 0.95 (d, J=6.3 Hz, 3H, 21-CH$_3$), 0.88 (d, J=6.6 Hz, 26-CH$_3$ and 27-CH$_3$), 0.83 (s, 3H, 30-CH$_3$), 0.73 (s, 3H, 18-CH$_3$);
IR (CHCl$_3$ solution, cm$^{-1}$): 3610 (m, OH), 3840 (bw, OH), 2960 (s, CH sat), 2940 (s, CH sat), 2870 (s, CH sat), 2220 (w, CN), 1465 (m), 1380 (m);
MS (EI): 439 (14%, M+), 424 (14%, M —CH$_3$), 406 (100%, M —CH$_3$, —H$_2$O), 397 (44%, M —HCN, CH$_3$);
HRMS (EI) for C$_{30}$H$_{49}$NO (M+): calculated 439.3814, found 439.3852;
EA for C$_{30}$H$_{49}$NO: calculated, C 81.94%, H 11.23%, N 3.19%; found, C 82.15%, H 11.28%, N 3.15%.

N1. Preparation of 3β-acetoxy-lanost-8-en-32-al (Compound 43a)

Acetic anhydride (2 mL) was added to a solution of lanost-8-en-32-al-3β-ol (prepared as described by Shafiee et al., J. Lipid Res., 27:1–10 (1986)) (Compound 10a) (208 mg, 471 μmol) in anhydrous pyridine (4 mL) at room temperature. After stirring for 17 hours at room temperature the mixture was poured into water (25 mL) and extracted with diethyl ether (3×40 mL). The combined organic fractions were washed with 1N hydrochloric acid (50 mL), 10% aqueous cupric sulfate (50 mL), water (50 mL) and brine (50 mL), dried over anhydrous magnesium sulfate and evaporated under reduced pressure giving 226 mg (<95%) of Compound 43a.

Physical Data (Compound 43a):

$[\alpha]^{25} = -258.7° +/- 2.0°$ (c=0.95, CHCl$_3$);

m.p. = 167.5°–169° (methanol/acetone 1:1);

Rf=0.6 (25% ethyl acetate in toluene);

NMR (300 MHz, CDCl$_3$): 9.44 (s, 1H, 32-CHO), 4.47 (dd, J=11.6 Hz, 4.4 Hz, 1H, 3-CHOR), 2.35–0.85 (m, 26H), 2.06 (s, 3H, acetate), 1.08 (s, 3H, CH$_3$), 0.90 (s, 3H, CH$_3$), 0.89 (d, J=6.5Hz, 3H, 21-CH$_3$), 0.86 (a, 3H, CH$_3$), 0.86 (d, J=6.5Hz, 6H, 26-CH$_3$ and 27-CH$_3$), 0.75 (s, 3H, 18-CH$_3$);

IR (CHCl$_3$ solution, cm$^{-1}$): 2955 (s, CH sat), 2865 (s, CH sat), 1725 (s, C=O), 1465 (m), 1365 (m), 1255 (s), 1025 (m);

MS (EI): 455 (42%, M—CHO), 395 (100%, M—CHO, —CH$_3$COOH);

HRMS for C$_{31}$H$_{51}$O$_2$ (M—CHO: calculated 455.3890, found 455.3900.

N2. Preparation of 3β-acetoxy-lanost-8-en-32-aldoxime (Compound 44a)

Hydroxylamine hydrochloride (300 mg, 4.32 mmol) was added to 3β-acetoxy-lanost-8-en-32-al (Compound 43a) (205 mg, 424 μmol) in anhydrous pyridine (5 mL). The mixture was stirred at 40° for 16 hours, poured into water (50 mL) and extracted with diethyl ether (3×40 mL). The combined organic layers were washed with 1N hydrochloric acid, 10% aqueous cupric sulfate, water and brine (50 mL each), dried over anhydrous magnesium sulfate and evaporated under reduced pressure giving 210 mg (95%) of Compound 44a.

Physical Data (Compound 44a):

$[\alpha]^{25} = -105.5° +/- 2.0°$ (c=1.05, CHCl$_3$);

m.p. = 167.5°–169° (powder from evaporation of acetone);

Rf=0.6 (25% ethyl acetate in toluene);

NMR (300 MHz, CDCl$_3$): 7.30 (s, 1H, 32-CH=NOH), 4.49 (dd, J=11.6 Hz, 4.4 Hz, 1H, 3-CHOR), 2.20–0.85 (m, 27H), 2.06 (s, 3H, acetate), 1.04 (s, 3H, CH$_3$), 0.89–0.85 (m, 15H CH$_3$s), 0.75 (s, 3H, 18-CH$_3$);

IR (CHCl$_3$ solution, cm$^{-1}$): 3850 (v,), 3300 (bw), 2950 (s, CH sat), 2865 (s, CH sat), 1720 (s, C=O), 1465 (m), 1375 (m), 1260 (s), 1030 (m).

O. Preparation of 3β-benzoyloxy-15α-fluoro-lanost-7-ene (Compound 24b)

Diethylamino sulfur trifluoride (DAST, 5.75 mL, 46 mmol was added to a solution of 3β-benzoyloxylanost-7-en-15α-ol (Compound 22b, 1.6 g, 2.92 mmol) in dry (distilled from phosphorous pentoxide) dichloromethane (100 mL) under argon at −78°. The reaction was stirred at −78° for 0.5 hr, then diluted with dichloromethane (100 mL). Aqueous sodium bicarbonate was added until the aqueous phase was neutral and the mixture as extracted with toluene:ethyl acetate 1:1 (3×100 mL). The combined organic solutions were dried over anhydrous magnesium sulfate, filtered, and solvents removed in vacuo to give 1.7 g of a complex mixture.

Purification by chromatography on silica gel (eluant 5% ethyl acetate in hexane), followed by HPLC on silica gel (eluant 25% toluene in hexane) yielded 294 mg (18% yield) of 3β-benzoyloxy-15α-fluoro-lanost7-ene (Compound 24b).

Physical Data (Compound 24b):

$[\alpha]^{25} = +45.9° +/- 2.0°$ (c=1.06, CHCl$_3$);

m.p. = 226°–227° (powder);

Rf=0.50 (5% ethyl acetate in hexane); 0.15 (25% toluene in hexane);

NMR (300 MHz, CDCl$_3$): 8.06 (d, J=7.4 Hz, 2H, phenyl), 7.55 (m, 1H, phenyl), 7.45 (m, 2H, phenyl), 5.51 (m, 1H, 7-CH), 5.05 (dd, J=56.6, 9.2, 5.6 Hz, 1H, 15-CHF), 4.78 (dd, J=9.4, 5.6 Hz, 1H, 3-CH), 2.18–1.27 (m, 23H), 1.15 (s, 3H, 31-CH$_3$), 1.10 (d, J=3.6 Hz, 3H, 32-CH$_3$), 0.95 (s, 3H, CH$_3$), 0.94 (s, 3H, CH$_3$), 0.87 (unresolved d, 9H, 21, 26, 27-CH$_3$), 0.70 (s, 3H, 18-CH$_3$);

IR (KBr, cm$^{-1}$): 2960 (s, CH sat), 1705 (s, C=O), 1460 (m), 1450 (m), 1390 (m), 1380 (m), 1365 (m), 1280 (s, C-O), 1120 (m, C-F), 1035 (m), 1025 (m); MS (EI): 550 (20%, M+), 413 (100%, M —C$_8$H$_9$O$_2$); HRMS for C$_{37}$H$_{55}$O$_2$F (M+): calculated 550.4186, found 550.4163.

Physical Data (Compound 25b; 32% yield from Compound 23b):

$[\alpha]^{25} = +19.0° +/- 2.0°$ (c=1.02, CHCl$_3$);

m.p. = 202°–203° (powder);

Rf=0.42 (1:1, toluene:hexane);

NMR (300 MHz, CDCl$_3$): 8.05 (d, J=7.4 Hz, 2H, phenyl), 7.55 (m, 1H, phenyl), 7.45 (m, 2H, phenyl), 5.45 (m, 1H, 7-CH), 5.05 (ddd, J=56.8, 9.3, 5.5Hz, 1H, 15-CHF), 4.95 (m, 1H), 2.1–1.0 (m, 25H), 1.15 (d, J=3.5Hz, 3H, 32-CH$_3$), 0.90 (m, 12H, CH$_3$), 0.75 (s, 3H, 18-CH$_3$);

19F NMR (188.2 MHz, CDCl$_3$): −193.2 (dd, 56.6, 27.8 Hz);

IR (KBr, cm$^{-1}$): 2960 (m), 2930 (m, CH sat), 1710 (s, C=O), 1460 (m), 1450 (m), 1390 (m), 1380 (m), 1365 (m), MS (EI): 522 (10%, M+), 385 (95%, M —C$_8$H$_9$O$_2$); HRMS for C$_{35}$H$_{51}$O$_2$F (M+): calculated 522.3873, found 522.3873.

P. Preparation of 15α-fluoro-lanost-7-en-3β-ol (Compound 26b)

Lithium aluminum hydride (290 mg, 7.6 mmol) was added slowly to a solution of 3β-benzoyloxy-15α-fluoro-lanost-7-ene (Compound 24b, 294 mg, 0.534 mmol) in diethyl ether (40 mL) and tetrahydrofuran (10 mL) at 0° under nitrogen. The reaction was stirred for 10 min, then quenched with sodium sulfate decahydrate (1 g) addition. The mixture was diluted by the addition of diethyl ether (50 mL). Then, ethyl acetate (20 mL) was added, the solution filtered through a sintered glass funnel and the solvents removed in vacuo. The resulting solid was crystallized from isopropanol to give 230 mg (96% yield) of a 15α-fluoro-lanost-7-en-3β-ol (Compound 26b). The crystals had a m.p.=159°–160°, and the NMR showed co-crystallization with isopropanol (2:1, 26b:isopropanol). The crystals were then dissolved in benzene and the solvent removed to give an amorphous solid.

Physical Data (Compound 26b):

$[\alpha]^{25} = +24.6° +/- 4.0°$ (c=0.5, CHCl$_3$);

m.p. = 172.5°–173° (powder);

Rf=0.18 (1:2:7 ethyl acetate:toluene:hexane);

NMR (300 MHz, CDCl$_3$): 5.50 (m, 1H, 7-CH), 5.05 (ddd, J=56.6, 9.2, 5.6 Hz, 1H, 15β-CHF), 3.27 (dd, J=10.6, 4.9 Hz, 1H, 3-CH), 2.18–1.27 (m, 23H), 1.10 (d, J=3.6 Hz, 32-CH$_3$), 1.01 (s, 3H, CH$_3$), 0.92–0.87 (m, 12H, CH$_3$s), 0.71 (s, 3H, 18-CH$_3$);

19F NMR (188.2 MHz, CDCl₃):—192.9 (dd.q, 56.6, 27.5, 3.6 15-CHF);

IR (CHCl₃, cm⁻¹):3620 (w, OH), 2960 (s), 2935 (s), 2870 (m, CH sat), 1467 (m), 1448 (m), 1384 (m), 1367 (m), 1090 (w, CF), 1028 (m), 995 (m), 670 (m);

MS (EI): 446 (65%, M+), 431 (40%, M —CH₃), 413 (50%, M —CH₃, —H₂O), 306 (100%, M —C₉H₁₆O);

HRMS for C₃₀H₅₁OF (M+): calculated 446.3924, found 446.3917;

EA for C₃₀H₅₁OF: calculated, C 80.66%, H 11.51%, F 4.25%; found, C 80.83%, H 11.29, F 4.11%.

Physical Data (Compound 27b from Compound 25b; 93% yield):

[α]²⁵ = +15.3° +/−2.4° (c=0.85, CHCl₃);
m.p.=68°-69°;
Rf=0.11 (1:2:7 ethyl acetate:toluene:hexane);
NMR (300 MHz, CDCl₃): 5.45 (m, 1H, 7-CH), 5.05 (ddd, J=56.8, 9.3, 5.5Hz, 1H, 15-CHF), 3.62 (m, 1H, 3-CH), 2.1-1.0 (m, 25H), 1.15 (d, J=3.5Hz, 3H, 32-CH₃), 0.88 (m 9H, CH₃s), 0.83 (s, 3H, CH₃), 0.73 (s, 3H, 18-CH₃);
19F NMR (188.2 MHz, CDCl₃): 31 193.2 (dd, 56.7, 27.8 H₂);
IR (CHCl₃, cm⁻¹): 2960 (s), 2935 (s, CH sat), 1465 (m), 1445 (m), 1385 (m), 1365 (m), 1115 (w), 1035 (m), 1025 (m), 1000 (w);
MS (EI): 418 (100%, M), 403 (90%, M —CH₃);
HRMS for C₂₈H₄₇F (M+): calculated 481.3611, found 418.3592.

Q. Preparation of 3β-hydroxy-lanost-7-en-15-oxime (Compound 31b)

3β-hydroxy-lanost-7-en-15one (120 mg, 0.27 mmol) was dissolved in dry (distilled from potassium hydroxide) pyridine (3 mL) under argon. Hydroxylamine hydrochloride (Aldrich) (200 mg, 2.92 mmol) was added. The solution was heated at 80° for 18 hr. After the solution had cooled to room temperature, it was diluted with ethyl acetate and washed, in order, with water (1×50 mL), 10% hydrochloric acid (1×50 mL), water (1×50 mL), aqueous sodium bicarbonate (1×50 mL), and aqueous sodium chloride (1×50 mL). The organic layer was dried over anhydrous magnesium sulfate and filtered. The solvents were removed in vacuo. Purification of the residues by means of silica gel chromatography (eluant, 15% ethyl acetate in hexanes) gave 106 mg (85% yield) of 3β-hydroxy-lanost-7-en-15-oxime (Compound 31b).

Physical Data (Compound 31b):
[α]²⁵ = +46.0+/−2.3° (c=0.86, CHCl₃);
m.p.=185°-186° (powder);
Rf=0.26 (20% ethyl acetate in toluene);
NMR (300 MHz, CDCl₃):6.85 (m, 1H, 7-CH, 6.44 (s, 1H, 3.26 (dd, J=12, 5Hz, 1H, 3-CH), 2.76 (dd, J=18, 9 Hz, 1H), 2.28 (dd, J=20, 9 Hz, 1H), 2.1-1.1 (m, 22H), 1.21 (s, 3H, 32-CH₃), 0.99 (s, 3H, 31-CH₃), 0.94 (d, J=6 Hz, 3H, 21-CH₃), 0.88 (bs, 9H, CH₃s), 0.86 (s, 3H, CH₃), 0.70 (s, 3H, 18-CH₃);
IR (KBr, cm⁻¹): 3350 (bs, OH), 2990 (s), 2840 (s, CH sat), 1670 (w, C=N), 1470 (m), 1382 (s), 920 (m, NO);
MS (EI): 457 (5%, M+), 442 (25%, M+—CH₃), 440 (100%, M —OH);
HRMS for C₃₀H₅₁O₂N (M+): calculated 457.3920, found 457.3917;
EA for C₃₀H₅₁O₂N: calculated, C 78.72%, H 11.23%, F 3.06%; found, C 78.63%, H 10.87, F 2.76%.

R. Preparation of 14α-allyl-3β-benzoyloxy-4,4-dimethyl-5α-cholest-7-en-15-one (Compound 20b)

3β-benzoyloxy-4,4-dimethyl-5α-cholest-7-en-15-one (Compound 18) (1.13 g, 2.13 mmol) was added to a 0.5M solution of potassium in tert-butanol (45 mL) under argon at 25°. Freshly distilled ally bromide (200 μL, 2.30 mmol) was added and the solution stirred for 1 hr. The reaction mixture was quenched with aqueous ammonium chloride (100 mL) and extracted with toluene (3×100 mL). The combined organic fractions were washed with water (1×100 mL) then saturated aqueous sodium chloride (1×100 mL), dried over anhydrous magnesium sulfate, filtered and solvents removed in vacuo. The residues were purified by means of silica gel chromatography (eluant, 3:20:77, ethyl acetate:toluene:hexane) followed by HPLC (eluant, 1.5:20:78.5, ethyl acetate:toluene:hexane). Two fractions resulted: 14α-allyl-3β-benzoyloxy-4,4-dimethyl-5α-cholest-7-en-15-one (Compound 20b) 240 mg (yield 19.7%), Rf=0.39, and 7α-allyl-3β-benzoyloxy-4,4-dimethyl-5α-cholest-8(14)-en-15-one, 600 mg (yield 49.2%), Rf=0.37 (1:4:15; ethyl acetate:toluene:hexane).

Physical Data (Compound 20b):
NMR (300 MHz, CDCl₃): 8.06 (d, 7.4 Hz,2H, phenyl), 7.55 (m, 1H, phenyl), 7.45 (m,2H, phenyl), 6.51 (m, 1H, 7-CH), 5.61 (m, 1H, allyl, CH), 4.98 (m 2H, allyl, CH₂), 4.77 (dd, J=9.4, 4.6 Hz, 1H, 3-CHOR), 2.7-1.1 (m, 23H), 1.15 (s, 3H, CH₃), 0.99 (m, 9H, CH₃s), 0.91 (s, 3H, CH₃), 0.88 (s, 3H, CH₃), 0.82 (s, 3H, 18-CH₃);
HRMS for C₃₉H₅₆O₃ (M+): calculated 572.4229, found 572.4214;

R1. Preparation of 14α-allyl-3β-benzoyloxy-4,4-dimethyl-5α-cholest-8-en-5-one (Compound 20a)

The same preparative procedure as employed for Compound 20b was used, with the following exceptions: Compound 40a was utilized as the starting material, instead of Compound 18; and crude product was crystallized from ethyl acetate to give pure 14α-allyl-3β-benzoyloxy-4,4-dimethyl-5α-cholest8-en-5-one.

Physical Data (Compound 20a):
m.p.=172°-174° (ethyl acetate);
Rf=0.42 (5% ethyl acetate/hexanes);
NMR (300 MHz, CDCl₃): 8.06 (d, 7.2 Hz,2H, phenyl), 7.60-7.40 (m, 3H, phenyl), 7.75 (m, 1H, olefinic CH), 5.01 (m,2H, olefinic CH₂), 4.75 (dd, J=12, 5Hz, 1H, 3-CHOH), 2.61 (dd, J=20, 9H₂, 1H), 2.5-1.1 (m, 26H), 1.1 (s, 3H, CH₃), 1.05 (m, 3H, 26H), 1.1 (s, 3H, CH₃), 1.05 (m, 3H, CH₃), 1.00 (m, 6H), 0.9 (d, J=7 Hz, 6H, 26-CH₃ and 27-CH₃), 0.80 (s, 3H, 18-CH₃);

S. Preparation of 14α-allyl-4,4-dimethyl-5α-cholest7-en-3β-ol (Compound 21b)

Sodium (20 mg, 0.87 mmol) was added to dry (distilled from calcium hydride) diethylene glycol (3 mL) under nitrogen. Compound 20b, 14α-allyl-3β-benzoyloxy-4,4-dimethyl-5α-cholest-7-en-15-one (54 mg, 0.094 mmol) was then added followed by anhydrous hydrazine (1 mL). The solution was heated under a reflux condenser to 180° for 48 hr. The condenser was removed and the excess hydrazine was distilled off at 220°. The solution was allowed to cool to room temperature then diluted with dichloromethane and water.

The aqueous phase was neutralized by addition of 10% hydrochloric acid. The mixture was extracted with dichloromethane and the combined organic fractions were dried over anhydrous magnesium sulfate, filtered and the solvents removed in vacuo to give 25 mg of a complex mixture of 14α-allyl-4,4-dimethyl-5α-cholest-7-en-3β-ol (Compound 21b), and 7α-allyl-4,4-dimethyl-5α-cholest-8(14)-3β-01.

T. Preparation of 4,4-dimethyl-5α-cholest-8-ene-3,β,14α,15α-triol (Compound 34a)

Pyridine (6.4 mL) was added to a solution of 4,4-dimethyl-5α-cholest-8,14-diene-3β-ol. (Compound 32a) (3.25 g, 7.87 mmol) in 150 mL of benzene and the mixture was cooled to 5° C. in an ice bath. A solution of osmium tetroxide (2.1 g, 8.26 mmol) in 42 mL of dichloromethane was added dropwise to the mixture over a period of 0.5 hr and the resulting dark brown solution stirred for 1 hr at room temperature. Hydrogen sulfide gas was then bubbled through the solution for about 15 min and the black precipitates were removed by filtration through Celite (Manville Products Corps., Denver, Colo.). The filtercake was washed with diethyl ether three times and the solvents were evaporated form the filtrate to give a dark brown oil. The residue was dissolved in either and dichloromethane (9:1) and passed through a bed of silica gel with elution by diethyl ether. Evaporation of the solvents afforded a white crystalline solid and recrystallization from benzene and hexane provided 2.85 g (81% yield) of 4,4-dimethyl-5α-cholest-8-ene3β,14α-15α-triol (Compound 34a).

Physical Data (Compound 34a):
m.p. = 133°–134° (dec);
Rf=0.23 (2:3 ethyl acetate:hexane);
NMR (300 MHz, CDCl$_3$—D$_2$O (5%)):4.11 (1H, dd, J=5 Hz, 9 Hz), 3.22 (1H, dd, J=5Hz, 11 Hz), 2.33 (1H, m), 2.26 (1H, bm), 2.09 (2H, bm), 2.00–1.05 (20H, m), 1.01 (6H, d, J=3Hz), 0.87 (3H, s), 0.86 (3H, d, J=8 Hz), 0.85 (3H, s), 0.82 (3H, s), 0.69 (3H, s);
IR (Neat, cm$^{-1}$):3422 (bs, OH), 2950 (s), 1652 (s), 1465 (m), 1036 (m);
EA for C$_{29}$H$_{50}$O$_3$: calculated, C 77.97%, H 11.28%; found, C 78.05%, H 11.19.

Physical Data (Compound 35a from Compound 33a):
NMR (300 MHz, CDCl$_3$):4.11 (m, 1H), 3.61 (m, 1H), 2.50 (d, J=9.0 Hz, 1H), 2.45–0.8 (m, 26H), 1.63 (d, J=6.0 Hz, 1H), 0.98 (s, 3H), 0.87 (s, 6H), 0.85 (s, 3H), 0.71 (s, 3H);
EA for C$_{27}$H$_{46}$O$_3$: calculated, C 77.46%, H 11.08%; found, C$_{76.27}$%, H 11.15%.

U. Preparation of 3β-hydroxy-lanost-8-en-15-one (Compound 28a)

To a solution of 3β-benzoyloxy-lanost-8-en-15-one (Compound 29s) (0.25 g, 0.46 mmol) in toluene (2.5 mL) and methanol (10 mL) was added anhydrous potassium carbonate (0.7 g). After stirring for 4 hours, toluene (2.5 mL) was added followed 2 hours later by the addition of 5% potassium hydroxide in ethanol. The reaction mixture was heated to 80° for 18 hours, then diluted with water (50 mL) and repeatedly extracted with toluene:ether (1:1) (4×100 mL). The combined organic extracts were washed with saturated sodium chloride (1×100 mL), dried over anhydrous magnesium sulfate, filtered, and concentrated in vacuo. The resultant residue was purified by silica gel chromatography (10% ethyl acetate in hexanes) to afford (180 mg) 3β-hydroxy-lanost-8-en-15-one (Compound 28a) in 89% yield.

U1. Preparation of 14α-allyl-4,4-dimethyl-5α-cholest-8-en-3β-ol-15-one (Compound 45a)

The same procedure as used for Compound 28a was employed with the following exceptions: Compound 20a was used as the starting material; and the solution was stirred at 40° for 4 hours instead of 80° for 18 hours. The procedure afforded Compound 45a in a 92% yield.

Physical Data (Compound 45a):
m.p. = 139°–140° (ethyl acetate);
Rf=0.26 (ethyl acetate, 20% toluene, 70% hexanes);
NMR (300 MHz, CDCl$_3$): 5.71 (M, 1H, olefinic CH), 4.96 (m, 2H, olefinic CH$_2$), 3.24 (dd, J=12.5 Hz, 1H, 3-CHOH), 2.57 (dd, J=20H$_2$, 9 Hz, 1H), 2.4–1.1 (m, 26H), 1.01 (s, 6H, CH$_3$s), 0.97 (d, J=5Hz, 3H, 21-CH$_3$), 0.89 (d, J=7 Hz, 6H, 26-CH$_3$ and 27CH$_3$), 0.82 (s, 3H, 4α-CH$_3$), 0.76 (s, 3H, 18-CH$_3$);
MS (EI):468 (10%, m), 427 (100%, m-C$_3$H$_5$);
HRMS for C$_{32}$H$_{52}$O$_2$ (M+): calculated 468.3967, found 468.4087.

V. Preparation of 3β-hydroxy-lanost-8en-15-oxime (Compound 31a)

3β-hydroxy-lanost-8-en-15-one (Compound 28a) (180 mg, 0.41 mmol) was dissolved in anhydrous pyridine (3 mL) then treated with hydroxylamine hydrochloride (300 mg) (Aldrich). The reaction mixture was heated (85°) for 18 hours at which time an additional hydroxylamine hydrochloride (400 mg) quantity was introduced and heating continued for an additional 18 hours. After quenching the reaction with water (50 mL), and extracting with toluene:ether (1:1) (2×100 mL), the combined organics were washed with 1N hydrochloric acid (2×50 mL), water (50 mL), 10% copper sulfate solution (50 mL), water (50 mL), saturated sodium bicarbonate (50 mL), and saturated sodium chloride (50 mL), then dried over anhydrous magnesium sulfate filtered, and concentrated in vacuo. The residue was crystallized from ethyl acetate in methanol (1:1) to provide 160 mg of pure 3β-hydroxy-lanost-8-en-15-oxime (Compound 31a) in 85% yield.

Physical Data (Compound 31a):
[α]$^{25}$ = +88.7°+/−2.0° (C=1.02, CHCl$_3$);
m.p. = 187°–188° (ethyl acetate:methanol, 1:1);
Rf=0.25 (ethyl acetate in hexane);
NMR (300 MHz, CDCl$_3$): 6.90 (bs, 1H, NOH), 3.27 (dd, J=11.1 Hz, 4.5Hz, 1H, 3-CHOR), 2.77 (m,2H), 2.30 (m, 1H), 2.10 (m,2H), 1.80–0.80 (m, 24H), 1.13 (s, 3H, 14-CH$_3$), 1.02 (s, 3H, 31-CH$_3$), 0.96 (d, J=6.3 Hz, 3H, 21-CH$_3$), 0.89 (d, J=7 Hz, 6H, 26-CH$_3$ and 27-CH$_3$), 0.87 (d, J=6.6 Hz, 6H, 26-CH$_3$), 0.84 (s, 3H, 20-CH$_3$), 0.73 (s, 3H, 18-CH$_3$);
IR (CHCl$_3$, cm$^{-1}$):3600 (bw, OH), 3300 (vbm, OH), 2960 (vs, CH sat), 1470 (m), 1375 (m)(, 1035 (m), 940 (m).

V$_1$. Preparation of 14α-allyl-4,4-dimethyl-5α-cholest-8-en-3β-ol-15-oxime (Compound 46a)

The same procedure as used for Compound 31a was employed, with the following exceptions: the reaction mixture was heated at 60° for 96 hours instead of 85° for 36 hours; and Compound 45a was utilized as the starting material instead of Compound 28a. Compound 46a was provided in 40% yield.

Physical Data (Compound 45a):
m.p.=116°–117° (ethyl acetate);
Rf=0.20 (10% ethyl acetate, 20% toluene, 70% hexanes);
NMR (300 MHz, CDCl3): 8.2 (s, 1H, NOH), 5.82 (m, 1H, olefinic CH), 4.96 (m,2H, olefinic CH2), 3.24 (dd, J=12, 5Hz, 1H, 3-CHOH), 2.82 (dd, J=20H2, 9 Hz, 1 ), 2.5–1.1 (m, 26H), 1.02 (s, 6H, CH3s), 0.95 (d, J=6 Hz, 3H, 21-CH3), 0.89 (d, J=7 Hz, 6H, 26-CH3 and 27-CH3), 0.83 (s, 3H, CH3), 0.72 (s, 3H, 18-CH3);
MS (EI):465 (30%, M—H2O), 442 (90%, M—H2O—C3H5);
HRMS for C32H51NO (M —H2O): calculated 465.3971, found 465.3932.

W. Preparation of 32-benzoyloxy-lanost-8-ene-3β-15α-diol (Compound 48a).

To a cool (0°), stirred tetrahydrofuran solution (10 mL) of 3β-benzoyloxy-32-benzoyloxylanost-8-ene-15-one (Compound 47a) (1.0 g, 1.52 mmol) was added lithium aluminum hydride (Aldrich) (230 mg, 6.0 mmol) portionwise. The reaction was stirred at 0° for 1 hour then diluted with 50 mL of diethyl ether and the reaction was quenched with dropwise addition of water (ca. 1 mL). With aluminum ester hydrolysis complete, the reaction mixture as dried over anhydrous magnesium sulfate, filtered and concentrated. The resultant residue was subjected to silica gel chromatography (15% ethyl acetate in hexanes) to give 537 mg (64%) of pure Compound 48a.

Physical Data (Compound 48a):
NMR (300 MHz, CDCl3): 7.35 (m, 5H, phenyl), 4.62 (d, J=13.8 Hz, 1H, CH2Ph), 4.43 (d, J=13.8 Hz, 1H, CH2Ph), 4.38 (m, 1H, 15-CHOH), 3.90 (d, J=8.0 Hz, 1H, 32-CH2OR), 3.85 (d, J=10.0 Hz, 1H, OH), 3.60 (d, J=8.0 Hz, 1H, 32-CH2OR), 3.25 (dd, J=11.0 Hz, 4.5Hz, 1H, 3-CHOH), 2.40 (m2H), 2.00 (m, 3H), 1.80–0.85 (m, 24H), 1.08 (s, 3H, CH3), 1.03 (s, 3H, CH3), 0.92 (d, J=7.0 Hz, 6H, 26-CH3 and 27-CH3), 0.90 (d, J=7.0 Hz, 3H, 21-CH3), 0.88 (s, 3H, CH3), 0.75 (s, 3H, 18-CH3).

X. Preparation of lanost-8-ene-3β-15α,32-triol (Compound 49a)

A cold (0°) solution (tetrahydrofuran:ethanol:acetic acid: 25 mL:25 mL:1 mL) of 32-benzoyloxylanost-8-ene-3β,15α-diol (Compound 48a) (330 mg, 0.6 mmol) was degassed with nitrogen followed by the addition of 10% palladium on activated carbon (Aldrich) (75 mg). At this point, the nitrogen line was replaced with a hydrogen gas source which permitted the bubbling of hydrogen gas through the reaction mixture for 1 hour. Examination of the reaction mixture by thin layer chromatography showed complete conversion to desired triol Compound 49a. After removal of hydrogen source, the reaction was diluted with tetrahydrofuran 100 mL and filtered through celite to remove palladium. The filtered solution was concentrated and then diluted with dichloromethane (300 mL) and washed with water (3×100 mL); saturated sodium bicarbonate solution (2×50 mL), saturated sodium chloride (100 mL) and dried over magnesium sulfate then filtered and concentrated. The residue was purified by silica gel chromatography (20% ethyl acetate in hexanes) to afford 170 mg (61%) of pure Compound 49a.

Physical Data (Compound 49a):
NMR (300 MHz, CDCl3): 4.45 (dd, J=7.0 Hz, 11.0 Hz, 1H, 15-CHOH), 4.10 (D, J=12.0 Hz, 1H, 32-CH2OH), 3.60 (d, J=12.0 Hz, 1H, 32-CH2OH), 3.23 (dd, J=11.0 Hz, 4.5Hz, 1H, 3-CHOH), 3.00 (bm, 3H, OH), 2.70 (m, 1H), 2.30 (m, 6H), 2.10–0.85 (m, 23H), 1.03 (s, 6H, CH3), 0.97 (s, 3H, CH3), 0.95 (d, J=7.0 Hz, 3H, 21-CH3), 0.93 (d, J=7.0 Hz, 6H, 26-CH3 and 27-CH3), 0.73 (s, 3H, 18-CH3).

Y. Preparation of 3β,15α-dihydroxy-lanost-8-en32-al (Compound 50a)

To a cold (−50°) dichloromethane solution (1.5 mL) of lanost-8-ene-3β,15α32-triol (Compound 49a) (30 mg, 70 μmol) was added recrystallized (water then dried under vacuum and phosphorous pentoxide) pyridinium dichromate (15 mg, 70 μmol). The reaction mixture was permitted to reach −30° and followed by thin layer chromatography until complete (ca. 1 hour) at which time the reaction was quenched with isopropanol (1 mL) then diluted with diethyl ether (50 mL). The solution was filtered through a bed of Florsil (Fischer) then concentrated to give a residue that was purified by silica gel chromatography (15% ethyl acetate in hexanes). In this fashion pure Compound 50a was obtained in 63% yield (18 mg).

Physical Data (Compound 50a):
NMR (300 MHz, CDCl3): 9.58 (s, 1H, CHO), 4.20 (m, 1H, 15-CHOH), 4.00 (d, J=10.0 Hz, 1H, OH, exchangeable with D2O), 3.28 (m, 1H, 3 -CHOH), 2.40–0.85 (m, 24 ), 1.10 (s, 3H, CH3), 1.03 (s, 3H, CH3), 0.89 (d, J=7.0 Hz, 3H, CH3), 0.86 (d, J=7.0 Hz, 6 Hz, 26-CH3 and 27-CH3), 0.85 (s, 3H, CH3), 0.78 (s, 3H, 18-CH3).

EXAMPLES 2–13

Inhibition and Suppression of Cholesterogenic Enzymes in Mammalian Cells

A. 3-Hydroxy-3-Methylglutaryl Coenzyme A Reductase (HMGR) Suppression Assay The ability of the compounds of Formula I to suppress the activity of HMGR, the rate limiting enzyme of cholesterol biosynthesis, was tested as follows. Chinese Hamster Ovary (CHO) cells were divided twice weekly and were maintained in McCoy's 5A medium supplemented with 1% Cab-O-Sil delipidated Fetal Bovine Serum (FBS) (obtained from Gibco Laboratories, Chagrin Falls, Ohio). Cells were harvested during the logarithmic phase of growth and cell cultures were prepared by adding $0.5 \times 10^6$ cells to wash well in a 4 well cluster dish (obtained from Costar, Data Packaging Corp., Cambridge, Mass.) employing 1 mL of the above medium per each well. The cell cultures were incubated for 48 hr at 37° in a 5% CO2, 95% air environment. The test compounds in a 2.5 % suspension of bovine serum albumin (BSA) (fatty acid free) in ethanol were then added to the cultures such that the final ethanol and BSA concentrations in the incubation medium were 0.5% and 0.25% respectively. Treated cells were incubated with the indicated compounds for 6 hr at 37° in a 5% CO2, 95% air environment. Control cells were treated in an identical fashion to those which received test compound, except they were incubated with the BSA and ethanol suspension only.

HMGR activity was then measured in digitoninpermeabilized cells by the method developed by Leonard et al., *J. Biol. Chem.*, 262:7914–7919 (1987). Specifically, the medium in each well was aspirated and the cells rinsed with a 50 mM solution of phosphate buffered saline (PBS). One mL of 30 μg/mL of digitonin in CSK buffer (prepared using 10 mM Pipes [piperazine-N,N'-bis(2-ethansulfonic)acid'], 100 mM KCl, 2.5 mM MgCl₂, 300 mM sucrose, 1 mM EGTA, pH 6.8) was added to each well and incubated for 10 min at 22° to permeabilize the cells. The buffer was carefully aspirated and the wells were rinsed twice each time with 1 mL of PBS. HMGR activity was measured directly by adding 75 μL of PIB buffer (50 mM potassium phosphate, 1 mM Na₂EDTA, 10 mM dithiothreitol, pH 7.4) to each well and incubating the cells for 30 minutes at 37° as described above. The enzyme assay was initiated by the addition of 83 μL of substrate/cofactor mixture such that the final assay contained the following: 0.1M potassium phosphate, 5 mM dithiothreitol, 20 mM glucose-6-phosphate, 2.5 mM NADP, 0.175 units of glucose-6-phosphate dehydrogenase, 150 μM [$^{14}$C] HMG-Coenzyme A (15 DPM/pmol), pH 7.4. The assay mixture was incubated for 30 min at 37° and terminated by the addition of 70 μL of [$^3$H]-mevalonic acid (35,000 DPM/assay), 0.15 mg/mL in 3 N HCl. The reaction was left to lactonize for an additional 30 min at 37° or overnight at room temperature.

Reaction products were separated by thin layer chromatography on silica gel G (obtained from Analtech, Newark, Del.) developed in an unsaturated environment with acetone:benzene (3:2, v:v). The band corresponding to mevalonolactone was identified by exposure to iodine vapor and was scraped into counting vials. The extent of conversion of starting substrate, HMG-CoA, to mevalonic acid was determined by liquid scintillation counting in Biofluor (obtained from New England Nuclear, Boston, Mass). Corrections for recovery and blank values were made for each sample. Protein determinations were made by the Bio-rad (Bio-Rad, Richmond, Cal.) dye binding assay according to the manufacturer's instruction using bovine serum albumin as standard. Cellular protein was solubilized from culture dishes by the addition of 20 μL of 16 N KOH and assayed directly for protein amount. Suppression values are expressed as the amount of compound required to suppress HMGR activity by 50% relative to that of the controls.

B. Lanosta-8,24-dien-3β-ol 14α-Methyl Demethylase Inhibition Assay

Lanosta-8,24-dien-3β-ol 14α-methyl demethylase activity was determined in rat depatic microsomal preparations as described in Trzaskos et al., *J. Biol. Chem.*, 261, 16937-16942 (1986). Specifically, test compounds were added to assay mixtures as detergent suspensions with substrate employing 5 mg Triton WR-1339, 100 μM lanost-8-en-3β-ol substrate, and test compounds ranging from 0 to 100 μM. The inhibitor/substrate/detergent suspension was incubated with 2 mg microsomal protein for 5 min at 37° followed by a 10 min incubation initiated by the addition of cofactors required for the reaction. Inhibition values were calculated by comparing the enzymic activity in inhibitor-containing assays with those of control assays which did not receive added compounds. Inhibition values are expressed as the amount of compound required to inhibit lanosta-8,24-dien-3β-ol 14α-methyl demethylase activity by 50% relative to that of the controls.

The results of Assays A and B are reported in Table I below.

TABLE I

Effect of Various Test Compounds Upon Measured HMGR and Lanosta-8,24-dien-3β-ol 14α-Methyl Demethylase Activities

| Example No. | Lanosterol Compound | HMGR IC50 (μM) | Demethylase IC50 (μM) |
|---|---|---|---|
| 2 | 26b | 1.0 | >100 |
| 3 | 34a | 0.5 | 3.0 |
| 4 | 17a | 1.4 | 11.0 |
| 5 | 9a | 1.3 | 16.0 |
| 6 | 35a | 0.4 | >100 |
| 7 | 15b | 1.4 | 3.0 |
| 8 | 27b | 0.5 | >100 |
| 9 | 31b | 0.2 | 55.0 |
| 10 | 9b | 1.4 | 37.0 |
| 11 | 11a | 0.06 | 0.8 |
| 12 | 12a | 0.13 | 3.2 |
| 13 | 15a | 0.04 | 1.1 |

The ability of compounds of this invention to effectively suppress HMGR activity and inhibit lanosta-8,24-dien -3β-ol 14α-methyl demethylase activity is demonstrated by the data in Table I. As a comparison, it should be noted that cholesterol, lanosta-8,24-dien -3β-ol (Compound 1), and lanost-8-en3β-ol, when tested under these same conditions, were without effect on measured HMGR activity. In addition, with respect to lanosta-8,24-dien-3β-ol 14α-methyl demethylase activity, cholesterol was also found to be without effect, although lanosta,8-24-dien-3β-ol and lanost-8-en-3β-ol clearly served as substrates for the demethylase enzyme.

The dual mechanism of inhibition at the point of lanosta-8,24-dien-3β-ol 14α-methyl demethylation coupled with HMGR suppression makes these compounds attractive as hypocholesterolemic agents.

EXAMPLES 14–21

Decreasing Cholesterol Synthesis in Mammalian Cells

The ability of the compounds of Formula I to decrease de novo cholesterol synthesis was tested by measuring the incorporation of radiolabeled acetate into cholesterol synthesized in CHO cells. To conduct this experiment, CHO cells were plated at $0.3 \times 10^6$ cells per $15 \times 60$ mm tissue culture dish in 5 mL of McCoy's modified medium (Gibco Laboratories) containing 1% Cab-O-Sil delipidated FBS and incubated for 48 hours at 37° in a 5% CO₂, 95% air environment. Test compounds in a 2.5% suspension of BSA (fatty acid free) in ethanol were then added to the cultures such that the final ethanol and BSA concentrations were 0.5% and 2.5%, respectively. Control cultures received ethanol and BSA alone. The cultures containing test compounds were then incubated at 37° in a 5% Co, 95% air environment for 17 hr before the addition of [1,2-$^{14}$C]-acetic acid (57 μCi/mmol); obtained from New England Nuclear, Boston, Mass.) at a concentration of 10 μCi/mL for 2 additional hr.

The cells were harvested by washing the cells twice with 5 mL of cold PBS and scraping the cells into 1 mL PBS. The cell-containing solution was then transferred to 15 mL extraction tubes and treated with 1 mL of 90% methanol (containing 15% KOH, 100 μg/mL butylated hydroxytoluene). All samples were saponified for 1 hr at 80° and the non-saponifiable lipids then extracted with petroleum ether. The petroleum ether fractions were dried under nitrogen, resuspended in ethanol, counted and analyzed by reverse phase HPLC at 45° using an Ultrashpere Octyl column (from Altex Scientific Inc., Berkeley, Calif.) with a mobile phase of acetonitrile:methanol:water (44:44:12). The results are reported in Table II. The amount of cholesterol synthesis is measured by the amount of radiolabeled acetate incorporated into the cholesterol peak. The percent of cholesterol synthesis in the treated culture is calculated based upon the control culture.

TABLE II

Effect of Various Test Compounds Upon Measured Cholesterol Synthesis

| Example No. | Compound and Concentration* (μM) | Cholesterol Synthesis (DPMs) | Cholesterol Synthesis (%) |
|---|---|---|---|
| 14 | Control | 38855 | 100 |
| 15 | 26b (10) | 12279 | 32 |
| 16 | 9a (10) | 3615 | 9 |
| 17 | 9b (10) | 10125 | 26 |
| 18 | 11a (1) | 360 | 1 |
| 19 | 12a (1) | 636 | 2 |
| 20 | 34a (1) | 16521 | 43 |
| 21 | 31b (0.5) | 24064 | 62 |
| 22 | 15b (0.5) | 1534 | 4 |

*Concentration in brackets.

The ability of compounds of the present invention to decrease de novo cholesterol synthesis is demonstrated by the data in Table II.

EXAMPLES 23-24

Lowering Blood Cholesterol Levels in Hamsters

The ability of the compounds of Formula I to lower blood cholesterol levels has been demonstrated in hamsters utilizing the following protocol. Male Golden Syrian hamsters (50-60 grams) were obtained from Charles River, Inc. (Wilmington, Mass.). Animals were housed in individual suspension cages and were maintained on a light cycle consisting of 12 hours of light followed by 12 hours of dark. Animals were allowed free access to water and feed (Agway ground chow, RMH 3200, Agway, Syracuse, N.Y.) containing 1% (w/w) corn oil) for a minimum of 4 weeks. Following this stabilization period a sample of blood was collected by orbital sinus bleeding under light ether anesthesia into heparinized capillary tubes. Plasma was separated by centrifugation (600×g for 10 minutes) and plasma cholesterols were determined by an autoanalyzer (Centrifichem 600, Baker Instruments, Allentown, Pa.). Based upon measured plasma cholesterol values, the animals were randomized into two groups such that the mean plasma cholesterol values were identical for both groups.

Animals in the two groups were then placed on one of two diets: (1) Diet A, consisting of ground chow plus 1% (w/w) corn oil, as described above; or (2) Diet B, consisting of Diet A plus 0.2% (w/w) of a test compound. Animals on Diet B, the treated animals, were allowed free access to feed and water, while animals on Diet A were pair-matched with Diet B animals and served as pair-fed controls. The animals were kept on their respective diets for 7 days at which time they were bled by cardiac puncture under $CO_2$ anesthesia. Total plasma cholesterol levels were determined as described above.

The results are presented in Table III. The data is reported as means±SEM (standard error of the means), in units of mg/dl. The value "N" represents the number of animals in each group.

TABLE III

Effect of Various Test Compounds Upon Plasma Cholesterol Levels in Hamsters

| Example No. | Compound | Plasma Cholesterol Control | Treated |
|---|---|---|---|
| | | mg/dl | |
| 23 | 34a | 136.0 ± 3.5 (N = 16) | 119.3 ± 2.3 (N = 16) |
| 24 | 31b | 136.0 ± 4.8 (N = 16) | 69.6 ± 2.6 (N = 16) |

As the data in Table III indicates, blood cholesterol levels can be significantly lowered by administration of compounds of Formula I.

What is claimed is:

1. A compound of the formula:

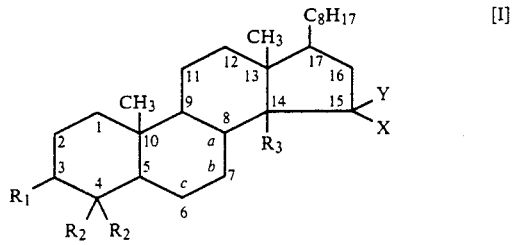

wherein $R_1$ is =O, $OL_1$, or $OCOL_1$;

$R_2$ is H, $C_1$-$C_6$ alkyl, $C_2$-$C_6$ alkenyl, $C_2$-$C_6$ alkynyl or aryl-$C_1$-$C_6$-alkyl;

$R_3$ is H, $C_1$-$C_6$ alkyl, $C_2$-$C_6$ alkenyl, $C_2$-$C_6$ alkynyl, aryl-$C_1$-$C_6$-alkyl, $CH_2OR_4$, $CH_2CH_2OR_4$, $CHNOR_4$, $CH_2SR_4$, $CH_2CH_2SR_4$, $CHOR_4L_2$, $CHOR_5L_2$, CN, $CHZ_2$, $CHR_4N(R_4)_2$, $CH_2CH_2N(R_4)_2$, $CH_2CH_2Z$, $N(R_4)_2$, $SR_4$, $OR_4$, poly-($OR_4$, $OR_5$, epoxy) $C_1$-$C_6$ alkyl, $NR_4R_5$, $OR_5$, $CH_2CH_2OR_5$, $CHNOR_5$, $CH_2CH_2SR_5$, $CH_2CH_2NR_4OR_4$, $CHR_4NR_4OR_5$, $COL_3$, $C(NR_4)L_2$, $CH_2CH_2NR_4OR_5$, $CHR_4NR_4OR_4$, $CHR_4NR_5OR_5$, $CR_4=CR_4C(R_4)_2Z$, $CR_4=CR_4C(R_4)_2OR_5$, $CR_4=CR_4C(R_4)_2OR_4$, $C(O)NR_4OR_4$, $C(O)NR_4OR_5$, CHO, $CR_4=CR_4R_5$, $C(R_4)_2OR_4$, $C(R_4)_2OR_5$, $C(R_4)_2CR_4NOR_4$ or $C(R_4)_2CR_4NOR_5$;

$R_4$ is H, $C_1$-$C_6$ alkyl, $C_2$-$C_6$ alkenyl, aryl, aryl-$C_1$-$C_6$-alkyl or $C_2$-$C_6$ alkynyl;

$R_5$ is $COL_3$;

X and Y, independently, are H, $C_1$-$C_6$ alkyl, Z, $OR_4$, $OR_5$, $SR_4$, $SR_5$, $N(R_4)_2$, $N(R_5)_2$, $NR_4R_5$, $NR_4OR_4$ or $NR_4OR_5$; or X and Y, taken together, are $NR_4$, $NR_5$, $NOR_4$, $NOR_5$, S, $C(R_4)_2$, $C(R_5)_2$, $CR_5R_4$ or O;

Z is halogen;

$L_1$ is H, $C_1$-$C_{20}$ alkyl, $C_2$-$C_{20}$ alkenyl, aryl, aryl-$C_1$-$C_{20}$-alkyl, or $C_2$-$C_{20}$ alkynyl;

$L_2$ is H, $C_1$-$C_6$ alkyl, $C_2$-$C_6$ alkenyl, aryl, aryl-$C_1$-$C_6$-alkyl, or $C_2$-$C_6$ alkynyl;

$L_3$ is $C_1$-$C_6$ alkyl, $C_2$-$C_6$ alkenyl, aryl, aryl-$C_1$-$C_6$-alkyl, $C_2$-$C_6$ alkynyl, $OR_4$, or $N(R_4)_2$;

and their physiologically acceptable salts; provided that (a) when $R_3$ is CHO, and X and Y are both H, and carbons 7-8 or 8-9 are unsaturated, then $R_1$ is other than =O, OH or $OCOCH_3$, and $R_2$ is other than $CH_3$;

(b) when $R_3$ is $CH_3$ and carbons 7-8 or 8-9 are unsaturated, then $R_1$ is other than OH or $OCOCH_3$, $R_2$ is other than $CH_3$ or H, and X and Y are other than F, OH, $OCOCH_3$ or H;

(c) when $R_1$ is $=O$, or is $OL_1$ where $L_1$ is H or $C_1$-$C_6$ alkyl, or is $OCOL_1$ when $L_1$ is $C_1$-$C_{20}$ alkyl or aryl, and X is $OR_4$ or $OR_5$ where $R_4$ is H or $OR_5$ is $OCOL_3$ where $L_3$ is $C_1$-$C_6$ alkyl or aryl, and Y is H or OH, then $R_3$ is other than H or $\alpha$ $C_1$-$C_6$ alkyl;

(d) when $R_3$ is $CH_2OH$ or $CH_2OCOCH_3$, and $R_2$ is H or $CH_3$, and carbons 6-7, 7-8 or 8-9 are unsaturated, then $R_1$ is other than $=O$ or OH or $OCOCH_3$, and X is other than H or OH;

(e) when X and Y are both H, then $R_3$ is other than H or $CH_3$;

(f) when X and Y are both H, then $R_3$ is other than OH, and $R_2$ is other than H;

(g) when $R_2$ is H, and $R_3$ is $\alpha$ OH, and X is $\beta$ OH, and Y is $\alpha$ H, and carbons 6-7, 7-8, or 8-9 are saturated, then $R_1$ is other than OH;

(h) when X is OH, $OR_5$, $N(R_4)_2$, $N(R_5)_2$, $NR_4R_5$, $SR_5$, $NR_4OR_4$, or $NR_4OR_5$, then Y is other than Z, OH, $OR_5$, $SR_5$, $NR_4OR_4$, $NR_4OR_5$, $N(R_4)_2$, or $N(R_5)_2$;

(i) when $R_3$ is H, OH, or $C_1$-$C_6$ alkyl, then X and Y, taken together, are other than O;

(j) when $R_3$ is $\alpha$ OH, X is $\alpha$ OH and Y is H, and carbons 8-9 are unsaturated, then $R_1$ is other than $OCOCH_3$;

(k) when $R_3$ is CN, or CHNOH and carbons 7-8 are unsaturated, then $R_1$ is other than $OCOCH_3$, $R_2$ is other than H or $CH_3$, and X and Y are other than H; and (l) when $R_3$ is COOH, CONHOH or CONHOCOCH$_3$, and X and Y are both H, and $R_2$ is $CH_3$, and carbons 7-8 are unsaturated, then $R_1$ is other than OH or $OCOCH_3$.

2. A compound of claim 1 wherein
$R_3$ is H, $C_1$-$C_6$ alkyl, $C_2$-$C_6$ alkenyl, $C_2$-$C_6$ alkynyl, aryl-$C_1$-$C_6$-alkyl, $CH_2CH_2OR_4$, $CHNOR_4$, $CH_2SR_4$, $CH_2CH_2SR_4$, $CHOR_4L_2$, $CHOR_5L_2$, CN, $CHZ_2$, $CHR_4N(R_4)_2$, $CH_2CH_2N(R_4)_2$, $CH_2CH_2Z$, $N(R_4)_2$, $SR_4$, $OR_4$, poly-($OR_4$, $OR_5$, epoxy) $C_1$-$C_6$ alkyl, $NR_4R_5$, $OR_5$, $CH_2CH_2OR_5$, $CHNOR_5$, $CH_2CH_2SR_5$, $CH_2CH_2NR_4OR_4$, $CHR_4NR_4OR_5$, $COL_3$, $C(NR_4)L_2$, $CH_2CH_2NR_4OR_5$, $CHR_4NR_4OR_4$, $CHR_4NR_5OR_5$, $CR_4=CR_4C(R_4)_2Z$, $CR_4=CR_4C(R_4)_2OR_5$, $CR_4=CR_4C(R_4)_2OR_4$, $C(O)NR_4OR_4$, $C(O)NR_4OR_5$, $CR_4=CR_4R_5$, $C(R_4)_2OR_4$, $C(R_4)_2OR_5$, $C(R_4)_2CR_4NOR_4$ or $C(R_4)_2CR_4NOR_5$.

3. A compound of claim 1 wherein
$R_3$ is H, $C_1$-$C_6$ alkyl, $C_2$-$C_6$ alkenyl, $C_2$-$C_6$ alkynyl, aryl-$C_1$-$C_6$-alkyl, $CH_2OR_4$, $CH_2CH_2OR_4$, $CH_2SR_4$, $CH_2CH_2SR_4$, $CHOR_4L_2$, $CHOR_5L_2$, $CHZ_2$, $CHR_4N(R_4)_2$, $CH_2CH_2N(R_4)_2$, $CH_2CH_2Z$, $N(R_4)_2$, $SR_4$, $OR_4$, poly-($OR_4$, $OR_5$, epoxy) $C_1$-$C_6$ alkyl, $NR_4R_5$, $OR_5$, $CH_2CH_2OR_5$, $CHNOR_5$, $CH_2CH_2SR_5$, $CH_2CH_2NR_4OR_4$, $CHR_4NR_4OR_5$, $COL_3$, $C(NR_4)L_2$, $CH_2CH_2NR_4OR_5$, $CHR_4NR_4OR_4$, $CHR_4NR_5OR_5$, $CR_4=CR_4C(R_4)_2Z$, $CR_4=CR_4C(R_4)_2OR_5$, $CR_4=CR_4C(R_4)_2OR_4$, CHO, $CR_4=CR_4R_5$, $C(R_4)_2OR_4$, $C(R_4)_2OR_5$, $C(R_4)_2CR_4NOR_4$ or $C(R_4)_2CR_4NOR_5$.

4. A compound of claim 1 wherein
$R_3$ is H, $C_1$-$C_6$ alkyl, $C_2$-$C_6$ alkenyl, $C_2$-$C_6$ alkynyl, aryl-$C_1$-$C_6$-alkyl, $CH_2OR_4$, $CH_2CH_2OR_4$, $CHNOR_4$, $CH_2SR_4$, $CH_2CH_2SR_4$, $CHOR_4L_2$, $CHOR_5L_2$, CN, $CHZ_2$, $CHR_4N(R_4)_2$, $CH_2CH_2N(R_4)_2$, $CH_2CH_2Z$, $N(R_4)_2$, $SR_4$, poly-($OR_4$, $OR_5$, epoxy) $C_1$-$C_6$ alkyl, $NR_4R_5$, $OR_5$, $CH_2CH_2OR_5$, $CHNOR_5$, $CH_2CH_2SR_5$, $CH_2CH_2NR_4OR_4$, $CHR_4NR_4OR_5$, $COL_3$, $C(NR_4)L_2$, $CH_2CH_2NR_4OR_5$, $CHR_4NR_4OR_4$, $CHR_4NR_5OR_5$, $CR_4=CR_4C(R_4)_2Z$, $CR_4=CR_4C(R_4)_2OR_5$, $CR_4=CR_4C(R_4)_2OR_4$, $C(O)NR_4R_4$, $C(O)NR_4OR_5$, CHO, $CR_4=CR_4R_5$, $C(R_4)_2OR_4$, $C(R_4)_2OR_5$, $C(R_4)_2CR_4NOR_4$ or $C(R_4)_2CR_4NOR_5$.

5. A compound of claim 1 wherein
$R_3$ is H, $C_1$-$C_6$ alkyl, $C_2$-$C_6$ alkenyl, $C_2$-$C_6$ alkynyl, aryl-$C_1$-$C_6$-alkyl, $CH_2CH_2OR_4$, $CH_2SR_4$, $CH_2CH_2SR_4$, $CHOR_4L_2$, $CHOR_5L_2$, $CHZ_2$, $CHR_4N(R_4)_2$, $CH_2CH_2N(R_4)_2$, $CH_2CH_2Z$, $N(R_4)_2$, $SR_4$, poly-($OR_4$, $OR_5$, epoxy) $C_1$-$C_6$ alkyl, $NR_4R_5$, $OR_5$, $CH_2CH_2OR_5$, $CHNOR_5$, $CH_2CH_2SR_5$, $CH_2CH_2NR_4OR_4$, $CHR_4NR_4OR_5$, $COL_3$, $C(NR_4)L_2$, $CH_2CH_2NR_4OR_5$, $CHR_4NR_4OR_4$, $CHR_4NR_5OR_5$, $CR_4=CR_4C(R_4)_2Z$, $CR_4=CR_4C(R_4)_2OR_5$, $CR_4=CR_4C(R_4)_2OR_4$, $CR_4=CR_4R_5$, $C(R_4)_2OR_4$, $C(R_4)_2OR_5$, $C(R_4)_2CR_4NOR_4$ or $C(R_4)_2CR_4NOR_5$.

6. A compound of claim 1 wherein
X and Y, independently, are H, $C_1$-$C_6$ alkyl, Z, $SR_4$, $SR_5$, $N(R_4)_2$, $N(R_5)_2$, $NR_4R_5$, $NR_4OR_4$ or $NR_4OR_5$; or X and Y, taken together, are $NR_4$, $NR_5$, $NOR_4$, $NOR_5$, S, $C(R_4)_2$, $C(R_5)_2$, $CR_5R_4$.

7. A compound of claim 1 wherein
X and Y, independently, are H, $C_1$-$C_6$ alkyl, $OR_4$, $OR_5$, $SR_4$, $SR_5$, $N(R_4)_2$, $N(R_5)_2$, $NR_4R_5$, $NR_4OR_4$ or $NR_4OR_5$; or X and Y, taken together, are $NR_4$, $NR_5$, $NOR_4$, $NOR_5$, S, $C(R_4)_2$, $C(R_5)_2$, $CR_5R_4$ or O.

8. A compound of claim 1 wherein
X and Y, independently, are H, $C_1$-$C_6$ alkyl, Z, $OR_4$, $OR_5$, $SR_4$, $SR_5$, $N(R_4)_2$, $N(R_5)_2$, $NR_4R_5$, $NR_4OR_4$ or $NR_4OR_5$; or X and Y, taken together, are $NR_4$, $NR_5$, $NOR_5$, S, $C(R_4)_2$, $C(R_5)_2$, $CR_5R_4$ or O.

9. A compound of claim 1 wherein
X and Y, independently, are H, $C_1$-$C_6$ alkyl, Z, $OR_4$, $OR_5$, $SR_4$, $SR_5$, $N(R_4)_2$, $N(R_5)_2$, $NR_4R_5$, $NR_4OR_4$, or $NR_4OR_5$; or X and Y, taken together, are $NR_4$, $NR_5$, $NOR_5$, S, $C(R_4)_2$, $C(R_5)_2$, $CR_4R_5$.

10. A compound of claim 1 wherein
X and Y, independently, are H, $C_1$-$C_6$ alkyl, $SR_4$, $SR_5$, $N(R_4)_2$, $N(R_5)_2$, $NR_4R_5$, $NR_4OR_4$ or $NR_4OR_5$; or X and Y, taken together, are $NR_4$, $NR_5$, $NOR_5$, S, $C(R_4)_2$, $C(R_5)_2$, or $CR_4R_5$.

11. A compound of claim 1 wherein
$R_3$ is H, $C_1$-$C_6$ alkyl, $C_2$-$C_6$ alkenyl, $C_2$-$C_6$ alkynyl, aryl-$C_1$-$C_6$-alkyl, $CH_2CH_2OR_4$, $CH_2SR_4$, $CH_2CH_2SR_4$, $CHOR_4L_2$, $CHOR_5L_2$, $CHZ_2$, $CHR_4N(R_4)_2$, $CH_2CH_2N(R_4)_2$, $CH_2CH_2Z$, $N(R_4)_2$, $SR_4$, poly-($OR_4$, $OR_5$, epoxy) $C_1$-$C_6$ alkyl, $NR_4R_5$, $OR_5$, $CH_2CH_2OR_5$, $CHNOR_5$, $CH_2CH_2SR_5$, $CH_2CH_2NR_4OR_4$, $CHR_4NR_4OR_5$, $COL_3$, $C(NR_4)L_2$, $CH_2CH_2NR_4OR_5$, $CHR_4NR_4OR_4$, $CHR_4NR_5OR_5$, $CR_4=CR_4C(R_4)_2Z$, $CR_4=CR_4C(R_4)_2OR_5$, $CR_4=CR_4C(R_4)_2OR_4$, $CR_4=CR_4R_5$, $C(R_4)_2OR_4$, $C(R_4)_2OR_5$, $C(R_4)_2CR_4NOR_4$ or $C(R_4)_2CR_4NOR_5$;

$R_4$ is H, $C_1$-$C_6$ alkyl, $C_2$-$C_6$ alkenyl, aryl, aryl-$C_1$-$C_6$-alkyl or $C_2$-$C_6$ alkynyl;

$R_5$ is $COL_3$;

X and Y, independently, are H, $C_1$-$C_6$ alkyl, $SR_4$, $SR_5$, $N(R_4)_2$, $N(R_5)_2$, $NR_4R_5$, $NR_4OR_4$ or $NR_4OR_5$; or X and Y, taken together, are $NR_4$, $NR_5$, $NOR_5$, S, $C(R_4)_2$, $C(R_5)_2$, or $CR_5R_4$.

12. A compound of claim 1 wherein $R_1$ is =O, $OL_1$, or $OCOL_1$;

$R_2$ is H, $C_1$-$C_3$ alkyl or $C_2$-$C_3$ alkenyl;

$R_3$ is H, $C_1$-$C_4$ alkyl, $C_2$-$C_4$ alkenyl, $CH_2OR_4$, $CH_2CH_2OR_4$, $CHNOR_4$, $CH_2SR_4$, $CHOR_4L_2$, CN, $CHZ_2$, $CH_2N(R_4)_2$, $CH_2CH_2Z$, $SR_4$, $OR_4$, poly-$(OR_4, OR_5$, epoxy) $C_1$-$C_4$ alkyl, $NHR_5$, $COL_3$, $C(O)NR_4OR_4$, $C(O)NR_4OR_5$, CHO or $C(R_4)=CR_4R_5$;

$R_4$ is H, $C_1$-$C_3$ alkyl, $C_2$-$C_3$ alkenyl, aryl, aryl-$C_1$-$C_2$-alkyl or $C_2$-$C_3$ alkynyl;

$R_5$ is $COL_3$;

X and Y, independently, are H, Z, $OR_4$, $N(R_4)_2$; or

X and Y, taken together, are $NOR_4$, or O;

Z is halogen;

$L_1$ is H, $C_1$-$C_6$ alkyl, $C_2$-$C_6$ alkenyl, aryl, aryl-$C_1$-$C_6$-alkyl, or $C_2$-$C_6$ alkynyl;

$L_2$ is $C_1$-$C_3$ alkyl, $C_2$-$C_3$ alkenyl, aryl, aryl-$C_1$-$C_2$-alkyl, or $C_2$-$C_3$ alkynyl;

$L_3$ is $C_1$-$C_2$ alkyl, $C_2$-$C_3$ alkenyl, aryl, aryl-$C_1$-$C_2$-alkyl, $C_2$-$C_3$ alkynyl, $OR_4$, or $N(R_4)_2$.

13. A compound of claim 1 wherein $R_1$ is =O, $OL_1$, or $OCOL_1$;

$R_2$ is H, $C_1$-$C_3$ alkyl or $C_2$-$C_3$ alkenyl;

$R_3$ is H, $C_1$-$C_4$ alkyl, $C_2$-$C_4$ alkenyl, $CH_2CH_2OR_4$, $CHNOR_4$, $CH_2SR_4$, $CHOR_4L_2$, CN, $CHZ_2$, $CH_2N(R_4)_2$, $CH_2CH_2Z$, $SR_4$, $OR_4$, poly-$(OR_4, OR_5$, epoxy) $C_1$-$C_4$ alkyl, $NHR_5$, $COL_3$, $C(O)NR_4OR_4$, $C(O)NR_4OR_5$, or $CR_4=CF_4R_5$ $R_4$ is H, $C_1$-$C_3$ alkyl, $C_2$-$C_3$ alkenyl, aryl, aryl-$C_1$-$C_2$-alkyl or $C_2$-$C_3$ alkynyl;

$R_5$ is $COL_3$;

X and Y, independently, are H, Z, $OR_4$, $N(R_4)_2$; or

X and Y, taken together, are $NOR_4$, or O;

Z is halogen;

$L_1$ is H, $C_1$-$C_6$ alkyl, $C_2$-$C_6$ alkenyl, aryl, aryl-$C_1$-$C_6$-alkyl, or $C_2$-$C_6$ alkynyl;

$L_2$ is $C_1$-$C_3$ alkyl, $C_2$-$C_3$ alkenyl, aryl, aryl-$C_1$-$C_2$-alkyl, or $C_2$-$C_3$ alkynyl;

$L_3$ is $C_1$-$C_2$ alkyl, $C_2$-$C_3$ alkenyl, aryl, aryl-$C_1$-$C_2$-alkyl, $C_2$-$C_3$ alkynyl, $OR_4$, or $N(R_4)_2$.

14. A compound of claim 1 wherein

R1 is =O, OL1, or OCOL1;

$R_2$ is H, $C_1$-$C_3$ alkyl or $C_2$-$C_3$ alkenyl;

$R_3$ is H, $C_1$-$C_4$ alkyl, $C_2$-$C_4$ alkenyl, $CH_2OR_4$, $CH_2CH_2OR_4$, $CH_2SR_4$, $CHOR_4(L_2)_2$, $CHZ_2$, $CH_2N(R_4)_2$, $CH_2CH_2Z$, $SR_4$, $OR_4$, poly-$(OR_4, OR_5$, epoxy) $C_1$-$C_4$ alkyl, $NHR_5$, $COL_3$, CHO or $CR_4=CF_4R_5$;

$R_4$ is H, $C_1$-$C_3$ alkyl, $C_2$-$C_3$ alkenyl, aryl, aryl-$C_1$-$C_2$-alkyl or $C_2$-$C_3$ alkynyl;

$R_5$ is $COL_3$;

X and Y, independently, are H, Z, $OR_4$, $N(R_4)_2$; or

X and Y, taken together, are $NOR_4$, or O;

Z is halogen;

$L_1$ is H, $C_1$-$C_6$ alkyl, $C_2$-$C_6$ alkenyl, aryl, aryl-$C_1$-$C_6$-alkyl, or $C_2$-$C_6$ alkynyl;

$L_2$ is $C_1$-$C_3$ alkyl, $C_2$-$C_3$ alkenyl, aryl, aryl-$C_1$-$C_2$-alkyl, or $C_2$-$C_3$ alkynyl;

$L_3$ is $C_1$-$C_2$ alkyl, $C_2$-$C_3$ alkenyl, aryl, aryl-$C_1$-$C_2$-alkyl, $C_2$-$C_3$ alkynyl, $OR_4$, or $N(R_4)_2$.

15. A compound of claim 1 wherein $R_1$ is =O, $OL_1$, or $OCOL_1$;

$R_2$ is H, $C_1$-$C_3$ alkyl or $C_2$-$C_3$ alkenyl;

$R_3$ is H, $C_1$-$C_4$ alkyl, $C_2$-$C_4$ alkenyl, $CH_2OR_4$, $CH_2CH_2OR_4$, $CHNOR_4$, $CH_2SR_4$, $CHOR_4L_2$, CN, $CHZ_2$, $CH_2N(R_4)_2$, $CH_2CH_2Z$, $SR_4$, poly-$(OR_4, OR_5$, epoxy) $C_1$-$C_4$ alkyl, $NHR_5$, $COL_3$, $C(O)NR_4OR_4$, $C(O)NR_4OR_5$, CHO or $CR_4=CF_4R_5$;

$R_4$ is H, $C_1$-$C_3$ alkyl, $C_2$-$C_3$ alkenyl, aryl, aryl-$C_1$-$C_2$-alkyl or $C_2$-$C_3$ alkynyl;

$R_5$ is $COL_3$;

X and Y, independently, are H, Z, $OR_4$, $N(R_4)_2$; or

X and Y, taken together, are $NOR_4$, or O;

Z is halogen;

$L_1$ is H, $C_1$-$C_6$ alkyl, $C_2$-$C_6$ alkenyl, aryl, aryl-$C_1$-$C_6$-alkyl, or $C_2$-$C_6$ alkynyl;

$L_2$ is $C_1$-$C_3$ alkyl, $C_2$-$C_3$ alkenyl, aryl, aryl-$C_1$-$C_2$-alkyl, or $C_2$-$C_3$ alkynyl;

$L_3$ is $C_1$-$C_2$ alkyl, $C_2$-$C_3$ alkenyl, aryl, aryl-$C_1$-$C_2$-alkyl, $C_2$-$C_3$ alkynyl, $OR_4$, or $N(R_4)_2$.

16. A compound of claim 1 wherein $R_1$ is =O, $OL_1$, or $OCOL_1$;

$R_2$ is H, $C_1$-$C_3$ alkyl or $C_2$-$C_3$ alkenyl;

$R_3$ is H, $C_1$-$C_4$ alkyl, $C_2$-$C_4$ alkenyl, $CH_2CH_2OR_4$, $CH_2SR_4$, $CHOR_4L_2$, $CHZ_2$, $CH_2N(R_4)_2$, $CH_2CH_2Z$, $SR_4$, poly-$(OR_4, OR_5$, epoxy) $C_1$-$C_4$ alkyl, $NHR_5$, $COL_3$, or $CR_4=CF_4R_5$;

$R_4$ is H, $C_1$-$C_3$ alkyl, $C_2$-$C_3$ alkenyl, aryl, aryl-$C_1$-$C_2$-alkyl or $C_2$-$C_3$ alkynyl;

$R_5$ is $COL_3$;

X and Y, independently, are H, Z, $OR_4$, $N(R_4)_2$; or

X and Y, taken together, are $NOR_4$, or O;

Z is halogen;

$L_1$ is H, $C_1$-$C_6$ alkyl, $C_2$-$C_6$ alkenyl, aryl, aryl-$C_1$-$C_6$-alkyl, or $C_2$-$C_6$ alkynyl;

$L_2$ is $C_1$-$C_3$ alkyl, $C_2$-$C_3$ alkenyl, aryl, aryl-$C_1$-$C_2$-alkyl, or $C_2$-$C_3$ alkynyl;

$L_3$ is $C_1$-$C_2$ alkyl, $C_2$-$C_3$ alkenyl, aryl, aryl-$C_1$-$C_2$-alkyl, $C_2$-$C_3$ alkynyl, $OR_4$, or $N(R_4)_2$.

17. A compound of claim 1 wherein $R_1$ is =O, $OL_1$, or $OCOL_1$;

$R_2$ is H, $C_1$-$C_3$ alkyl or $C_2$-$C_3$ alkenyl;

$R_3$ is H, $C_1$-$C_4$ alkyl, $C_2$-$C_4$ alkenyl, $CH_2OR_4$, $CH_2CH_2OR_4$, $CHNOR_4$, $CH_2SR_4$, $CHOR_4L_2$, CN, $CHZ_2$, $CH_2N(R_4)_2$, $CH_2CH_2Z$, $SR_4$, $OR_4$, poly-$(OR_4, OR_5$, epoxy) $C_1$-$C_4$ alkyl, $NHR_5$, $COL_3$, $C(O)NR_4OR_4$, $C(O)NR_4OR_5$, CHO or $CR_4=CF_4R_5$;

$R_4$ is H, $C_1$-$C_3$ alkyl, $C_2$-$C_3$ alkenyl, aryl, aryl-$C_1$-$C_2$-alkyl or $C_2$-$C_3$ alkynyl;

$R_5$ is $COL_3$;

X and Y, independently, are H, Z, $N(R_4)_2$; or

X and Y, taken together, are $NOR_4$;

Z is halogen;

$L_1$ is H, $C_1$-$C_6$ alkyl, $C_2$-$C_6$ alkenyl, aryl, aryl-$C_1$-$C_6$-alkyl, or $C_2$-$C_6$ alkynyl;

$L_2$ is $C_1$-$C_3$ alkyl, $C_2$-$C_3$ alkenyl, aryl, aryl-$C_1$-$C_2$-alkyl, or $C_2$-$C_3$ alkynyl;

$L_3$ is $C_1$-$C_2$ alkyl, $C_2$-$C_3$ alkenyl, aryl, aryl-$C_1$-$C_2$-alkyl, $C_2$-$C_3$ alkynyl, $OR_4$, or $N(R_4)_2$.

18. A compound of claim 1 wherein $R_1$ is =O, $OL_1$, or $OCOL_1$;

$R_2$ is H, $C_1$-$C_3$ alkyl or $C_2$-$C_3$ alkenyl;

59

$R_3$ is H, $C_1$-$C_4$ alkyl, $C_2$-$C_4$ alkenyl, $CH_2OR_4$, $CH_2CH_2OR_4$, $CHNOR_4$, $CH_2SR_4$, $CHOR_4L_2$, CN, $CHZ_2$, $CH_2N(R_4)_2$, $CH_2CH_2Z$, $SR_4$, $OR_4$, poly-($OR_4$, $OR_5$, epoxy) $C_1$-$C_4$ alkyl, $NHR_5$, $COL_3$, $C(O)NR_4OR_4$, $C(O)NR_4OR_5$, CHO or $CR_4=CF_4R_5$;

$R_4$ is H, $C_1$-$C_3$ alkyl, $C_2$-$C_3$ alkenyl, aryl, aryl-$C_1$-$C_2$-alkyl or $C_2$-$C_3$ alkynyl;

$R_5$ is $COL_3$;

X and Y, independently, are H, $OR_4$, $N(R_4)_2$; or

X and Y, taken together, are $NOR_4$, or O;

Z is halogen;

$L_1$ is H, $C_1$-$C_6$ alkyl, $C_2$-$C_6$ alkenyl, aryl, aryl-$C_1$-$C_6$-alkyl, or $C_2$-$C_6$ alkynyl;

$L_2$ is $C_1$-$C_3$ alkyl, $C_2$-$C_3$ alkenyl, aryl, aryl-$C_1$-$C_2$-alkyl, or $C_2$-$C_3$ alkynyl;

$L_3$ is $C_1$-$C_2$ alkyl, $C_2$-$C_3$ alkenyl, aryl, aryl-$C_1$-$C_2$-alkyl, $C_2$-$C_3$ alkynyl, $OR_4$, or $N(R_4)_2$.

19. A compound of claim 1 wherein
$R_1$ is =O, $OL_1$, or $OCOL_1$;
$R_2$ is H, $C_1$-$C_3$ alkyl or $C_2$-$C_3$ alkenyl;
$R_3$ is H, $C_1$-$C_4$ alkyl, $C_2$-$C_4$ alkenyl, $CH_2OR_4$, $CH_2CH_2OR_4$, $CHNOR_4$, $CH_2SR_4$, $CHOR_4L_2$, CN, $CHZ_2$, $CH_2N(R_4)_2$, $CH_2CH_2Z$, $SR_4$, $OR_4$, poly-($OR_4$, $OR_5$, epoxy) $C_1$-$C_4$ alkyl, $NHR_5$, $COL_3$, $C(O)NR_4OR_4$, $C(O)NR_4OR_5$, CHO or $CR_4=CF_4R_5$;
$R_4$ is H, $C_1$-$C_3$ alkyl, $C_2$-$C_3$ alkenyl, aryl, aryl-$C_1$-$C_2$-alkyl or $C_2$-$C_3$ alkynyl;
$R_5$ is $COL_3$;
X and Y, independently, are H, Z, $OR_4$, $N(R_4)_2$; or
X and Y, taken together, are $NOR_4$;
Z is halogen;
$L_1$ is H, $C_1$-$C_6$ alkyl, $C_2$-$C_6$ alkenyl, aryl, aryl-$C_1$-$C_6$-alkyl, or $C_2$-$C_6$ alkynyl;
$L_2$ is $C_1$-$C_3$ alkyl, $C_2$-$C_3$ alkenyl, aryl, aryl-$C_1$-$C_2$-alkyl, or $C_2$-$C_3$ alkynyl;
$L_3$ is $C_1$-$C_2$ alkyl, $C_2$-$C_3$ alkenyl, aryl, aryl-$C_1$-$C_2$-alkyl, $C_2$-$C_3$ alkynyl, $OR_4$, or $N(R_4)_2$.

20. A compound of claim 1 wherein
$R_1$ is =O, $OL_1$, or $OCOL_1$;
$R_2$ is H, $C_1$-$C_3$ alkyl or $C_2$-$C_3$ alkenyl;
$R_3$ is H, $C_1$-$C_4$ alkyl, $C_2$-$C_4$ alkenyl, $CH_2OR_4$, $CH_2CH_2OR_4$, $CHNOR_4$, $CH_2SR_4$, $CHOR_4L_2$, CN, $CHZ_2$, $CH_2N(R_4)_2$, $CH_2CH_2Z$, $SR_4$, $OR_4$, poly-($OR_4$, $OR_5$, epoxy) $C_1$-$C_4$ alkyl, $NHR_5$, $COL_3$, $C(O)NR_4OR_4$, $C(O)NR_4OR_5$, CHO or $CR_4=CF_4R_5$;
$R_4$ is H, $C_1$-$C_3$ alkyl, $C_2$-$C_3$ alkenyl, aryl, aryl-$C_1$-$C_2$-alkyl or $C_2$-$C_3$ alkynyl;
$R_5$ is $COL_3$;
X and Y, independently, are H, $N(R_4)_2$; or
X and Y, taken together, are $NOR_4$;
Z is halogen;
$L_1$ is H, $C_1$-$C_6$ alkyl, $C_2$-$C_6$ alkenyl, aryl, aryl-$C_1$-$C_6$-alkyl, or $C_2$-$C_6$ alkynyl;
$L_2$ is $C_1$-$C_3$ alkyl, $C_2$-$C_3$ alkenyl, aryl, aryl-$C_1$-$C_2$-alkyl, or $C_2$-$C_3$ alkynyl;
$L_3$ is $C_1$-$C_2$ alkyl, $C_2$-$C_3$ alkenyl, aryl, aryl-$C_1$-$C_2$-alkyl, $C_2$-$C_3$ alkynyl, $OR_4$, or $N(R_4)_2$.

21. A compound of claim 1 wherein
$R_1$ is =O, $OL_1$, or $OCOL_1$;
$R_2$ is H, $C_1$-$C_3$ alkyl or $C_2$-$C_3$ alkenyl;
$R_3$ is H, $C_1$-$C_4$ alkyl, $C_2$-$C_4$ alkenyl, $CH_2CH_2OR_4$, $CH_2SR_4$, $CHOR_4L_2$, $CHZ_2$, $CH_2N(R_4)_2$, $CH_2CH_2Z$, $SR_4$, poly-($OR_4$, $OR_5$, epoxy) $C_1$-$C_4$ alkyl, $NHR_5$, $COL_3$, CHO or $CR_4=CF_4R_5$;

60

$R_4$ is H, $C_1$-$C_3$ alkyl, $C_2$-$C_3$ alkenyl, aryl, aryl-$C_1$-$C_2$-alkyl or $C_2$-$C_3$ alkynyl;
$R_5$ is $COL_3$;
X and Y, independently, are H, $N(R_4)_2$; or
X and Y, taken together, are $NOR_4$;
Z is halogen;
$L_1$ is H, $C_1$-$C_6$ alkyl, $C_2$-$C_6$ alkenyl, aryl, aryl-$C_1$-$C_6$-alkyl, or $C_2$-$C_6$ alkynyl;
$L_2$ is $C_1$-$C_3$ alkyl, $C_2$-$C_3$ alkenyl, aryl, aryl-$C_1$-$C_2$-alkyl, or $C_2$-$C_3$ alkynyl;
$L_3$ is $C_1$-$C_2$ alkyl, $C_2$-$C_3$ alkenyl, aryl, aryl-$C_1$-$C_2$-alkyl, $C_2$-$C_3$ alkynyl, $OR_4$, or $N(R_4)_2$.

22. A compound of claim 1 wherein
$R_1$ is OH, $OCOCH_3$ or OCOPh;
$R_2$ is H or $CH_3$;
$R_3$ is H, $CH_3$, $CH=CH_2$, $CH_2CH=CH_2$, $CH_2OH$, $CH_2CH_2CH$, CHNOH, $CH_2SCH_3$, $CHOHCH=CH_2$, $CHOHC\equiv CH$, CN, $CHF_2$, $CH_2CH_2Br$, $SCH_3$, OH, $CHOHCH_2OH$, $CHOHCHOHCH_2OH$,

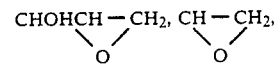

NHCHO, $COCH=CH_2$, $CO_2H$, $CONH_2$, $CONHOH$, CHO, $CO_2CH_3$ or $CH=CHCO_2CH_3$; and
X and Y, independently, are H, F, OH or $NH_2$; or
X and Y, together, are NOH or O.

23. A compound of claim 1 wherein
$R_1$ is OH or $OCOCH_3$;
$R_2$ is or $CH_3$;
$R_3$ is H, $CH_3$, $CH=CH_2$, $CH_2CH=CH_2$, $CH_2CH_2CH$, CHNOH, $CH_2SCH_3$, $CHOHCH=CH_2$, $CHOHC\equiv CH$, CN, $CHF_2$, $CH_2CH_2Br$, $SCH_3$, OH, $CHOHCH_2OH$, $CHOHCHOHCH_2OH$,

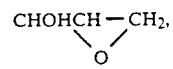

NHCHO, $COCH=CH_2$, $CO_2H$, $CONH_2$, $CONHOH$, $CO_2CH_3$ or $CH=CHCO_2CH_3$; and
X and Y, independently, are H, F, OH or $NH_2$; or
X and Y, together, are NOH or O.

24. A compound of claim 1 wherein
$R_1$ is OH;
$R_2$ is H or $CH_3$;
$R_3$ is $CH_3$, $CH=CH_2$, $CH_2CH=CH_2$, $CH_2CH_2CH$, $CH_2SCH_3$, $CHOHCH=CH_2$, $CHOHC\equiv CH$, $CHF_2$, $CH_2CH_2Br$, $SCH_3$, OH, $CHOHCH_2OH$, $CHOHCHOHCH_2OH$,

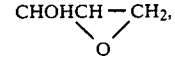

NHCHO, $COCH=CH_2$, $CO_2H$, $CONH_2$, $CO_2CH_3$ or $CH=CHCO_2CH_3$; and
X and Y, independently, are H, F, OH or $NH_2$; or
X and Y, together, are NOH or O.

25. A compound of claim 1 wherein
$R_1$ is OH;
$R_2$ is H or $CH_3$;
$R_3$ is $CH_3$, $CH=CH_2$, $CH_2CH=CH_2$, $CH_2CH_2CH$, CHNOH, $CH_2SCH_3$, $CHOHCH=CH_2$, CHOH- C≡CH, CN, CHF₂, CH₂CH₂Br, SCH₃, CHOHCH₂OH, CHOHCHOHCH₂OH,

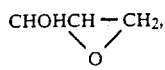

CH—CH₂, NHCHO, COCH=CH₂, CO₂H, CONH₂CONHOH, CO₂CH₃ or CH=CHCO₂CH₃; and
X and Y, independently, are H, F, OH or NH₂; or
X and Y, together, are NOH or O.

26. A compound of claim 1 wherein
R₁ is OH;
R₂ is H or CH₃;
R₃ is H, CH₃, CH=CH₂, CH₂CH=CH₂, CH₂OH, CH₂CH₂CH, CHNOH, CH₂SCH₃, CHOHCH=CH₂, CHOHC≡CH, CN, CHF₂, CH₂CH₂Br, SCH₃, OH, CHOHCH₂OH, CHOHCHOHCH₂OH,

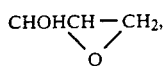

NHCHO, COCH=CH₂, CO₂H, CONH₂, CONHOH, CHO, CO₂CH₃ or CH=CHCO₂CH₃; and
X and Y, independently, are H or F; or
X and Y, together, are NOH.

27. A compound of claim 1 wherein
R₁ is OH;
R₂ is H or CH₃;
R₃ is H, CH₃, CH=CH₂, CH₂CH=CH₂, CH₂OH, CH₂CH₂CH, CHNOH, CH₂SCH₃, CHOHCH=CH₂, CHOHC≡CH, CN, CHF₂, CH₂CH₂Br, SCH₃, OH, CHOHCH₂OH, CHOHCHOHCH₂OH,

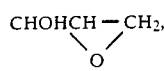

NHCHO, COCH=CH₂, CO₂H, CONH₂, CONHOH, CHO, CO₂CH₃ or CH=CHCO₂CH₃; and
X and Y, independently, are H, or OH; or
X and Y, together, are NOH or O.

28. A compound of claim 1 wherein
R₁ is OH;
R₂ is H or CH₃;
R₃ is H, CH₃, CH=CH₂, CH₂CH=CH₂, CH₂OH, CH₂CH₂CH, CHNOH, CH₂SCH₃, CHOHCH=CH₂, CHOHC≡CH, CN, CHF₂, CH₂CH₂Br, SCH₃, OH, CHOHCH₂OH, CHOHCHOHCH₂OH,

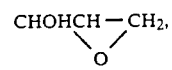

NHCHO, COCH=CH₂, CO₂H, CONH₂, CONHOH, CHO, CO₂CH₃ or CH=CHCO₂CH₃; and
X and Y, independently, are H; or
X and Y, together, are NOH.

29. A compound of claim 1 wherein
R₁ is OH;
R₂ is H or CH₃;
R₃ is CH₃, CH=CH₂, CH₂CH=CH₂, CH₂CH₂CH, CH₂SCH₃, CHOHCH=CH₂, CHOHC≡CH, CHF₂, CH₂CH₂Br, SCH₃, CHOHCH₂OH, CHOHCHOHCH₂OH,

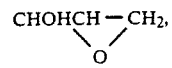

NHCHO, COCH=CH₂, CO₂H, CONH₂, CONHOH, CHO, CO₂CH₃ or CH=CHCO₂CH₃; and
X and Y, independently, are H; or
X and Y, together, are NOH.

30. A compound of claim 1 wherein
R₁ is OH;
R₂ is H or CH₃;
R₃ is CH₃, CH₂CH=CH₂, CHNOH, CN, or CHF₂; and
X and Y, independently, are H, F, OH or NH₂; or
X and Y, together, are NOH.

31. A compound of claim 1 wherein
R₁ is OH;
R₂ is H or CH₃;
R₃ is CH₃, CH=CH₂, CH₂OH, CH₂SCH₃, CHOHCH=CH₂, CHOHC≡CH, SCH₃, OH, CHOHCH₂OH, COCH=CH₂, CO₂H, CONH₂, or CONHOH; and
X and Y, independently, are H, OH; or
X and Y, together, are NOH or O.

32. A compound of claim 1 wherein
R₁ is OH;
R₂ is H or CH₃;
R₃ is CH₃, CH=CH₂, CH₂OH, CH₂SCH₃, CHOHCH=CH₂, CHOHC≡CH, SCH₃, COCH=CH₂, CO₂H or CONH₂; and
X and Y, independently, are H, OH; or
X and Y, together, are NOH or O.

33. A compound selected from the group consisting of
32,32-difluoro-lanost-8-en-3β-ol;
32,32-difluoro-lanost-7-en-3β-ol;
4,4-dimethyl-14α-(1'-hydroxy-2'-propenyl)-5α-cholest-8-en-3β-ol;
14α-allyl-4,4-dimethyl-5α-cholest-8-en-3β-ol-15-oxime;
lanost-8-en-32-aldoxime-3β-ol;
lanost-7-en-32-aldoxime-3β-ol;
14α-cyano-4,4-dimethyl-5α-cholest-8-en-3β-ol;
15α-fluoro-14α-methyl-5α-cholest-7-en-3β-ol;
3β-hydroxy-lanost-8-en-32-oxime;
3β-hydroxy-lanost-7-en-32-oxime;
4,4-dimethyl-5α-cholest-8-en-3β,14α,15α-triol;
5α-cholest-8-en-3β,14α,15α-triol;
3β-hydroxy-lanost-8-en-32-ohydroxamic acid;
3β,15α-dihydroxy-lanost-8-en-32-al;
3β-hydroxy-lanost-8-en-32-aldoxime-15-oxime;
3β-acetoxy-lanost-8-en-32-aldoxime;
3β-acetoxy-lanost-7-en-15-oxime;
lanost-6-en-32-aldoxime-3β-ol;
15α-amino-lanost-8-en-3β-ol;
14α-amino-4,4-dimethyl-5α-cholest-8-en-3β-ol;
4,5-dimethyl-14α-(N-formyl-amino)-5α-cholest-8-en-3β-ol;
4,4-dimethyl-14α-(N-ethoxycarbonylamino)-5α-cholest-8-en-3β-ol;
32-ethynyl-lanost-8-ene-3β,32-diol;
lanost-8-ene-3β,15αm32-triol;
4,4-dimethyl-14α-vinyl-5α-cholest-8-en-3β-ol;
3β-hydroxy-lanost-8-ene-32-carboxylic acid;
3β-hydroxy-lanost-8-ene-32-carboxamide;
3β-hydroxy-32-vinyl-lanost-8-en-32-on;

32-hydroxymethyl-lanost-8-en-3β-ol;
32-hydroxymethyl-lanost-8-ene-3β32-diol;
15α-fluoro-32-vinyl-lanost-7-en-3β-ol;
4,4-dimethyl-3β-hydroxy-14α-methylthio-5β-cholest-8-en-15-on;
3β-hydroxy-32-methylthio-lanost-8-en-15-on;
32-ethyl-3β-hydroxy-lanost-8-en-15-oxime;
14α-(1'-hydroxy-2'-propenyl)-5α-cholest-8-en-3β-ol; and
3β-hydroxy-14α-methyl-5α-cholest-8-en-15-oxime.

34. A compound of claim 33 which is 32,32-difluoro-lanost-8-en-3β-ol.

35. A compound of claim 33 which is 32,32-difluoro-lanost-7-en-3β-ol.

36. A compound of claim 33 which is 4,4-dimethyl-14α-(1'-hydroxy-2'-propenyl)-5α-cholest-8-en-3β-ol.

37. A compound of claim 33 which is 14α-allyl-4,4-dimethyl-5α-cholest-8-en-3β-ol-15-oxime.

38. A compound of claim 33 which is lanost-8-en-32-aldoxime-3β-ol.

39. A compound of claim 33 which is lanost-7-en-32-aldoxime-3β-ol.

40. A compound of claim 33 which is 14α-cyano-4,4-dimethyl-5α-cholest-8-en-3β-ol.

41. A compound of claim 33 which is 15α-fluoro-14α-methyl-5α-cholest-7-en-3β-ol.

42. A compound of claim 33 which is 3β-hydroxy-lanost-8-en-15-oxime.

43. A compound of claim 33 which is 3β-hydroxy-lanost-7-en-15-oxime.

44. A compound of claim 33 which is 4,4-dimethyl-5α-cholest-8-en-3β,14α,15α-triol 45. A compound of claim 33 which is 5α-cholest-8-en-3β,14α,15α-triol.

46. A compound of claim 33 which is 3β-hydroxy-lanost-8-en-32-ohydroxamic acid.

47. A compound of claim 33 which is 3β,15α-dihydroxy-lanost-8-en-32-al.

48. A compound of claim 33 which is 3β-hydroxy-lanost-8-en-32-aldoxime-15-oxime.

49. A compound of claim 33 which is 3β-acetoxy-lanost-8-en-32-alkoxime.

50. A compound of claim 33 which is 3β-acetoxy-lanost-7-en-15-oxime.

51. A compound of claim 33 which is lanost-6-en-32-aldoxime-3β-ol.

52. A compound of claim 33 which is 15α-amino-lanost-8-en-3β-ol.

53. A compound of claim 33 which is 14α-amino-4,4-dimethyl-5β-cholest-8-en-3β-ol.

54. A compound of claim 33 which is 4,4-dimethyl-14β-(N-formyl-amino)-5α-cholest-8-en-3β-ol.

55. A compound of claim 33 which is 4,4-dimethyl-14α-(N-ethoxycarbonylamino)-5α-cholest-8-en-3β-ol.

56. A compound of claim 33 which is 32-ethynyl-lanost-8-ene-3β,32-diol.

57. A compound of claim 33 which is lanost-8-ene-3β,15αm32-triol.

58. A compound of claim 33 which is 4,4-dimethyl-14α-vinyl-5α-cholest-8-en-3β-ol.

59. A compound of claim 33 which is 3β-hydroxy-lanost-8-ene-32-carboxylic acid.

60. A compound of claim 33 which is 3β-hydroxy-lanost-8-ene-32-carboxamide.

61. A compound of claim 33 which is 3β-hydroxy-32-vinyl-lanost-8-en-32-on.

62. A compound of claim 33 which is 32-hydroxymethyl-lanost-8-en-3β-ol.

63. A compound of claim 33 which is 32-hydroxymethyl-lanost-8-ene-3β32-diol.

64. A compound of claim 33 which is 15α-fluoro-32-vinyl-lanost-7-en-3β-ol.

65. A compound of claim 33 which is 4,4-dimethyl-3β-hydroxy-14α-methylthio-5β-cholest-8-en-15-on.

66. A compound of claim 33 which is 3β-hydroxy-32-methylthio-lanost-8-en-15-on.

67. A compound of claim 33 which is 32-ethyl-3β-hydroxy-lanost-8-en-15-oxime.

68. A compound of claim 33 which is 14α-(1'-hydroxy-2'-propenyl)-5α-cholest-8-en-3β-ol.

69. A compound of claim 33 which is 3β-hydroxy-14α-methyl-5α-cholest-8-en-15-oxime.

* * * * *